United States Patent
Doller et al.

(10) Patent No.: US 9,212,165 B2
(45) Date of Patent: Dec. 15, 2015

(54) BICARBOCYCLIC AND TRICARBOCYCLIC ETHYNYL DERIVATIVES AND USES OF SAME

(71) Applicant: H. Lundbeck A/S, Valby (DK)

(72) Inventors: Dario Doller, Sparta, NJ (US); Guiying Li, River Edge, NJ (US)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 14/344,957

(22) PCT Filed: Sep. 17, 2012

(86) PCT No.: PCT/US2012/055689
§ 371 (c)(1),
(2) Date: Mar. 14, 2014

(87) PCT Pub. No.: WO2013/040535
PCT Pub. Date: Mar. 21, 2013

(65) Prior Publication Data
US 2014/0350030 A1    Nov. 27, 2014

Related U.S. Application Data

(60) Provisional application No. 61/535,423, filed on Sep. 16, 2011.

(51) Int. Cl.
| | | |
|---|---|---|
| *A61K 31/497* | (2006.01) | |
| *C07D 241/10* | (2006.01) | |
| *C07D 401/12* | (2006.01) | |
| *C07D 403/12* | (2006.01) | |
| *C07D 213/81* | (2006.01) | |
| *C07D 333/38* | (2006.01) | |
| *C07D 241/12* | (2006.01) | |
| *C07D 417/12* | (2006.01) | |
| *C07D 241/24* | (2006.01) | |

(52) U.S. Cl.
CPC ............ *C07D 401/12* (2013.01); *C07D 213/81* (2013.01); *C07D 241/12* (2013.01); *C07D 241/24* (2013.01); *C07D 333/38* (2013.01); *C07D 403/12* (2013.01); *C07D 417/12* (2013.01)

(58) Field of Classification Search
CPC ... A61K 31/497; C07D 241/10; C07D 401/12
USPC .......... 544/336, 405, 406; 514/252.1, 255.05, 514/255.06
See application file for complete search history.

(56) References Cited

U.S. PATENT DOCUMENTS

| 5,652,335 | A | 7/1997 | Kitagawa et al. |
| 8,440,837 | B2 | 5/2013 | Hopper et al. |
| 8,921,370 | B2 * | 12/2014 | Li et al. .................... 514/252.11 |
| 2006/0025400 | A1 | 2/2006 | Askew et al. |

FOREIGN PATENT DOCUMENTS

| WO | 2010/011570 A1 | 1/2010 |
| WO | 2011/087758 A1 | 7/2011 |

OTHER PUBLICATIONS

Extended European Search Report dated Mar. 17, 2015, in European Applican No. 12832299.7 filed Sep. 17, 2012.

* cited by examiner

*Primary Examiner* — Golam M M Shameem
(74) *Attorney, Agent, or Firm* — Mary Catherine Di Nunzio

(57) ABSTRACT

The present invention provides compounds of formula (I):

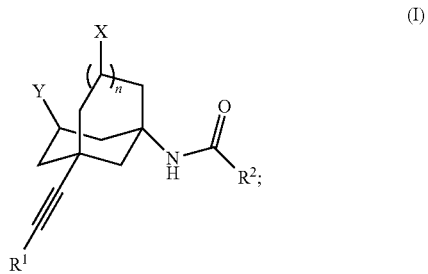

where $R^1$, $R^2$, X, Y and n are as described herein, and pharmaceutical compositions, uses and methods comprising same.

14 Claims, 1 Drawing Sheet

| | |
|---|---|
| Injection Date Time Stamp | 11-10-28 4:10:58 PM |
| Injection Volume | 5 |
| Co-Solvent | MEOH (0.1%DEA) |
| Column | AD-H (4.6*250mm, 5um) |
| Sample | CP-7390-133-1 |
| Sample Well | P1: 4A |
| Column Temperature | 38.7 |
| CO2 Flow Rate | 2.55 |
| Co-Solvent Flow Rate | 0.45 |
| Co-Solvent % | 15 |
| Back Pressure | 149 |
| Total Flow | 3 |
| PDA Start Wavelength | 214 |
| PDA Stop Wavelength | 359 |
| Injection Info | |
| Number | RT (min) | Area | Area% |
|---|---|---|---|
| 1 | 4.44 | 5227.5339 | 50.3561 |
| 2 | 5.6 | 5153.5897 | 49.6439 |
Peak Info
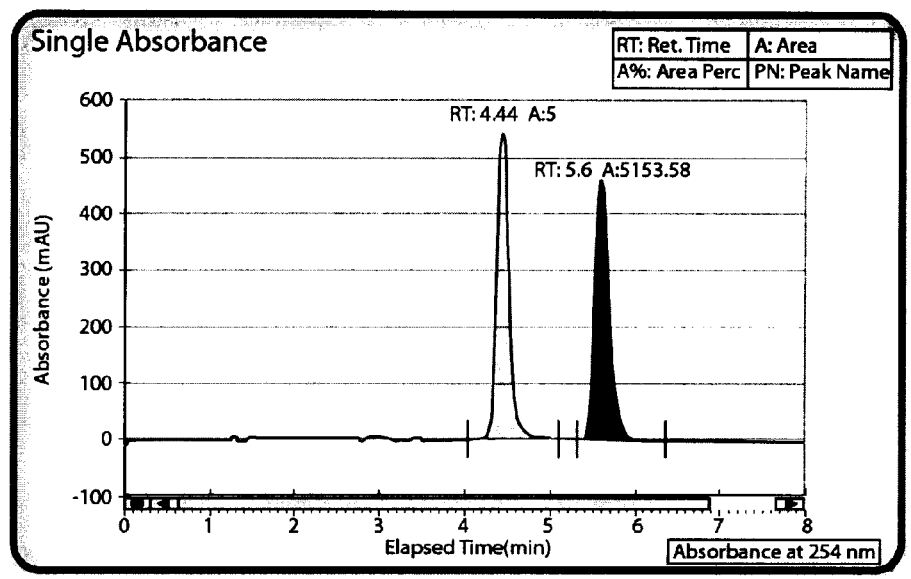
PDASingleSpectrumGraph
PDASingleSpectrumPict.png

BICARBOCYCLIC AND TRICARBOCYCLIC ETHYNYL DERIVATIVES AND USES OF SAME

FIELD OF THE INVENTION

The present invention provides bicarbocyclic and tricarbocyclic ethynyl derivatives, as well as pharmaceutical compositions and methods of treatment using same.

BACKGROUND OF THE INVENTION

This invention concerns bicarbocyclic and tricarbocyclic ethynyl derivatives which act as allosteric modulators of the metabotropic glutamate receptor 5 (mGlu5 receptors or mGluR5), as well as pharmaceutical compositions and methods of treatment utilizing these compounds.

Glutamate is the major excitatory neurotransmitter in the mammalian central nervous system. One means of modulating glutamate neurotransmission is through metabotropic glutamate receptors (mGluRs); another means being ionotropic receptors. Presently, eight mGluRs have been cloned and classified into three groups based on sequence homology, preferred signal transduction pathway and pharmacology. Group I of mGluRs includes mGluR1 and mGluR5, while Group II comprises mGluR2 and mGluR3 and Group III comprises mGlu4, 6, 7 and 8 receptors.

mGlu receptors have an essential role in normal brain functions, as well as in neurological, psychiatric, and neuromuscular disorders. mGlu5 receptors are located primarily postsynaptically and highly expressed in the limbic brain regions. mGlu5 receptors also are expressed in the thalamus, spinal cord, and vagal nerve systems, as well as peripherally in the skin on nerve endings and C fibers.

Ligands to the mGlu5 receptors have been shown to have promise for peripheral and central nervous system disorders. See e.g., G. Jaeschke et al., "mGlu5 receptor antagonists and their therapeutic potential," *Expert Opin. Ther. Patents*, 2008, 18, 2: 123-142. Yet some proffer that glutamate analogs targeting the orthosteric binding site may be limited by low brain penetration and insufficient selectivity with respect to the different mGluRs subtypes. Synthetic agonists may lead to continuous stimulation of the receptor since they are often designed to be metabolically stable. This continuous stimulation is not necessarily desirable, due to potential receptor desensitization issues. Also, with respect to receptor occupancy, synthetic antagonists may lead to prolonged blockade of receptor function, which may not be compatible with the kinetics of the pathology of a central nervous system disorder.

However, a more selective and controlled "fine-tuning" action on the mGlu5 receptor is feasible through allosteric modulation. See e.g., P. Bach et al., "Metabotropic glutamate receptor 5 modulators and their potential therapeutic applications," *Expert Opin. Ther. Patents*, 2007, 17, 4: 371-381. Allosteric modulation refers to binding by a modulator ligand to a site on a receptor that is different from the orthosteric primary substrate or ligand binding site. This ligand binding process results in conformational changes, which may profoundly influence the function of the protein (e.g., G protein-coupled receptors such as mGluRs, including mGluR5). Novel mGluR5 ligands that allosterically modulate the mGlu5 receptor may improve the therapeutic window of traditional central nervous system agents and/or the treatment of central nervous system disorders. The present invention is directed to these, and other important, ends.

SUMMARY OF THE INVENTION

The present invention provides compounds of formula (I):

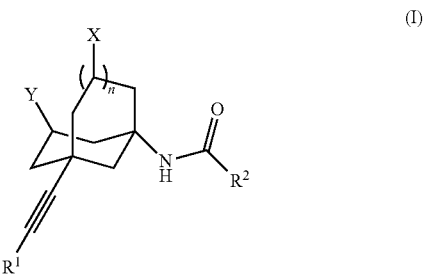

wherein:
$R^1$ and $R^2$ are independently aryl, heteroaryl, heterocyclyl which is optionally mono-, di-, or tri-substituted independently with alkyl, halogen, hydroxy, cyano, amino, alkylamino, dialkylamino, acyl, aryl, heteroaryl, heterocyclyl, cycloalkyl, ketocycloalkyl, alkoxy, hydroxylalkyl, trifluoromethyl; and
When n=0 and 1, X and Y are H; and
When n=1, both X and Y are bonds that are linked to —CH$_2$— to form a tricyclic adamantyl core; or a pharmaceutically acceptable salt thereof.

The term "alkyl", employed alone or as part of a group, is defined herein, unless otherwise stated, as either a straight-chain or branched saturated hydrocarbon of 1 to 8 carbon atoms. In some embodiments, the alkyl moiety contains 8, 7, 6, 5, 4, 3, 2 or 1 carbon atoms. Where the term "alkyl" appears herein without a carbon atom range it means a range of $C_1$-$C_8$. Where the term "alkyl" appears herein with a carbon range, it means an alkyl of any number within in the carbon range identified, such as a $C_1$-$C_3$alkyl means methyl, ethyl or propyl. Examples of saturated hydrocarbon alkyl moieties include, but are not limited to, chemical groups such as methyl, ethyl, n-propyl, isopropyl, n-butyl, tert-butyl, iso-butyl, sec-butyl, n-pentyl, n-hexyl, and the like.

The term "alkoxy", employed alone or in combination with other terms, is defined herein, unless otherwise stated, as —O-alkyl, where "alkyl" is as previously defined herein. Examples of alkoxy moieties include, but are not limited to, chemical groups such as methoxy, ethoxy, iso-propoxy, sec-butoxy, tert-butoxy, and homologs, isomers, and the like.

The term "hydroxyalkyl", employed alone or in combination with other terms, is defined herein, unless otherwise stated, as alkyl-OH, where "alkyl" is as previously defined herein. Non-limiting examples include —CH$_2$—OH, —(CH$_2$)$_2$—OH, —(CH$_2$)$_3$—OH, and the like.

As used herein, the term "cycloalkyl", employed alone or in combination with other terms, is defined herein, unless otherwise stated, as a cyclized alkyl group having from 3 to 8 ring carbon atoms, where "alkyl" is as defined herein. Examples of cycloalkyl moieties include, but are not limited to, chemical groups such as cyclopropyl, cyclobutyl, cyclopentyl, and cyclohexyl. Cycloalkyl also refers to cycloalkyl moieties where the cycloalkyl group is substituted by halogen, hydroxy, cyano, alkoxy, alkylamino, dialkylamino, alkylamide, dialkylamide, and the like.

As used herein, the term "ketocycloalkyl", employed alone or in combination with other terms, is defined herein, unless otherwise stated, as a cycloalkyl having a keto radical attached thereto, where "cycloalkyl" is as previously defined herein. Examples include cyclopentanone or cyclohexanone.

The terms "halo" or "halogen", employed alone or in combination with other terms, is defined herein, unless otherwise stated, as fluoro, chloro, bromo, or iodo.

The term "aryl", employed alone or in combination with other terms, is defined herein, which can be a single ring (monocyclic) or multiple rings (e.g., bicyclic, tricyclic, polycyclic) fused together or linked covalently. Any suitable ring position of the aryl moiety can be covalently linked to the defined chemical structure. Examples of aryl moieties include, but are not limited to, chemical groups such as phenyl, 1-naphthyl, 2-naphthyl, and the like. An aryl group can be unsubstituted or substituted as described herein.

The term "heteroaryl" employed alone or in combination with other terms, is defined herein, unless otherwise stated, as a monocyclic or polycyclic (fused together or linked covalently) aromatic hydrocarbon ring comprising one or more heteroatoms independently selected from nitrogen, oxygen, and sulfur. Examples of heteroaryl groups include, but are not limited to, pyridinyl, pyridazinyl, triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, oxazolyl, oxadiazolyl, 2-quinolinyl, 2-quinazolinyl, 3-phenyl-2-quinolinyl, imidazo[1,2-a]pyridinyl, benzimidazolyl, benzoxazolyl, and the like. A heteroaryl group can be unsubstituted or substituted as described herein.

The term "heterocyclyl" employed alone or in combination with other terms, is defined herein, unless otherwise stated, as a univalent group formed by removing a hydrogen atom from any ring atom of a heterocycle. In some embodiments, the heterocyclyl contains 1, 2, 3 or 4 heteroatoms selected independently from O, S and N.

The term "acyl" employed alone or in combination with other terms, is defined herein, unless otherwise stated, as groups of formula —C(O)-alkyl, where alkyl is as previously described herein; i.e., an alkylcarbonyl, such as formyl, acetyl and the like.

The term "aminoalkyl" employed alone or in combination with other terms, is defined herein, unless otherwise stated, as alkyl-amino, where the term "alkyl" is as previously defined herein and the term "amino" is —$NH_2$, —NH—, or —N<. Non-limiting examples include —$CH_3NH$—, $CH_3CH_2NH$—, ($C_1$-$C_3$alkyl)NH—, ($C_1$-$C_3$alkyl)$_2$N—, and the like.

The term "alkylamino" employed alone or in combination with other terms, is defined herein, unless otherwise stated, as amino-alkyl, where the term "alkyl" is as previously defined herein and the term "amino" is —$NH_2$, —NH—, or —N<. Non-limiting examples include —$NHCH_3$, —$NHCH_2CH_3$, —NH($C_1$-$C_3$alkyl), —N($C_1$-$C_3$alkyl)$_2$, and the like.

Another aspect of the present invention is a composition that comprises a pharmaceutically effective amount of a compound according to the present invention, and a pharmaceutically acceptable carrier or excipient.

A composition of the present invention may be adapted to any mode of administration, such as orally (including sublingually), to implants, parentally (including intravenous, intraperitoneal, intraarticularly and subcutaneous injections), rectally, intranasally, topically, ocularly (via eye drops), vaginally, and transdermally.

A compound of the present invention can be used either as a free base or in the form of a salt derived from pharmaceutically acceptable acids or bases. The salt includes without limitation the following: salts with inorganic acids, e.g., hydrochloric acid, hydrobromic acid, sulfuric acid, nitric acid, and phosphoric acid, and organic acids e.g., acetic acid, oxalic acid, citric acid, tartaric acid, succinic acid, maleic acid, benzoic acid, benzene sulfonic acid, fumaric acid, malic acid, methane sulfonic acid, pamoic acid, and para toluene sulfonic acid. Other salts include salts with alkali metals or alkaline earth metals, e.g., sodium, potassium, calcium and magnesium, or with organic bases, including quaternary ammonium salts. Further non-limiting examples of pharmaceutically acceptable inorganic and organic acid addition salts include those listed in [S. M. Berge et al., *J. Pharm. Sci.* 1977, 66, 1: 2, and G. S. Paulekuhn, et al., *J. Med. Chem.* 2007, 50, 26: 6665-6672].

When a compound of the present invention is employed as described above, it may be combined with one or more pharmaceutically acceptable excipients or carriers, e.g., solvents, diluents and the like. Such pharmaceutical preparations may be administered orally in such forms as tablets, capsules (including, e.g., time release and sustained release formulations), pills, lozenges, aerosols, dispersible powders, granules, solutions, suspensions (containing, e.g., a suspending agent, at, e.g., from about 0.05 to about 5% of suspending agent), syrups (containing, e.g., sugar or a sugar substitute such as aspartame, at, e.g., about 10 to about 50% sugar or sugar substitute), elixirs and the like, or parenterally in the form of sterile injectable solutions, suspensions or emulsions containing, e.g., from about 0.05 to about 5% suspending agent in an isotonic medium. Such preparations may contain, e.g., from about 25 to about 90% of the active ingredient in combination with the carrier, more customarily from about 5% and about 60% by weight. The effective dosage of an active ingredient (e.g., a compound or salt of the present invention and a prodrug or metabolite thereof) employed may vary depending on the particular compound, salt, prodrug or metabolite used, the mode of administration, age, weight, sex and medical condition of the patient, and the severity of the disease, disorder, condition, and/or system being treated. The selection of the appropriate administration and dosage form for an individual mammal will be apparent to those skilled in the art. Such determinations are routine to a physician, veterinarian or clinician of ordinary skill in the art (see e.g., *Harrison's Principles of Internal Medicine*, Anthony Fauci et al. (eds.) 14$^{th}$ ed. New York: McGraw Hill (1998)). Further, the dosage regimen may be adjusted to provide the optimal therapeutic response. For example, several divided doses may be administered daily or the dose may be proportionally reduced as indicated by the needs of the therapeutic situation.

Solid carriers, e.g., starch, lactose, dicalcium phosphate, microcrystalline cellulose, sucrose and kaolin, liquid carriers, e.g., sterile water, polyethylene glycols, glycerol, non-ionic surfactants and edible oils such as corn, peanut and sesame oils, may be employed as are appropriate to the nature of the active ingredient and the particular form of administration desired. Adjuvants customarily employed in the preparation of pharmaceutical compositions may be advantageously included. Non-limiting examples of adjuvants include flavoring agents, coloring agents, preserving agents, and antioxidants, such as vitamin E, ascorbic acid, BHT and BHA.

An active compound also may be administered parenterally or intraperitoneally. Solutions or suspensions of the active compound as a free base, neutral compound or pharmacologically acceptable salt can be prepared in water suitably mixed with a surfactant such as hydroxypropylcellulose. Dispersions also can be prepared in glycerol, liquid polyethylene glycols and mixtures thereof in oils. These preparations may contain a preservative to prevent the growth of microorganisms under ordinary conditions of storage and use.

It is understood by those practicing the art that some of the compounds of the present invention may contain one or more asymmetric centers, and thus may give rise to enantiomers and diastereomers. The present invention includes all stereoisomers including individual diastereomers and resolved, enantiomerically pure stereoisomers, as well as racemates, and all other variations of stereoisomers, and mixtures and pharmaceutically acceptable salts thereof which possess the indicated activity. Optical isomers may be obtained in pure form by customary procedures known to those skilled in the art, and include, but are not limited to, chiral chromatographic separations, diastereomeric salt formation, kinetic resolution, and asymmetric synthesis. It is also understood that this invention encompasses all possible regioisomers, endo-exo isomers, and mixtures thereof that possess the indicated activity. Such isomers can be obtained in pure form by customary procedures known to those skilled in the art, and include, but are not limited to, column chromatography, thin-layer chromatography, and high-performance liquid chromatography. It is understood by those practicing the art that some of the compounds of the present invention may be chiral due to hindered rotation, and give rise to atropisomers, which can be resolved and obtained in pure form by customary procedures known to those skilled in the art. It is further understood by those practicing the art that some of the compounds of the present invention include structural isomers, including tautomers.

Another aspect of the present invention is uses for, and methods for using, a compound of formula (I).

The invention is to be understood as embracing all simultaneous, sequential or separate use of any combination of the compounds of formula (I) with any pharmaceutical composition useful in the uses or methods described herein.

In some embodiments, the use or method includes administering an effective amount of a compound of formula (I), or salt thereof. In some embodiments, the use or method includes administering a therapeutically effective amount of a compound described herein, or salt thereof.

In some embodiments, the method includes administering an effective amount of a combination of two or more of the compounds described herein, or salts thereof. It is specifically intended that the phrases "combination of two or more of the compounds described herein, or salts thereof," or "at least one compound as described herein, or a pharmaceutically acceptable salt thereof," or similar language describing specific compounds, includes the administration of such compounds in any proportion and combination of salt, neutral or free base forms; i.e., includes the administration of such compounds each in the base form, each in the neutral form or each in the salt form, or one or more in the base form and one or more in the neutral form, or one or more in the base form and one or more in the salt form, or one or more in the neutral form and one or more in the salt form, in any proportion of the neutral and/or basic compounds and/or salts.

As used herein, the phrase "effective amount" when applied to a compound of the invention, is intended to denote an amount sufficient to cause an intended biological effect. The phrase "therapeutically effective amount" when applied to a compound of the invention is intended to denote an amount of the compound that is sufficient to ameliorate, palliate, stabilize, reverse, slow or delay the progression of a disorder or disease state, or of a symptom of the disorder or disease. In some embodiments, the method of the present invention provides for administration of combinations of compounds. In such instances, the "effective amount" is the amount of the combination sufficient to cause the intended biological effect.

The term "treatment" or "treating" as used herein means curing, ameliorating or reversing the progress of a disease or disorder, or ameliorating or reversing one or more symptoms or side effects of such disease or disorder. "Treatment" or "treating", as used herein, also means to inhibit or block, as in retard, arrest, restrain, impede or obstruct, the progress of a system, condition or state of a disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of a disease or disorder state, amelioration or palliation of a disease or disorder state, and remission of a disease or disorder, whether partial or total, detectable or undetectable.

The term "prevent" or "preventing" as used herein means to keep from happening or existing. The term "administering" as used herein refers to either directly administering a compound of the present invention, or administering a prodrug, derivative, or analog of same, that will form an effective amount of the compound within a mammal.

In some embodiments, the method is a method of treating a disease or disorder, or a symptom thereof, the method comprising administering a therapeutically effective amount of at least one compound of formula (I) or a pharmaceutically acceptable salt thereof to a mammal in need thereof, wherein the disease or disorder is a central nervous system disease or disorder, such as those described herein and the like.

In some embodiments, the use of a compound of formula (I) is for the preparation of a medicament for the treatment of a disease or disorder, or a symptom thereof, wherein the disease or disorder is a central nervous system disease or disorder, such as those described herein and the like. In some embodiments, the use of a compound of formula (I) is for the preparation of a medicament for improvement of a disease or disorder, or a symptom thereof, wherein the disease or disorder is a central nervous system disease or disorder, such as those described herein and the like.

In some embodiments, the compound of formula (I) is for use in treating a disease or disorder, or a symptom thereof, wherein the disease or disorder is a central nervous system disease or disorder, such as those described herein and the like. In some embodiments, the use of a compound of formula (I) is for improvement of a disease or disorder, or a symptom thereof, wherein the disease or disorder is a central nervous system disease or disorder, such as those described herein and the like.

A compound of the present invention can allosterically modulate the mGlu5 receptor. An allosteric modulator that enhances or potentiates the affinity of an orthosteric ligand for the mGluR5 receptor and/or enhances or potentiates an orthosteric agonist's efficacy is an allosteric enhancer (or potentiator) or positive allosteric modulator (PAM). See e.g., May, L. T. *Annu. Rev. Pharmacal. Toxicol.* 2007, 47, 1-51. An allosteric modulator that reduces or diminishes the affinity of all orthosteric ligand for the mGluR5 receptor and/or reduces or diminishes an orthosteric agonist's efficacy is an allosteric antagonist (or inhibitor) or negative allosteric modulator (NAM). Id.

In some embodiments, the mammal is a human.

In some embodiments, the use or method comprises administering an effective amount, or a therapeutically effective amount, of a compound of formula (I) to a human in need thereof.

In some embodiments, the central nervous system disease or disorder is a cognitive, neurodegenerative, psychiatric or neurological disease or disorder. In some embodiments, the disease or disorder is selected from a group consisting of a mood disorder, an anxiety, a schizophrenia (including schizoaffective disorders), Alzheimer's disease, Parkinson's disease, multiple sclerosis, Huntington's disease amyotrophic lateral sclerosis, Creutzfeld-Jakob disease, a trauma-induced neurodegeneration, AIDS-induced encephalopathy, another infection-related encephalopathy (i.e., a non-AIDS-induced encephalopathy), Fragile X syndrome, an autism spectrum disorder, and a combination thereof.

As used herein, the phrase "mood disorder" refers to any of several psychological disorders characterized by abnormalities of emotional state, such as, without limitation, bipolar disorders, depressive disorders, cyclothymic disorders, dysthymic disorders, mood disorders due to a general medical condition, mood disorders not otherwise specified and substance-induced mood disorders; and as characterized by the *Diagnostic and Statistical Manual of Mental Disorders*, Fourth Edition (DSM-IV) (American Psychiatric Association: Arlington, Va., 1994).

As used herein, the phrase "autism spectrum disorder" (ASD) refers to a disorder that causes severe and pervasive impairment in thinking, feeling, language, and the ability to relate to others, which is often first diagnosed in early childhood and range from a severe form, called autistic disorder ("classic" autism), through pervasive development disorder not otherwise specified (PDD-NOS), to a much milder form, Asperger syndrome. The phrase, as used herein, also includes Rett syndrome and childhood disintegrative disorder, and as used herein, is synonymous with the phrase, "pervasive developmental disorders" (PDDs).

In some embodiments, the mood disorder is a depression (i.e., a depressive disorder). In some such embodiments, the depression is selected from the group consisting of atypical depression, bipolar depression, unipolar depression, major depression, endogenous depression (i.e., acute depression with no obvious cause), involutional depression (i.e., depression that occurs in mid-life or the elderly), reactive depression (i.e., depression caused by an obvious traumatic life episode), postpartum depression, primary depression (i.e., depression that has no obvious physical or psychological cause such as a medical illness or disorder), psychotic depression, and secondary depression (i.e., depression that seems to be caused by some other underlying condition such another medical illness or disorder).

In some embodiments, the anxiety disease or disorder is selected from a group comprising generalized anxiety disorder, panic anxiety, obsessive compulsive disorder, social phobia, performance anxiety, post-traumatic stress disorder, acute stress reaction, an adjustment disorder, a hypochondriacal disorder, separation anxiety disorder, agoraphobia, a specific phobia, anxiety disorder due to general medical condition, substance-induced anxiety disorder, alcohol withdrawal-induced anxiety, and a combination thereof.

In some embodiments, the central nervous system disease or disorder is a seizure disease or disorder. In some embodiments, the seizure disease or disorder is selected from the group consisting of a convulsion, epilepsy, status epilepticus, and a combination thereof.

In some embodiments, the central nervous system disease or disorder is a pain disease or disorder selected from the group consisting of inflammatory pain, neuropathic pain and migraine pain. In some embodiments, the neuropathic pain or migraine pain disease or disorder is selected from the group consisting of allodynia, hyperalgesic pain, phantom pain, neuropathic pain related to diabetic neuropathy, neuropathic pain related to migraine, and a combination thereof.

In some embodiments, the central nervous system disease or disorder is a neuronal hyperexcitation state disease or disorder. In some embodiments, the neuronal hyperexcitation state disease or disorder is a neuronal hyperexcitation state in medicament withdrawal, a neuronal hyperexcitation state in intoxication, or a combination thereof.

In some embodiments, at least one symptom of the cognitive neurodegenerative, psychiatric or neurological disease or disorder is treated.

In some embodiments, the cognitive, neurodegenerative, psychiatric or neurological disease or disorder is a depression. In some such embodiments, the at least one symptom of the depression is depressed feeling, depressed mood, loss of interest or pleasure in some or all activities, changes in appetite, changes in weight, changes in sleep patterns, lack of energy, fatigue, low self esteem, diminished capacity for thinking, concentration, or decisiveness, feelings of hopelessness or worthlessness, psychomotor agitation or retardation, self-reproach, inappropriate guilt, frequent thoughts of death or suicide, plans or attempts to commit suicide, or a combination thereof.

In some embodiments, the cognitive, neurodegenerative, psychiatric or neurological disease or disorder is an anxiety. In some such embodiments, the at least one symptom of anxiety is apprehension, fear, trembling, muscle aches, insomnia, abdominal upsets, dizziness, irritability, persistent, recurring thoughts, compulsions, heart palpitations, chest pain, chest discomfort, sweating, tingling sensations, feeling of choking, fear of losing control, flashbacks, nightmares, intrusive thoughts, intrusive recollections, avoidance behaviors, emotional numbing, an inability to sleep, anxious feelings, overactive startle response, hypervigilance, outbursts of anger, faintness, blushing, profuse sweating, or a combination thereof.

In some embodiments, the cognitive, neurodegenerative, psychiatric or neurological disease or disorder is schizophrenia. In some such embodiments, the at least one symptom of schizophrenia is a positive symptom selected from the group consisting of hallucination, delusion, paranoia, and a combination thereof. In some such embodiments, the symptom of schizophrenia is a negative symptom selected from the group consisting of social withdrawal, flat affect, anhedonia, decreased motivation, and a combination thereof. In some such embodiments, the symptom of schizophrenia is a cognitive symptom selected from the group consisting of severe deficit in attention, severe deficit in object naming, severe deficit in working memory, severe deficit in long-term memory storage, severe deficit in executive functioning, a slowing of information processing, a slowing of neural activity, long term depression, and a combination thereof.

In some embodiments, the cognitive, neurodegenerative, psychiatric or neurological disease or disorder is Parkinson's disease. In some such embodiments, the at least one symptom of Parkinson's disease is levodopa-induced dyskinesia, poor balance, Parkinsonian gait, bradykinesia, rigidity, tremor, change in speech, loss of facial expression, micrographia, difficulty swallowing, drooling, pain, dementia, confusion, a sleep disturbance, constipation, a skin problem, depression, fear, anxiety, difficulty with memory, slowed thinking, sexual dysfunction, an urinary problem, fatigue, aching, loss of energy, or a combination thereof.

In some embodiments, the cognitive, neurodegenerative, psychiatric or neurological disease or disorder is Alzheimer's disease. In some such embodiments, the at least one symptom of Alzheimer's disease is impairment in memory, impairment in attention, impairment in judgment, impairment in decision-making, impairment in orientation to physical surroundings, language impairment, impairment in speed-dependent activities, impairment in abstract reasoning, impairment in visuospatial abilities, impairment in executive functioning, impairment in behavioral disturbances, disinterest and passivity, apathy, inappropriate dressing, poor self care, agitation, violent outburst, aggression, depression, anxiety, hallucination, delusion, change in personality, change in mood, dementia, or a combination thereof.

In some embodiments, the cognitive, neurodegenerative, psychiatric or neurological disease or disorder is Huntington's disease (as known as Huntington's disorder and including Huntington's chorea). In some such embodiments, the at least one symptom of Huntington's chorea is, without limitation, Personality changes, such as irritability, anger, depression or a loss of interest, decreased cognitive abilities, dementia, balance problems, coordination problems, clumsiness, involuntary facial movements such as grimacing, seizures, tremors, muscle rigidity, slow movements, sudden jerky and/or involuntary movements, jerky and/or rapid eye movements, swallowing problems, and hesitant, halting and/or slurred speech.

In some embodiments, the cognitive, neurodegenerative, psychiatric or neurological disease or disorder is multiple sclerosis. In some such embodiments, the at least one symptom of multiple sclerosis is optic neuritis blurred vision, eye pain, loss of color vision, blindness, diplopia double vision, nystagmus jerky eye movements, ocular dysmetria, constant under- or overshooting eye movements, internuclear ophthalmoplegia, nystagmus, diplopia, movement and sound phosphenes, diplopia, afferent pupillary defect, motor paresis, monoparesis, paraparesis, hemiparesis, quadraparesis plegia, paraplegia, hemiplegia, tetraplegia, quadraplegia, spasticity, dysarthria, muscle atrophy, spasms, cramps, hypotonia, clonus, myoclonus, myokymia, restless leg syndrome, footdrop dysfunctional reflexes (msrs, babinski's, hoffman's, chaddock's), paraesthesia, anaesthesia, neuralgia, neuropathic pain, neurogenic pain, l'hermitte's, proprioceptive dysfunction, trigeminal neuralgia, ataxia, intention tremor, dysmetria, vestibular ataxia, vertigo, speech ataxia, dystonia, dysdiadochokinesia, frequent micturation, bladder spasticity, flaccid bladder, detrusor-sphincter dyssynergia, erectile dysfunction, anorgasmy, retrograde ejaculation, frigidity, constipation, fecal urgency, depression, cognitive dysfunction, dementia, mood swings, emotional lability, euphoria, bipolar syndrome, anxiety, aphasia, dysphasia, fatigue, uhthoffs symptom, gastroesophageal reflux, a sleeping disorder, or a combination thereof.

The present invention further provides uses and methods for treating gastroesophageal reflux. The present invention also provides uses of a compound of formula (I) for the preparation of medicament for the treatment of gastroesophageal reflux. In some embodiments, the uses and the methods comprise administering the compound as described herein.

The present invention further provides a use and a method for treating alcohol and drug dependence. The present invention also provides uses of a compound of formula (I) for the preparation of medicament for the treatment of alcohol dependence. In some embodiments, the uses and the methods comprise administering the compound as described herein.

Another aspect of the present invention is a process for producing the compounds of the present invention.

BRIEF DESCRIPTION OF THE DRAWING

FIG. 1 shows that 5-(pyridin-2-ylethynyl)bicyclo[3.2.1] oct-1-ylamine (2.0 g) was resolved on a SFC preparative separation system into two enantiomers.

PREPARATION OF THE COMPOUNDS OF THE PRESENT INVENTION

The compounds of the present invention may be prepared, without limitation, according to the general method outlined below. For example, Schemes 1 to 4 that follow are intended as an illustration of some embodiments of the invention and no limitation of the present invention is implied because of them.

The following defines acronyms as used herein unless specified otherwise in a particular instance.

Boc=tert-butyloxycarbonyl; BOP=Benzotriazole-1-yl-oxy-tris-(dimethylamino)-phosphonium hexafluorophosphate, CAS No. 56602-33-6; Cbz=carboxybenzyl; DCM=Dichloromethane or Methylene chloride, CAS No. 75-09-2; DIEA=N,N-diisopropylethylamine, CAS No. 7087-68-5; DMA=N,N-dimethylacetamide, CAS No. 127-19-5; DMAP=4-dimethylaminopyridine, CAS No. 1122-58-3; DMC=2-Chloro-1,3-dimethylimidazolinium chloride, CAS No. 37091-73-9; DMF=N,N-dimethylformamide, CAS No. 68-12-2; DMPU=1,3-Dimethyl-3,4,5,6-tetrahydro-2 (1H)-pyrimidinone, CAS No. 7226-23-5; DMSO=Dimethyl sulfoxide, CAS No. 67-68-5; DPPA=Diphenylphosphoryl azide, CAS No. 26386-88-9; EDAC=EDC=1-Ethyl-3-(3-dimethyllaminopropyl)carbodiimide; EDCI N-Ethyl-N'-(3-dimethylaminopropyl)carbodiimide hydrochloride, CAS No. 93128-40-6; HATU=2-(1H-7-Azabenzotriazol-1-yl)-1,1,3,3-tetramethyl uronium hexafluorophosphate Methanaminium, CAS No. 148893-10-1; HBTU=2-(1H-Benzotriazole-1-yl)-1,1,3,3-Tetramethyluronium hexafluorophosphate, CAS No. 94790-37-1; MTBE=Methyl t-butyl ether, CAS No. 145288-29-5; NBS=N-Bromosuccinimide, CAS No. 128-08-5; NMP=N-Methyl-pyrrolidone, CAS No. 872-50-4; PCC=Pyridinium chlorochromate; PyBOP=Benzotriazol-1-yl-oxytripyrrolidinophosphonium hexafluoro phosphate, CAS No. 128625-52-5; rt=room temperature; RT=LC-MS retention time; TBTU=O-(Benzotriazol-1-yl)-N,N,N',N'-tetramethyluronium tetrafluoroborate, CAS No. 125700-67-6; TEA=Triethyl amine, CAS No. 121-44-8; TFA=Trifluoroacetic acid, CAS No. 76-05-1; THF=Tetrahydrofuran, CAS No. 109-99-9

A compound of formula (I-a) can be prepared via the process outlined in Scheme 1. Esterification of commercially available cyclohexane-1,3-dicarboxylic acid 1 under conditions such as in methanol in the presence of chlorotrimethylsilane affords ester 2. Alkylation of compound 2 with 1-bromo-2-chloroethane or 1-bromo-3-chloropropane in the presence of base produces bicyclic compound 3. Saponification of 3 under customary conditions gives carboxylic acid 4, which is converted to Cbz-protected amine 5 via a standard Curtius rearrangement, followed by the treatment with benzyl alcohol. Reduction of compound 5 under customary conditions yields primary alcohol 6. Removal of Cbz protecting group of compound 6 produces amine 7, which is then converted to amide 8 under customary amidation conditions by reading with $R^2CO_2H$. Oxidation of compound 8 under customary conditions affords aldehyde 9, which is then converted to alkyne 10 using customary conditions such as a reaction with dimethyl (1-diazo-2-oxopropyl)phosphonate in the presence of base $K_2CO_3$. Reaction of alkyne 10 with aryl halide or heteroaryl halide $R^1X$ via Sonogashira reaction affords a compound of formula (I-a).

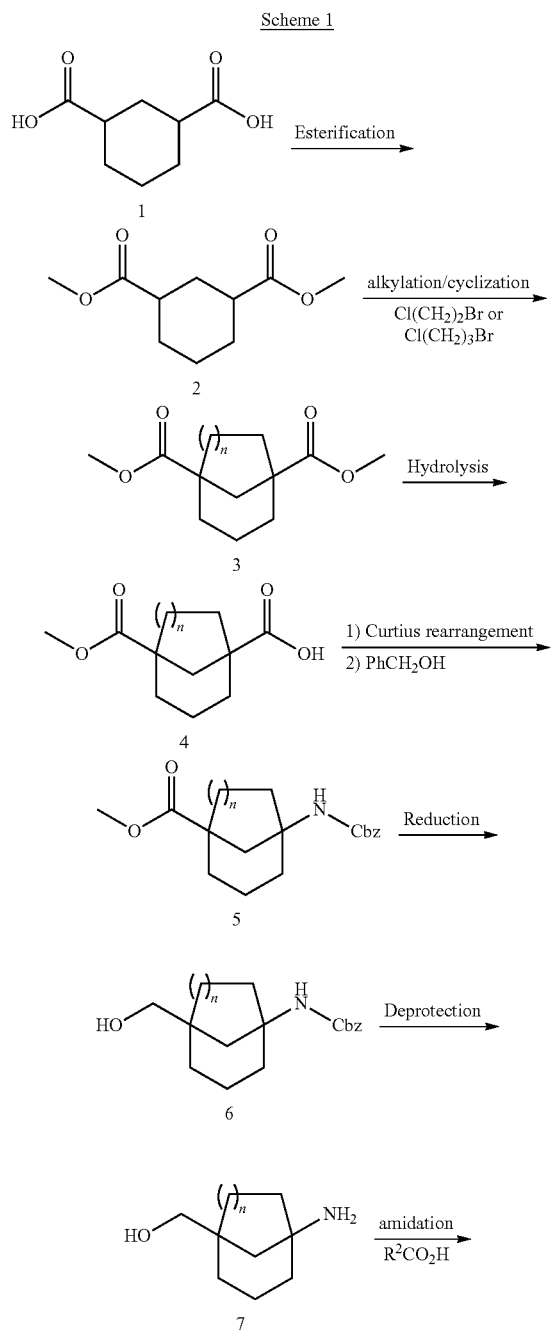

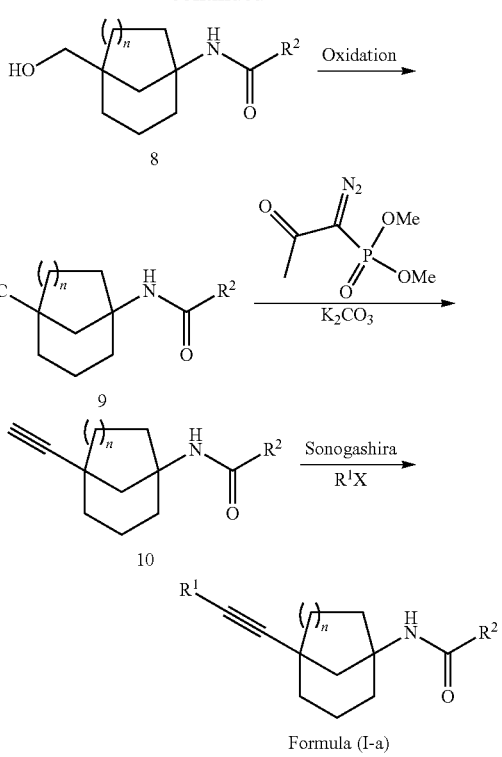

A compound of formula (I-a) can also be prepared via the process outlined in Scheme 2.

Removal of the Cbz protecting group of compound 5 gives amine 11, which is then converted to Boc protected compound 12. Reduction of the ester group of 12 under customary conditions affords primary alcohol 13. Oxidation of compound 13 under customary conditions yields aldehyde 14, which is then converted to alkyne 15 using customary conditions such as a reaction with dimethyl (1-diazo-2-oxopropyl) phosphonate in the presence of base $K_2CO_3$. Reaction of alkyne 15 with an halide or heteroaryl halide $R^1X$ via standard Sonogashira reaction produces compound 16. Removal of the Boc protecting group of compound 16 gives amine 17, which is then converted to a compound of formula (I-a) via amidation with $R^2CO_2H$ or $R^2COCl$ under customary conditions. Amidation of amine 11 with $R^2CO_2H$ or $R^2COCl$ produces compound 19. Reduction of the ester group of 19 under customary conditions affords primary alcohol 8, which was then converted to a compound of formula (I-a) via compounds 8, 9 and 10 as described in Scheme 1. Removal of the Boc protecting group of compound 15 gives amine 18. Amidation of 18 with $R^2CO_2H$ or $R^2COCl$ yields compound 10. Reaction of alkyne 10 with aryl halide or heteroaryl halide $R^1X$ via Sonogashira reaction affords a compound of formula (I-a).

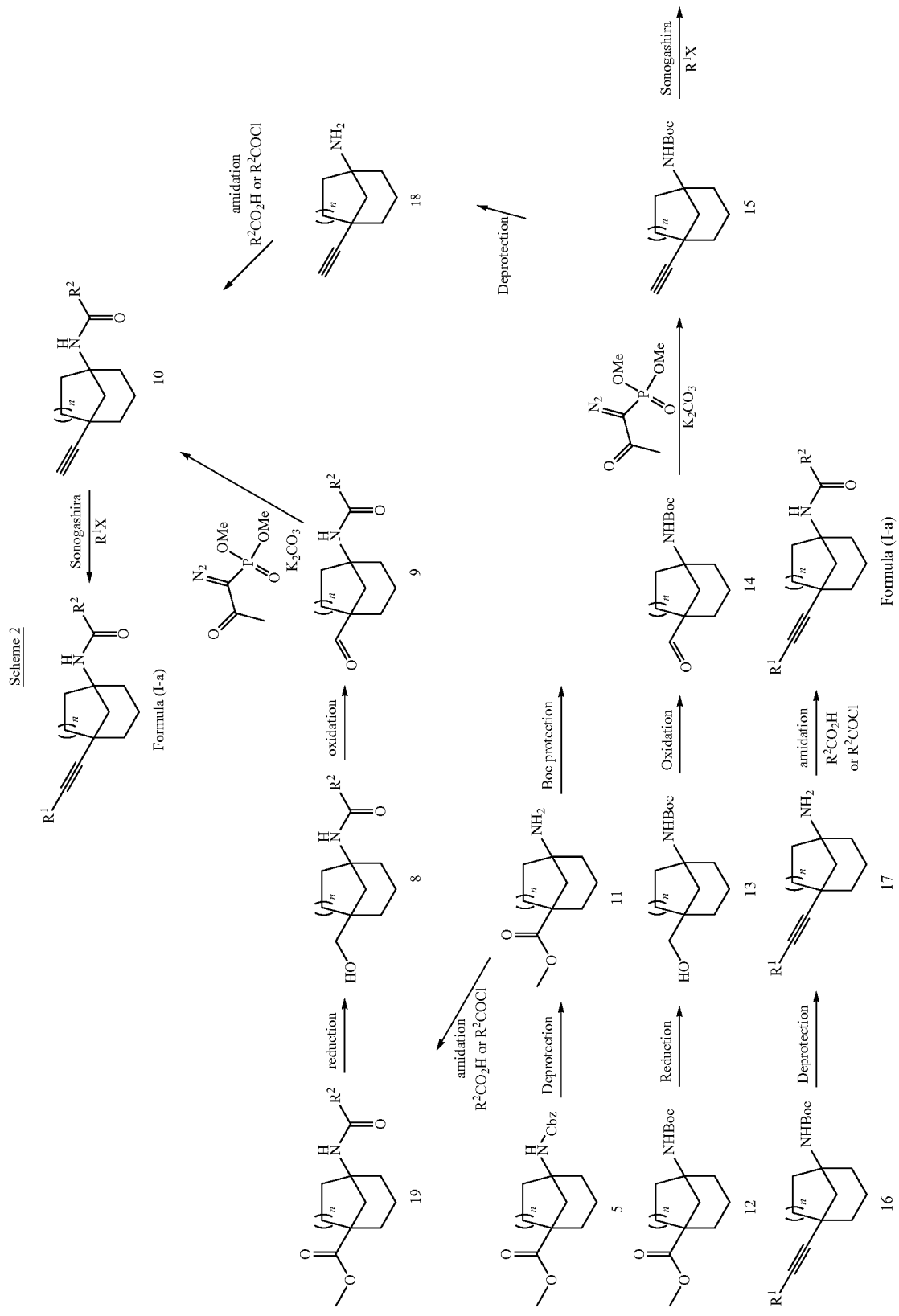

A compound of formula (I-b) can be prepared via the process outlined in Scheme 3. Amidation of compound 20 (Hermogenes N. J. et al.; U.S. Pat. No. 7,947,680 B2) with R²CO₂H or R²COCl under customary conditions gives amide 21. Reduction of compound 21 under customary conditions yields alcohol 22. Oxidation of alcohol 22 under customary conditions produces aldehyde 23, which is then converted to alkyne 24 under customary conditions such as reaction with dimethyl (1-diazo-2-oxopropyl)phosphonate in the presence of base K₂CO₃. Reaction of alkyne 24 with an halide or heteroaryl halide R¹X via Sonogashira reaction affords a compound of formula (I-b).

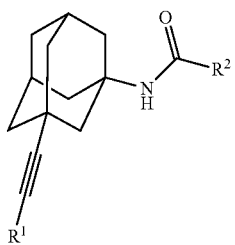

Formula (I-b)

A compound of formula (I-b) can also be prepared via the process outlined in Scheme 4. Boc protection of compound 20 under customary conditions gives compound 25. Reduction of 25 under customary conditions affords alcohol 26, which is then oxidized to aldehyde 27 using standard conditions. Reaction of 27 with dimethyl (1-diazo-2-oxopropyl) phosphonate in the presence of base K₂CO₃ produces alkyne 28. Sonogashira reaction of alkyne 28 with aryl halide or heteroaryl halide R¹X via customary conditions yields compound 29. Removal of Boc of compound 29 under customary conditions gives amine 30, which is then converted to a compound of formula (I-b) by standard amidation reaction with R²CO₂H or R²COCl.

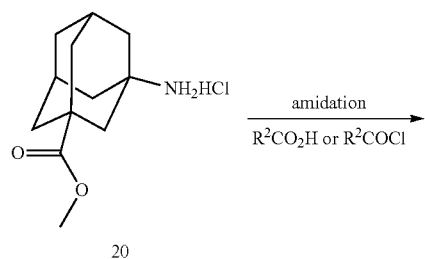

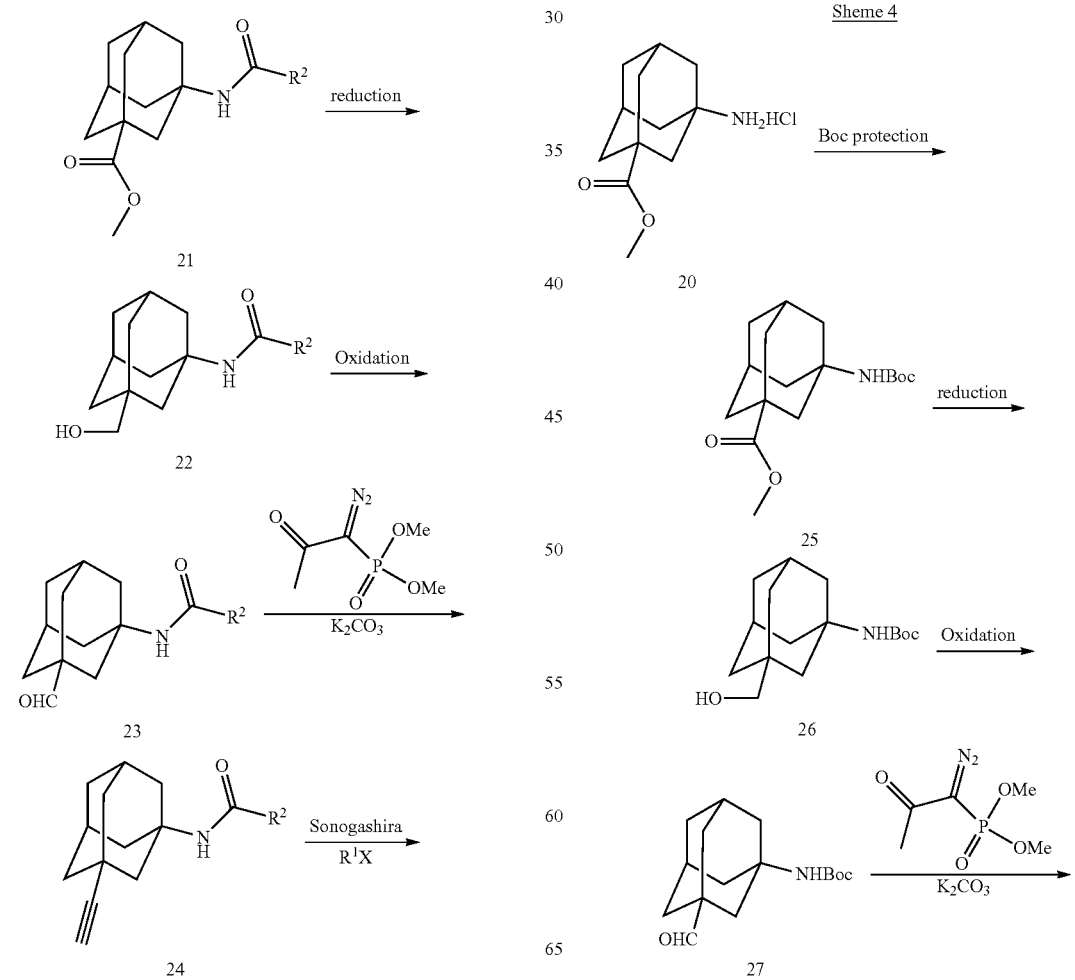

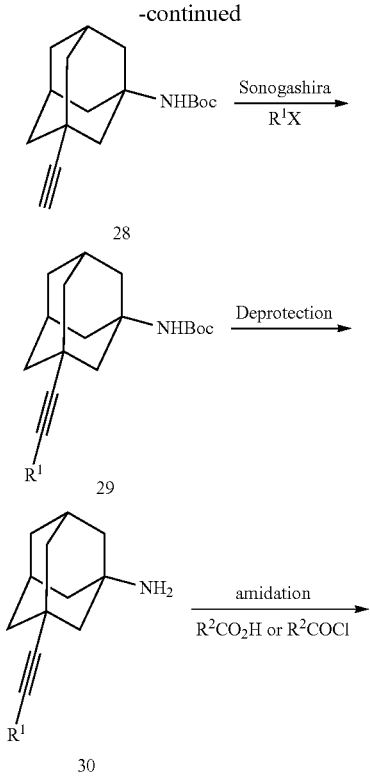

Experimental Section

1. General Methods

Unless specifically stated otherwise, the experimental procedures were performed under the following conditions. All operations were carried out at room temperature (about 18° C. to about 25° C.) under nitrogen atmosphere. Evaporation of solvent was carried out using a rotary evaporator under reduced pressure or in a high performance solvent evaporation system HT-4X (Genevac Inc., Valley Cottage, N.Y., USA). Microwave oven used is an apparatus from Biotage (Initiator). The course of the reaction was followed by thin layer chromatography (TLC) or liquid chromatography-mass spectrometry (LC-MS), and reaction times are given for illustration only. Silica gel chromatography was carried out on a CombiFash® system (Teledyne Isco, Inc., Lincoln, Nebr., USA) with pre-packed silica gel cartridge or performed on Merck silica gel 60 (230-400 mesh). The structure and purity of all final products was assured by at least one of the following analytical methods: nuclear magnetic resonance (NMR) and LC-MS. NMR spectra was recorded on a Bruker Avance™ 300 spectrometer (Bruker BioSpin Corp., Billerica, Mass., USA) or a Varian UNITY INOVA® 400 (Varian, Inc., Palo Alto, Calif., USA) or Bruker ADVANCE III 500 MHz UltraShield-Plus™ Digital NMR spectrometer using the indicated solvent. Chemical shift (□) is given in parts per million (ppm) relative to tetramethylsilane (TMS) as an internal standard. Coupling constants (J) are expressed in hertz (Hz), and conventional abbreviations used for signal shape are: s=singlet; d=doublet; t=triplet; m=multiplet; br=broad; etc. Unless stated otherwise, mass spectra were obtained using electrospray ionization (ESMS) via a Micromass® Platform II system or a Quattro micro system (both from Waters Corp., Milford, Mass., USA) or 1200RRLC/ 6164 SQ system (Agilent technologies, Santa Clara, Calif., USA), and $(M+H)^+$ is reported.

2. Preparation of Intermediates of the Invention

Intermediate 1: N-(5-ethynylbicyclo[3.2.1]octan-1-yl)pyrazine-2-carboxamide

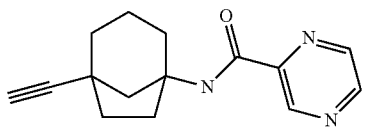 [SMILES: C#CC12CCCC(NC(=O)c3cnccn3)(CC1)C2]

Intermediate 1 was prepared from commercially available cyclohexane-1,3-dicarboxylic acid via the process of Scheme 1, supra, as follows:

Step 1: Dimethyl cyclohexane-1,3-dicarboxylate

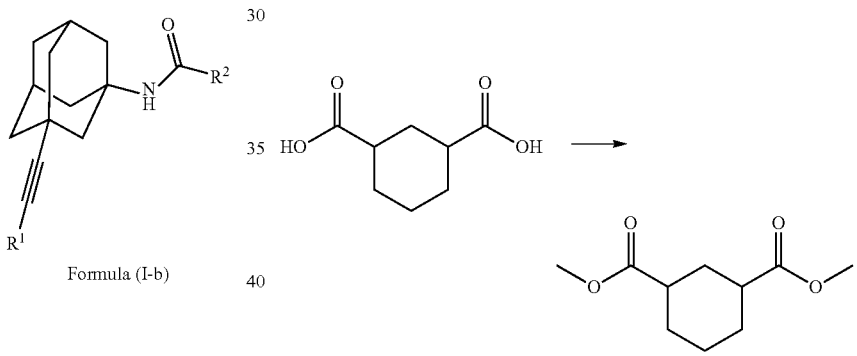

To a solution of cyclohexane-1,3-dicarboxylic acid (25 g, 0.145 mol) in MeOH (250 mL) was added concentrated $H_2SO_4$ (5 mL) and the reaction solution was refluxed overnight. After cooled to room temperature, the reaction mixture was concentrated under reduced pressure and the residue was dissolved in ethyl acetate (500 mL). The resulting solution was washed with Sat. $Na_2CO_3$ (2×300 mL) and brine (100 mL), dried over $MgSO_4$ and concentrated under reduced pressure to give 27.4 g (94%) of the title compound, dimethyl cyclohexane-1,3-dicarboxylate, as a light yellow oil. ESI-MS m/z: 201 $(M+H)^+$.

Step 2: Dimethyl 1-(3-chloropropyl)cyclohexane-1,3-dicarboxylate

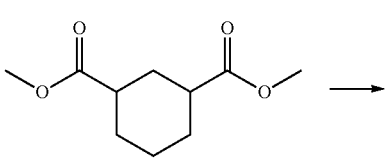

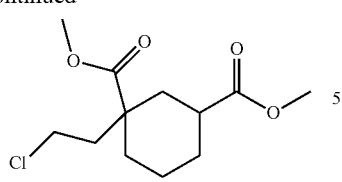

To a pre-cooled (−78° C.) solution of lithium diisopropylamide (94 mL, 188 mmol) in anhydrous THF (250 mL) was added DMPU (76 g, 600 mmol) dropwise, not allowing the temperature to exceed −65° C., followed by an addition of a solution of dimethyl cyclohexane-1,3-dicarboxylate (25 g, 125 mmol) in anhydrous THF (50 mL) at −78° C. over 20 min. After stirring at −78° C. for one hour, 1-bromo-2-chloroethane (25 g, 175 mmol) was added and the reaction was slowly warmed up to room temperature overnight. After quenched with saturated $NH_4Cl$ (100 mL), the reaction mixture was concentrated under reduced pressure and then diluted with water (200 mL). The resulting aqueous mixture was extracted with DCM (4×100 mL) and the combined organic phase was washed with water (100 mL) and brine (100 mL), dried over $Na_2SO_4$ and concentrated under reduced pressure. The resulting residue was purified by column chromatography (silica gel, petroleum ether/ethyl acetate=20/1) to afford 23 g (70%) of the title compound, dimethyl 1-(3-chloropropyl)cyclohexane-1,3-dicarboxylate as a yellow oil. ESI-MS m/z: 263 $(M+H)^+$.

Step 3: Dimethyl bicyclo[3.3.1]nonane-1,5-dicarboxylate

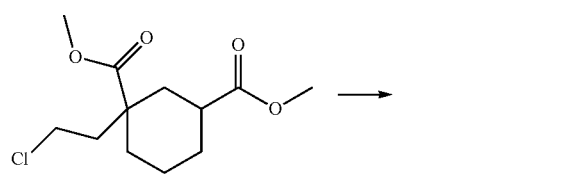

To a pre-cooled (−78° C.) solution of lithium diisopropylamide (86 mL, 172 mmol) in tetrahydrofuran (400 mL) was added DMPU (70.4 g, 550 mol) dropwise, followed by an addition of dimethyl 1-(3-chloropropyl)cyclohexane-1,3-dicarboxylate (30 g, 114.5 mmol) in anhydrous THF (50 mL) within 20 min. After stirring at −78° C. for 30 min, the reaction was allowed to warm up to room temperature over a period of 1.5 h, and then quenched with saturated $NH_4Cl$ (100 mL). The mixture was concentrated under reduced pressure and then diluted with water (300 mL). The resulting aqueous mixture was extracted with DCM (4×100 mL) and the combined organic layer was washed with water (100 mL) and brine (100 mL), dried over $Na_2SO_4$ and concentrated under reduced pressure. The residue was purified by column chromatography (silica gel, petroleum ether/ethyl acetate=30/1) to afford 15.5 g (60%) of the title compound, dimethyl bicyclo[3.3.1]nonane-1,5-dicarboxylate as a light yellow oil. ESI-MS m/z: 227 $(M+H)^+$.

Step 4: 5-(Methoxycarbonyl)bicyclo[3.3.1]nonane-1-carboxylic acid

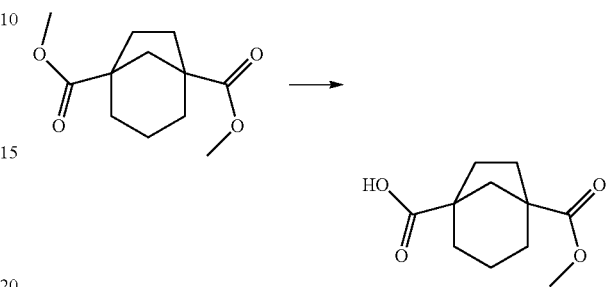

A solution of dimethyl bicyclo[3.3.1]nonane-1,5-dicarboxylate (20 g, 88 mmol) and $Ba(OH)_2 \cdot 8H_2O$ (13.95 g, 44 mmol) in ethanol (200 mL) and $H_2O$ (40 mL) was refluxed overnight. After cooled to rt, the reaction was concentrated under reduced pressure. The resulting residue was diluted with water (100 mL) and the aqueous mixture was extracted with diethyl ether (3×200 mL). The combined organic phase was washed with brine (100 mL), dried over $Na_2SO_4$ and concentrated under reduced pressure to recover dimethyl bicyclo[3.3.1]nonane-1,5-dicarboxylate as orange oil. The aqueous phase was adjusted to pH=1-2 with 2N HCl and extracted with dichloromethane (3×100 mL). The combined organic phase was washed with brine, dried over $Na_2SO_4$ and concentrated under reduced pressure to afford crude 13 g (70%, mixed with di-acid) of the title compound, 5-(methoxycarbonyl)bicyclo[3.3.1]nonane-1-carboxylic acid as a white solid. ESI-MS m/z: 213 $(M+H)^+$. It was used in the next step without further purification.

Step 5: Methyl 5-(benzyloxycarbonylamino)bicyclo[3.2.1]octane-1-carboxylate

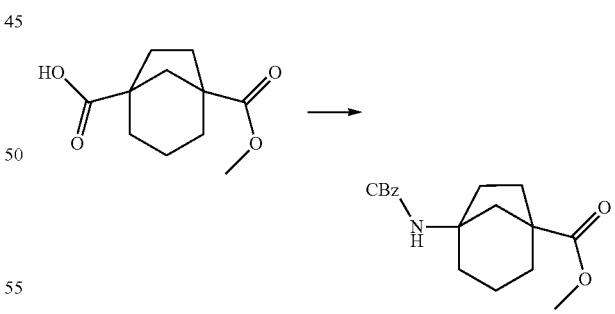

A solution of 5-(methoxycarbonyl)bicyclo[3.3.1]nonane-1-carboxylic acid (19 g, 90 mmol), diphenylphosphonic azide (29.6 g, 107.5 mmol) and TEA (36.4 mL, 360 mmol) in toluene (200 mL) was stirred at room temperature for one hour, then refluxed for three hours. Benzyl alcohol (11.6 g, 107.5 mmol) was added and the solution was continued to reflux overnight. After cooled to room temperature, the reaction was concentrated under reduced pressure. The resulting residue was purified by column chromatography (silica gel, petroleum ether/ethyl acetate=51) to afford 10 g (containing some BnOH) of the title compound, methyl 5-(benzyloxycarbonylamino)bicyclo[3.2.1]octane-1-carboxylate as a brown oil. ESI-MS m/z: 318 (M+H)⁺.

Step 6: N-(5-(hydroxymethyl)bicyclo[3.2.1]octan-1-yl)acetamide

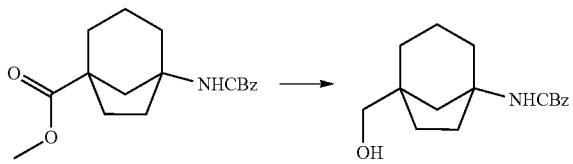

To a stirred solution of methyl 5-(benzyloxycarbonylamino)bicyclo[3.2.1]octane-1-carboxylate (1.0 g, 3.15 mmol) in THF (20 mL) at 0° C. was added LiBH₄ (2M in THF, 3 mL, 6 mmol) dropwise under N₂. After stirring at 0° C. for 30 min, the reaction was allowed to warm up to room temperature overnight. The reaction was quenched with Sat. NH₄Cl and resulting mixture was extracted with ethyl acetate (3×20 mL). Combined organic phase was washed with brine, dried over Na₂SO₄ and concentrated under reduced pressure to afford a residue, which was purified by column chromatography (silica gel, petroleum ether/ethyl acetate=3/1) to give 750 mg (81%) of the title compound, N-(5-(hydroxymethyl)bicyclo[3.2.1]octan-1-yl)acetamide as a colorless oil. ESI-MS m/z: 290 (M+H)⁺

Step 7: (5-Aminobicyclo[3.2.1]octan-1-yl)methanol

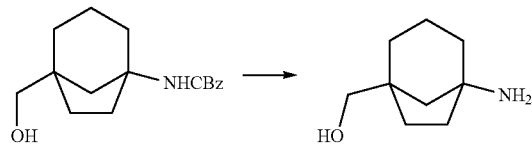

To a solution of N-(5-(hydroxymethyl)bicyclo[3.2.1]octan-1-yl)acetamide (3.70 g, 12.8 mmol) in ethanol (30 mL) was added Pd/C (371 mg) and the reaction mixture was hydrogenated at room temperature (1 atm) overnight. The catalyst was then removed by filtration and the filtrate was concentrated under reduced pressure to afford 1.88 g (95%) of the title compound, (5-aminobicyclo[3.2.1]octan-1-yl)methanol as a brown oil. ESI-MS m/z: 156 (M+H)⁺.

Step 8: Preparation of N-(5-(hydroxymethyl)bicyclo[3.2.1]octan-1-yl)pyrazine-2-carboxamide

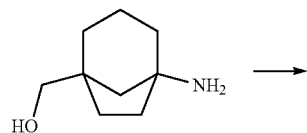

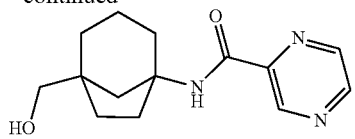

To a solution of (5-aminobicyclo[3.2.1]octan-1-yl)methanol (327 g, 2.1 mmol) and pyrazine-2-carboxylic acid (260 mg, 2.1 mmol) in DMF (10 mL) was added DIEA (680 mg, 5.22 mmol), followed by HATU (800 mg, 2.1 mmol). After stirring at room temperature for an hour, the reaction mixture was quenched with water (25 mL) and extracted with ethyl acetate (3×25 mL). The combined organic phase was washed with brine, dried over Na₂SO₄ and concentrated under rescued pressure to give a residue, which was purified by column chromatography (silica gel, petroleum ether/ethyl acetate=2/1) to afford 540 mg (100%) of the title compound, N-(5-(hydroxymethyl)bicyclo[3.2.1]octan-1-yl)pyrazine-2-carboxamide as a colorless oil. ESI-MS m/z: 262 (M+H)⁺.

Step 9: N-(5-formylbicyclo[3.2.1]octan-1-yl)pyrazine-2-carboxamide

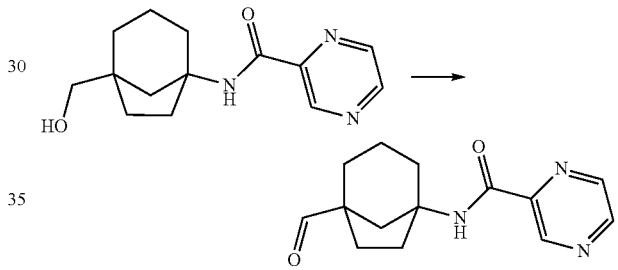

To a solution of N-(5-(hydroxymethyl)bicyclo[3.2.1]octan-1-yl)pyrazine-2-carboxamide (540 mg, 2.1 mmol) in DCM (20 mL) was added PCC (670 mg, 3.1 mmol) in portions and the reaction mixture was stirred at room temperature for two hours. The mixture was filtered through a pad of silica gel and the filtrate was concentrated. The resulting residue was purified by column chromatography (silica gel, petroleum ether/ethyl acetate=2/1) to yield 350 mg (65%) of the title compound, N-(5-formylbicyclo[3.2.1]octan-1-yl)pyrazine-2-carboxamide, as a white solid. ESI-MS m/z: 260 (M+H)⁺.

Step 10: N-(5-ethynylbicyclo[3.2.1]octan-1-yl)pyrazine-2-carboxamide

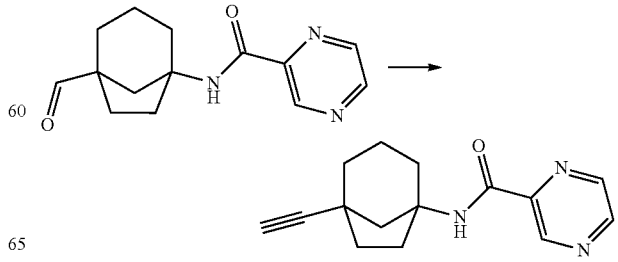

To a stirred mixture of N-(5-formylbicyclo[3.2.1]octan-1-yl)pyrazine-2-carboxamide (350 mg, 1.35 mmol) and K₂CO₃ (370 mg, 2.7 mmol) in methanol (25 mL) under N₂ was added dimethyl (1-diazo-2-oxopropyl)phosphonate (310 mg, 1.62 mmol). After stirring at room temperature for three hours, the clear reaction solution was partitioned between ethyl acetate (20 mL) and 5% NaHCO₃ (20 mL). The aqueous layer was extracted with ethyl acetate (2×20 mL). The combined organic phase was washed with brine, dried over Na₂SO₄ and concentrated under reduced pressure to afford 210 mg (61%) of crude title compound, N-(5-ethynylbicyclo[3.2.1]octan-1-yl)pyrazine-2-carboxamide, as an off-white solid. ESI-MS m/z: 256 (M+H)⁺. It was used in the next step without further purification.

Intermediates 2-A and 2-B: (1R,5S)-5-Pyridin-2-ylethynyl-bicyclo[3.2.1]oct-1-ylamine (2-A) and (1S,5R)-5-pyridin-2-ylethynyl-bicyclo[3.2.1]oct-1-ylamine (2-B)

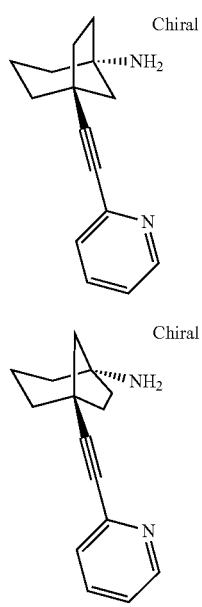

Intermediate 2 was prepared from 5-(benzyloxycarbonylamino)bicyclo[3.2.1]octane-1-carboxylate via the process of Scheme 2, supra, as follows:

Step 1: Methyl 5-aminobicyclo[3.2.1]octane-1-carboxylate

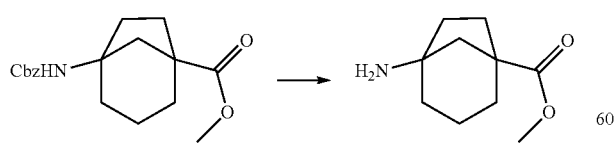

To a solution of 5-(benzyloxycarbonylamino)bicyclo[3.2.1]octane-1-carboxylate (10 g, 31.5 mmol) in EtOH (50 mL) was added Pd/C (900 mg) under H₂ atmosphere at room temperature and stirred overnight. The reaction mixture was filtered through Celite. The filtrate was concentrated under reduced pressure to afford 5.5 g (96%) of the crude title compound, methyl 5-aminobicyclo[3.2.1]octane-1-carboxylate, as a colorless oil. ESI-MS m/z: 184 (M+H)⁺.

Step 2: Methyl 5-(tert-butoxycarbonylamino)bicyclo[3.2.1]octane-1-carboxylate

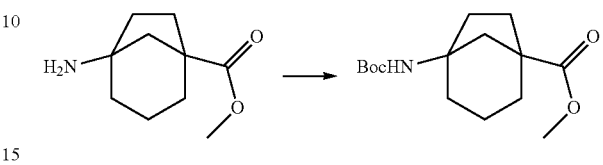

To a solution of methyl 5-aminobicyclo[3.2.1]octane-1-carboxylate (5.5 g, 30.1 mmol) in THF (60 mL) was added TEA (7.6 g, 75.3 mmol) and (Boc)₂O (8 g, 36.1 mmol) under N₂. After stirring at room temperature overnight, the solvent was removed under reduced pressure. The resulting residue was diluted with ethyl acetate (150 mL), washed with water and brine, dried over Na₂SO₄ and concentrated under reduced pressure. The residue was purified by column chromatography (silica gel, petroleum ether/ethyl acetate=8/1) to give 7.8 g (92%) of the title compound, methyl 5-(tert-butoxycarbonylamino)bicyclo[3.2.1]octane-1-carboxylate, as a white oil. ESI-MS m/z: 228 (M-55)⁺.

Step 3: tert-Butyl 5-(hydroxymethyl)bicyclo[3.2.1]octan-1-ylcarbamate (9)

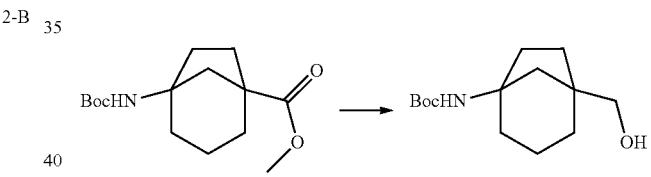

To a solution of methyl 5-(tert-butoxycarbonylamino)bicyclo[3.2.1]octane-1-carboxylate (7.8 g, 27.6 mmol) in THF (65 mL) was added LiBH₄ (2.0 M in THF, 28 mL, 56.0 mmol) dropwise at 0° C. under N₂. The solution was warmed up to room temperature gradually and stirred overnight. The reaction mixture was quenched with Sat. NH₄Cl and extracted with ethyl acetate (3×150 mL). The combined organic layer was washed with brine, dried over Na₂SO₄ and concentrated under reduced pressure to afford 7.0 g (90%) of the crude title compound, tert-Butyl 5-(hydroxymethyl)bicyclo[3.2.1]octan-1-ylcarbamate, as colorless oil, which was used in the next step without further purification. ESI-MS m/z: 200 (M-55)⁺.

Step 4: tert-Butyl 5-formylbicyclo[3.2.1]octan-1-ylcarbamate

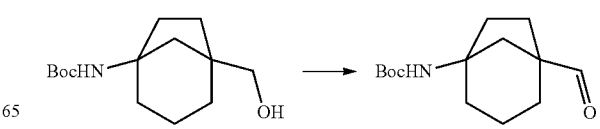

To a stirred solution of tert-butyl 5-(hydroxymethyl)bicyclo[3.2.1]octan-1-ylcarbamate (7.0 g, 24.8 mmol) in DCM (50 mL) was added PCC (8.0 g, 37.2 mmol) in portions under N₂ and the reaction mixture was stirred at room temperature for two hours. The mixture was filtered through a pad of silica gel and the filtrate was concentrated under reduced pressure to give 6.44 g (92%) of the crude title compound, tert-butyl 5-formylbicyclo[3.2.1]octan-1-ylcarbamate, as a brown oil, which was used in the next step without further purification. ESI-MS m/z: 198 (M-55)⁺.

Step 5: tert-Butyl 5-ethynylbicyclo[3.2.1]octan-1-ylcarbamate

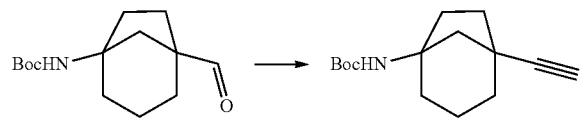 [SMILES: CC(C)(C)OC(=O)NC12CCCC(C=O)(CC1)C2 ; C#CC12CCCC(NC(=O)OC(C)(C)C)(CC1)C2]

To a solution of tert-butyl 5-formylbicyclo[3.2.1]octan-1-ylcarbamate (6.4 g, 25.3 mmol) and K₂CO₃ (7.1 g, 50.6 mmol) in methanol (200 mL) under N₂ was added dimethyl 1-diazo-2-oxopropylphosphonate (6.0 g, 30.3 mmol). After stirring at room temperature for three hours, the reaction mixture became a clear solution. Ethyl acetate (300 mL) and 5% NaHCO₃ (300 mL) were added. Aqueous layer was extracted with ethyl acetate (2×200 mL). The organic layers were combined, washed with brine, dried over Na₂SO₄ and concentrated under reduced pressure to give 5.8 g (90%) the crude title compound, tert-butyl 5-ethynylbicyclo[3.2.1]octan-1-ylcarbamate, as colorless oil. ESI-MS m/z: 194 (M-55)⁺.

Step 6: tert-Butyl 5-(pyridin-2-ylethynyl)bicyclo[3.2.1]octan-1-ylcarbamate

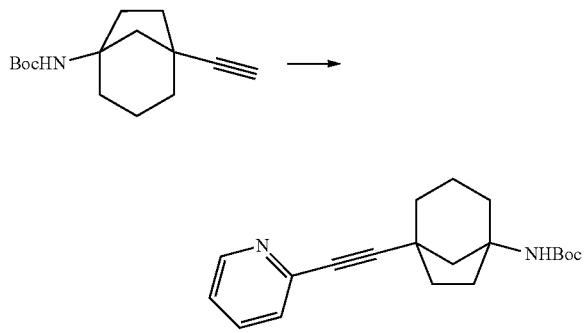

To a stirred solution of tert-butyl 5-ethynylbicyclo[3.2.1]octan-1-ylcarbamate (5.8 g, 23.3 mmol) and 2-chloropyridine (3.18 g, 28 mmol) in TEA (30 mL) and acetonitrile (150 mL) under N₂ was added Pd(PPh₃)₄ (266 mg, 0.23 mmol), followed by CuI (266 mg, 1.4 mmol). The reaction mixture was heated at 70° C. for three hours. After cooled to room temperature, the reaction mixture was diluted with ethyl acetate (250 mL), washed with water (150 mL) and brine, dried over Na₂SO₄ and concentrated under reduced pressure. The residue was purified by column chromatography (silica gel, petroleum ether/ethyl acetate=5/1) to give 5.8 g (76%) of the title compound, tert-butyl 5-(pyridin-2-ylethynyl)bicyclo[3.2.1]octan-1-ylcarbamate, as a white solid. ESI-MS m/z: 298 (M-55)⁺.

Step 7: 5-(Pyridin-2-ylethynyl)bicyclo[3.2.1]oct-1-ylamine

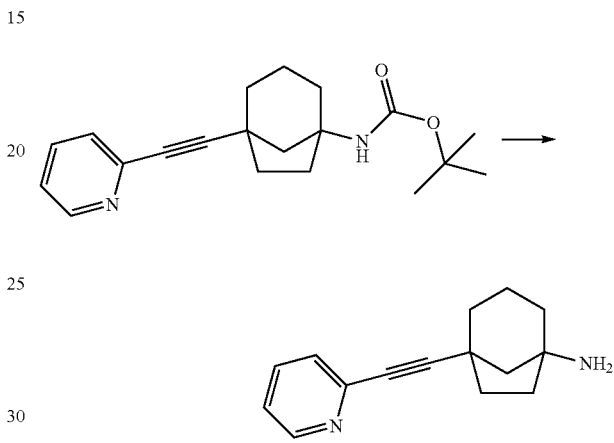

To a solution of tert-butyl 5-(pyridin-2-ylethynyl)bicyclo[3.2.1]octan-1-ylcarbamate (1.1 g, 3.37 mmol) in DCM (5.0 mL) was added 2,2,2-trifluoroacetic acid (2.0 mL). After stirring at room temperature for two hours, the reaction mixture was concentrated under reduced pressure. The residue was diluted with water (10 mL) and extracted with ethyl ether (10 mL) to remove non-amine organic impurity. The aqueous layer was basified with NaOH to pH=12 and then extracted with DCM (3×10 mL). The combined DCM layer was washed with brine, dried over Na₂SO₄ and concentrated under reduced pressure to afford 600 mg (78%) of the title compound, 5-(pyridin-2-ylethynyl)bicyclo[3.2.1]oct-1-ylamine. ¹HNMR (500 MHz, CDCl₃): δ 8.51 (d, J=5.0 Hz, 1H), 7.59-7.56 (m, 1H), 7.35 (d, J=7.5 Hz, 1H), 7.16-7.13 (dd, J=7.0, 5.0 Hz, 1H), 2.42 (s, 2H), 2.15-1.54 (m, 12H); ESI-MS m/z: 227 (M+H)⁺.

Step 7: (1R,5S)-5-Pyridin-2-ylethynyl-bicyclo[3.2.1]oct-1-ylamine (2-A) and (1S,5R)-5-pyridin-2-ylethynyl-bicyclo[3.2.1]octylamine (2-B)

5-(pyridin-2-ylethynyl)bicyclo[3.2.1]oct-1-ylamine (2.0 g) was resolved on a SFC preparative separation system into two enantiomers (800 mg, each) (FIG. 1). The front peak was arbitrarily assigned as (1R,5S)-5-pyridin-2-ylethynyl-bicyclo[3.2.1]oct-1-ylamine (2-A) and the back peak was arbitrarily assigned as (1S,5R)-5-pyridin-2-ylethynyl-bicyclo[3.2.1]octylamine (2-B).

Intermediates 3-A and 3-B: (1R,5S)-5-(6-Methyl-pyridin-2-ylethynyl)-bicyclo[3.2.1]oct-1-ylamine (3-A) and (1S,5R)-5-(6-methyl-pyridin-2-ylethynyl)-bicyclo pail oct-1-ylamine (3-B)

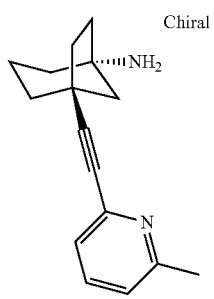

3-A

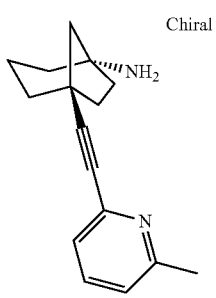

3-B

Intermediates 3-A (1.6 g) and 3-B (1.5 g) were prepared from tert-butyl 5-ethynylbicyclo[3.2.1]octan-1-ylcarbamate according to the procedure described in the synthesis of intermediates 2-A and 2-B.

Intermediates 4-A and 4-B: (1R,5S)-5-(6-Fluoro-pyridin-2-ylethynyl)-bicyclo[3.2.1]oct-1-ylamine (4-A) and (1S,5R)-5-(6-fluoro-pyridin-2-ylethynyl)-bicyclo[3.2.1]oct-1-ylamine (4-B)

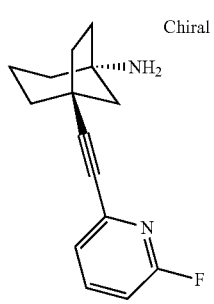

4-A

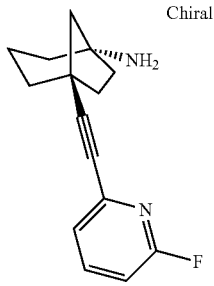

4-B

Intermediates 4-A (100 mg) and 4-B (100 mg) were prepared from tert-butyl 5-ethynylbicyclo[3.2.1]octan-1-ylcarbamate according to the procedure described in the synthesis of intermediates 2-A and 2-B.

Intermediates 5-A and 5-B: (1R,5S)-5-(3-Fluoro-pyridin-2-ylethynyl)-bicyclo[3.2.1]oct-1-ylamine (5-A) and (1S,5R)-5-(3-fluoro-pyridin-2-ylethynyl)-bicyclo[3.2.1]oct-1-ylamine (5-B)

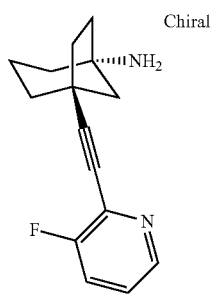

5-A

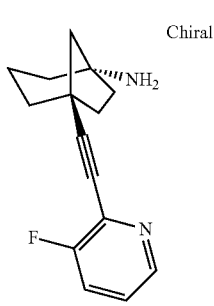

5-B

Intermediates 5-A (110 mg) and 5-B (100 mg) were prepared from tert-butyl 5-ethynylbicyclo[3.2.1]octan-1-ylcarbamate according to the procedure described in the synthesis of intermediates 2-A and 2-B.

Intermediates 6-A and 6-B: (1R,5S)-5-Pyrazin-2-ylethynyl-bicyclo[3.2.1]oct-1-ylamine (6-A) and (1S,5R)-5-pyrazin-2-ylethynyl-bicyclo[3.2.1]oct-1-ylamine (6-B)

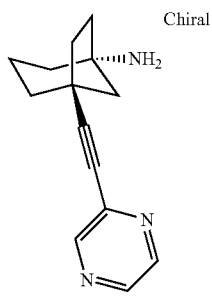
6-A

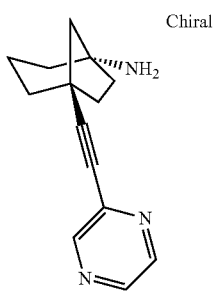
6-B

Intermediates 6-A (1.3 g) and 6-B (1.2 g) were prepared from tert-butyl 5-ethynylbicyclo[3.2.1]octan-1-ylcarbamate according to the procedure described in the synthesis of intermediates 2-A and 2-B.

Intermediates 7-A and 7-B: (1R,5S)-5-(2-Methyl-thiazol-4-ylethynyl)-bicyclo[3.2.1]oct-1-ylamine (7-A) and (1S,5R)-5-(2-methyl-thiazol-4-ylethynyl)-bicyclo[3.2.1]oct-1-ylamine (7-B)

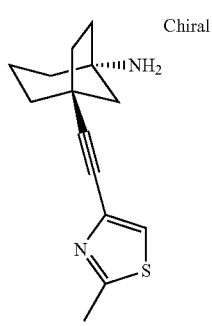
7-A

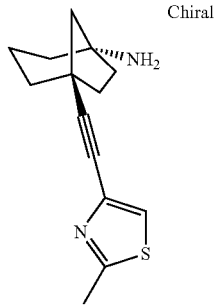
7-B

Intermediates 7-A (0.13 g) and 7-B (0.12 g) were prepared from tert-butyl 5-ethynylbicyclo[3.2.1]octan-1-ylcarbamate according to the procedure described in the synthesis of intermediates 2-A and 2-B.

Intermediate 8:
3-Chloro-N-(3-ethynyl-adamantan-1-yl)-benzamide

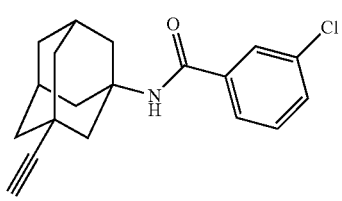 [SMILES: C#CC12CC3CC(C1)CC(NC(=O)c1cccc(Cl)c1)(C3)C2]

Intermediate 8 was prepared from 3-amino-adamantane-1-carboxylic acid methyl ester HCl salt (Hermogenes N. J. et al.; U.S. Pat. No. 7,947,680 B2) via the process of Scheme 3, supra, as follows:

Step 1: Methyl 3-[(3-chlorobenzoyl)amino]adamantane-1-carboxylate

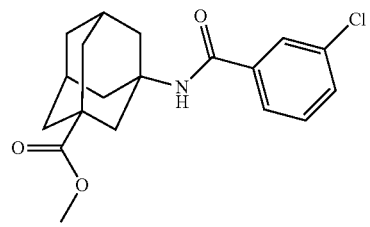

To a solution of 3-amino-adamantane-1-carboxylic acid methyl ester HCl salt (Hermogenes N. J. et al.; U.S. Pat. No. 7,947,680 B2) (160 mg, 0.65 mmol) and 3-chlorobenzoic acid (130 mg, 0.78 mmol) in DMF (5 mL) was added DIEA (340 mg, 2.6 mmol) and HATU (300 mg, 0.78 mmol) under $N_2$. After stirring at room temperature for an hour, the reaction was quenched with brine, the aqueous layer was extracted with ethyl acetate (3×20 mL), and the combined organic layer was washed with brine, dried over Na₂SO₄ and concentrated under reduced pressure. The resulting residue was purified by column chromatography (silica gel, petroleum ether/ethyl acetate=5/1) to afford 220 mg (97%) of the title compound, methyl 3[(3-chlorobenzoyl)amino]adamantane-1-carboxylate, as a white solid. ESI-MS m/z: 348 (M+H)⁺.

Step 2: 3-chloro-N-[3-(hydroxymethyl)-1-adamantyl]benzamide

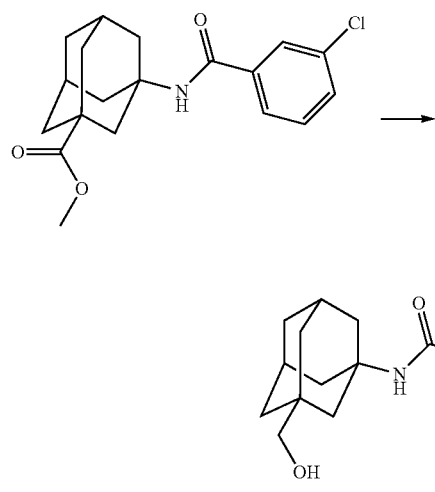

To a solution of methyl 3-[(3-chlorobenzoyl)amino]adamantane-1-carboxylate (220 mg, 0.63 mmol) in THF (15 mL) at 0° C. was added LiBH₄ (2.0M in THF, 0.6 mL, 1.2 mmol) dropwise under N₂. After stirring at 0° C. for 30 min, the reaction mixture was allowed to warm up to room temperature overnight. The reaction was quenched with Sat. NH₄Cl, and the aqueous layer was extracted with ethyl acetate (3×20 mL). The combined organic layer was washed with brine, dried over Na₂SO₄ and concentrated under reduced pressure to give 200 mg (99%) of the title compound, 3-chloro-N-[3-(hydroxymethyl)-1-adamantyl]benzamide, as a colorless oil, which was used in the next step without further purification. ESI-MS m/z: 320 (M+H)⁺.

Step 3: 3-chloro-N-(3-formyl-1-adamantyl)benzamide

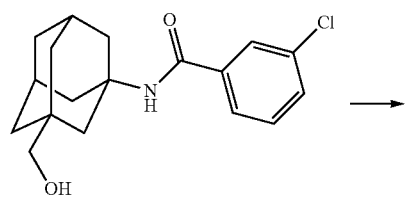

To a solution of 3-chloro-N-[3-(hydroxymethyl)-1-adamantyl]benzamide (200 mg, 0.63 mmol) in DCM (15 mL) was added PCC (200 mg, 0.93 mmol) in one portion and the reaction mixture was stirred at room temperature for two hours. The reaction mixture was then filtered through a pad of silica gel and the filtrate was concentrated under reduced pressure to give 200 mg (100%) of crude title compound, 3-chloro-N-(3-formyl-1-adamantyl)benzamide, as a brown oil. ESI-MS m/z: 318 (M+H)⁺.

Step 4: 3-chloro-N-(3-ethynyl-1-adamantyl)benzamide

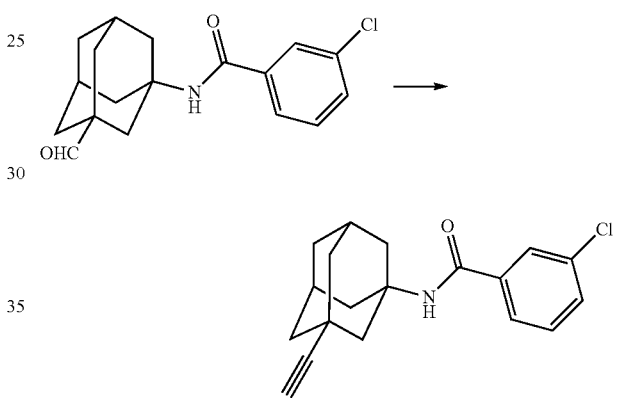

To a stirred mixture of 3-chloro-N-(3-formyl-1-adamantyl)benzamide (350 mg, 1.35 mmol) and K₂CO₃ (370 mg, 2.7 mmol) in methanol (25 mL) under N₂ was added dimethyl (1-diazo-2-oxopropyl)phosphonate (310 mg, 1.62 mmol). After stirring at room temperature for three hours, the clear reaction solution was partitioned between ethyl acetate (20 mL) and 5% NaHCO₃ (20 mL) and the aqueous layer was extracted with ethyl acetate (2×20 mL). The combined organic layer was washed with brine, dried over Na₂SO₄ and concentrated under reduced pressure to yield 210 mg (61%) of the title compound, 3-chloro-N-(3-ethynyl-1-adamantyl)benzamide, as an off-white solid. ESI-MS m/z: 256 (M+H)⁺.

Intermediate 9: 3-Fluoro-N-(3-ethynyl-1-adamantyl)benzamide

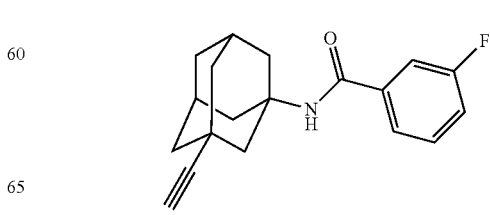

Intermediate 9 (220 mg) was made from 3-amino-adamantane-1-carboxylic acid methyl ester HCl salt according to the procedure described in the synthesis of intermediate 8.

Intermediate 10: 6-Methyl-pyrazine-2-carboxylic acid (3-ethynyl-adamantan-1-yl)-amide

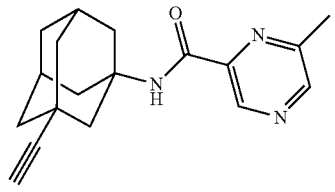 [SMILES: C#CC12CC3CC(C1)CC(NC(=O)c1cncc(C)n1)(C3)C2]

Intermediate 10 (280 mg) was made in an analogous manner to intermediate 8.

Intermediate 11:
3-(pyrazin-2-ylethynyl)-1-adamantylamine

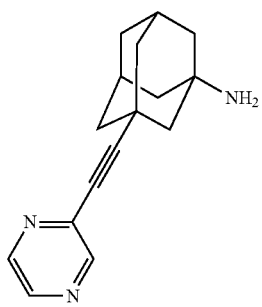 [SMILES: NC12CC3CC(C1)CC(C#Cc1cnccn1)(C3)C2]

Intermediate 11 was prepared from 3-amino-adamantane-1-carboxylic acid methyl ester HCl salt (Hermogenes N. J. et al.; U.S. Pat. No. 7,947,680 B2) via the process of Scheme 4, supra, as follows:

Step 1: Methyl 3-[(tert-butoxycarbonyl)amino]adamantine-1-carboxylate

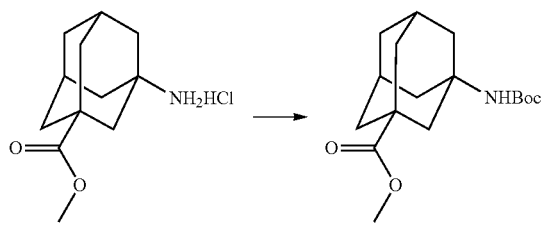

To a solution of 3-amino-adamantane-1-carboxylic acid methyl ester HCl salt (1.0 g, 4.1 mmol) in THF (60 mL) was added TEA (1.0 g, 9.9 mmol) and (Boc)$_2$O (975 mg, 4.4 mmol) under N$_2$ atmosphere. After stirring at room temperature overnight, solvent was removed under reduced pressure. The resulting residue was diluted with ethyl acetate, washed with water and brine, dried over Na$_2$SO$_4$, and concentrated under reduced pressure to afford a crude product which was purified by column chromatography (silica gel, petroleum ether/ethyl acetate=8/1) to give 1.2 g (95%) of the title compound, methyl 3-[(tert-butoxycarbonyl)amino]adamantine-1-carboxylate as a white solid. ESI-MS m/z: 254 (M-55)$^+$.

Step 2: tert-Butyl 3-(hydroxymethyl)-1-adamantylcarbamate

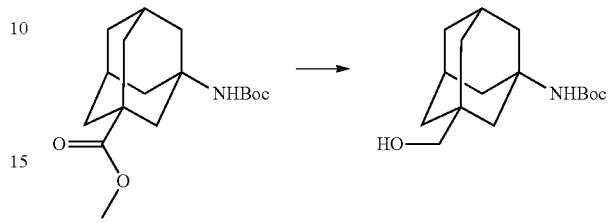

To a solution of methyl 3-[(tert-butoxycarbonyl)amino]adamantine-1-carboxylate (1.2 g, 3.8 mmol) in THF (65 mL) was added LiBH$_4$ (2.0 M in THF, 4 mL, 8 mmol) dropwise at 0° C. under N$_2$ atmosphere. After completion of addition, the reaction was allowed to warm up to room temperature overnight. The reaction was then quenched with Sat. NH$_4$Cl, aqueous layer was extracted with ethyl acetate (3×25 mL), and the combined organic phase was washed with brine, dried over Na$_2$SO$_4$ and concentrated under reduced pressure to afford 1.2 g (100%) of the title compound, tert-butyl 3-(hydroxymethyl)-1-adamantylcarbamate, as a colorless oil, which was used in the next step without further purification. ESI-MS m/z: 226 (M-55)$^+$.

Step 3: tert-Butyl-3-formyl-1-adamantylcarbamate

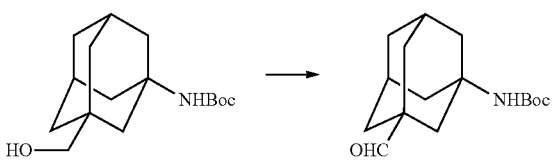 [SMILES: CC(C)(C)OC(=O)NC12CC3CC(CC(CO)(C3)C1)C2 ; CC(C)(C)OC(=O)NC12CC3CC(CC(C=O)(C3)C1)C2]

To a stirred solution of tert-butyl 3-(hydroxymethyl)-1-adamantylcarbamate (1.2 g, 4.3 mmol) in DCM (50 mL) was added PCC (1.4 g, 6.5 mmol) in portions under N$_2$ atmosphere. After stirring at room temperature for two hours. the mixture was filtered through a pad of silica gel and the filtrate was concentrated under reduced pressure to give 1.1 g (92%) of the title compound, tert-butyl-3-formyl-1-adamantylcarbamate, as a brown oil, which was used in the next step without further purification. ESI-MS m/z: 224 (M-55)$^+$.

Step 4: tert-Butyl 3-ethynyl-1-adamantylcarbamate

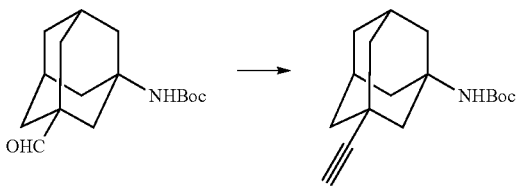 [SMILES: CC(C)(C)OC(=O)NC12CC3CC(CC(C=O)(C3)C1)C2 ; C#CC12CC3CC(C1)CC(NC(=O)OC(C)(C)C)(C3)C2]

To a solution of tert-butyl-3-formyl-1-adamantylcarbamate (600 mg, 2.1 mmol) and $K_2CO_3$ (590 mg, 4.2 mmol) in methanol (60 mL) under $N_2$ atmosphere was added dimethyl (1-diazo-2-oxopropyl)phosphonate (490 mg, 2.5 mmol). After stirring at room temperature for three hours the clear reaction solution was partitioned between ethyl acetate (100 mL) and 5% $NaHCO_3$ (100 mL) and the aqueous layer was extracted with ethyl acetate (2×100 mL). The combined organic layer was washed with brine, dried over $Na_2SO_4$ and concentrated under reduced pressure to afford 600 mg (100%) of the title compound, tert-butyl 3-ethynyl-1-adamantylcarbamate as a colorless oil. ESI-MS m/z: 220 (M-55)$^+$.

Step 5: tert-Butyl 3-(pyrazin-2-ylethynyl)-1-adamantylcarbamate

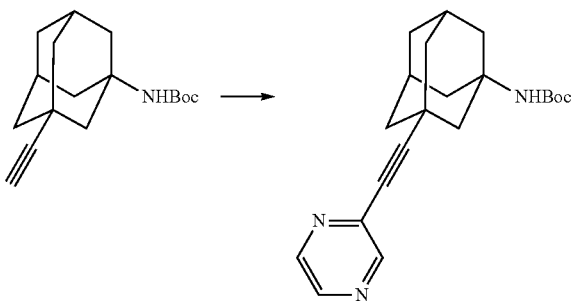 [SMILES: C#CC12CC3CC(C1)CC(NC(=O)OC(C)(C)C)(C3)C2 ; CC(C)(C)OC(=O)NC12CC3CC(CC(C#Cc4cnccn4)(C3)C1)C2]

To a stirred solution of tert-butyl 3-ethynyl-1-adamantylcarbamate (120 mg, 0.44 mmol) and 2-chloropyrazine (120 mg, 1.05 mmol) in TEA (3 mL) and acetonitrile (15 mL) was added $Pd(PPh_3)_4$ (5 mg, 0.04 mmol), followed by an addition of CuI (5 mg, 0.026 mmol) under $N_2$ atmosphere. After stirring at 70° C. for three hours, the reaction was cooled to room temperature, diluted with ethyl acetate (50 mL), washed with water (50 mL) and brine, dried over $Na_2SO_4$ and concentrated under reduced pressure. The resulting residue was purified by column chromatography (silica gel, petroleum ether/ethyl acetate=5/1) to give 108 mg (70%) of the title compound, tert-butyl 3-(pyrazin-2-ylethynyl)-1-adamantylcarbamate as a white solid. ESI-MS m/z: 298 (M-55)$^+$.

Step 6: 3-(Pyrazin-2-ylethynyl)-1-adamantylamine

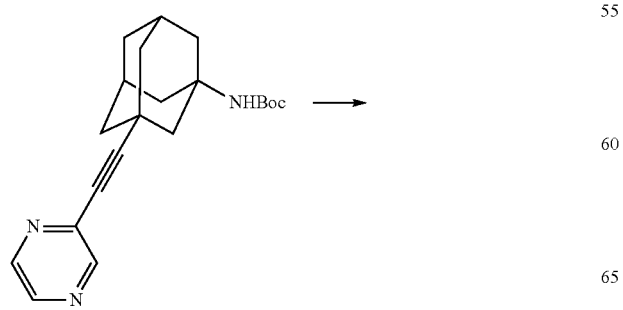

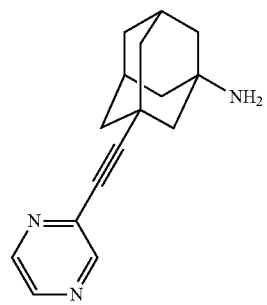

To a stirred solution of tert-butyl 3-(pyrazin-2-ylethynyl)-1-adamantylcarbamate (108 mg, 0.31 mol) in DCM (3 mL) was added TFA (0.5 mL). After stirring at room temperature for an hour, the reaction was concentrated under reduced pressure. The resulting residue was diluted with DCM (25 mL), washed with Sat. $NaHCO_3$ and brine, dried over $Na_2SO_4$ and concentrated under reduced pressure to yield 60 mg (78%) of the title compound, 3-(pyrazin-2-ylethynyl)-1-adamantylamine, as a white solid. ESI-MS m/z: 254 (M+H)$^+$.

Intermediate 12: 3-(6-Methyl-pyrazin-2-ylethynyl)-adamantan-1-ylamine

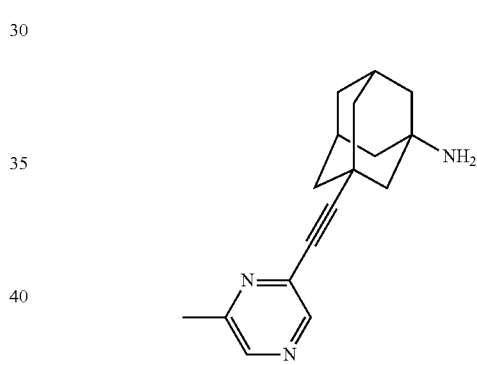

Intermediate 12 (150 mg) was made from tert-butyl 3-ethynyl-1-adamantylcarbamate according to the procedure described in the synthesis of intermediate 11.

Intermediate 13: 3-Pyridin-2-ylethynyl-adamantan-1-ylamine

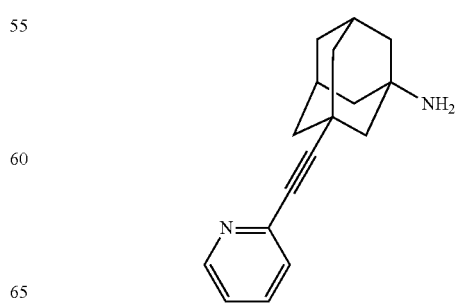

Intermediate 13 (1.1 g) was prepared from tert-butyl 3-ethynyl-1-adamantylcarbamate according to the procedure described in the synthesis of intermediate 11.

Intermediate 14: 3-(6-Methyl-pyridin-2-ylethynyl)-adamantan-1-ylamine

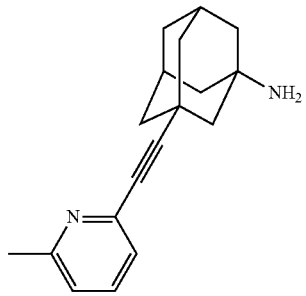 [SMILES: Cc1cccc(C#CC23CC4CC(CC(N)(C4)C2)C3)n1]

Intermediate 14 (950 mg) was prepared from tert-butyl 3-ethynyl-1-adamantylcarbamate according to the procedure described in the synthesis of intermediate 11.

Intermediate 15: 3-(2-Methyl-pyridin-4-ylethynyl)-adamantan-ylamine

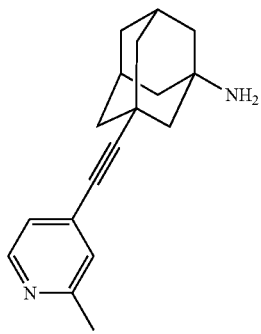 [SMILES: Cc1cc(C#CC23CC4CC(CC(N)(C4)C2)C3)ccn1]

Intermediate 15 (105 mg) was prepared from tert-butyl 3-ethynyl-1-adamantylcarbamate according to the procedure described in the synthesis of intermediate 11.

Intermediate 16: 3-(6-Methyl-pyridin-3-ylethynyl)-adamantan-1-ylamine

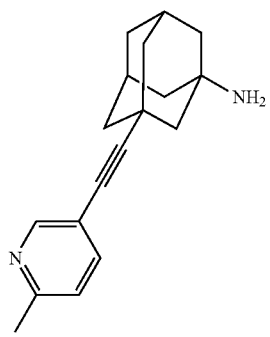 [SMILES: Cc1ccc(C#CC23CC4CC(CC(N)(C4)C2)C3)cn1]

Intermediate 16 (135 mg) was prepared from tert-butyl 3-ethynyl-1-adamantylcarbamate according to the procedure described in the synthesis of intermediate 11.

Intermediate 17: 3-(4-Methyl-thiazol-2-ylethynyl)-adamantan-1-ylamine

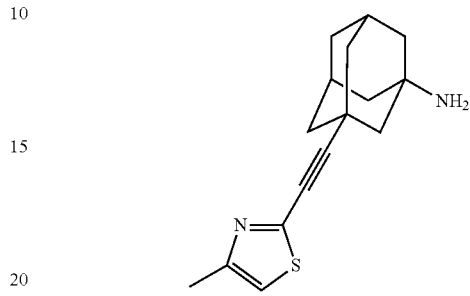

Intermediate 17 (1.0 g) was prepared from tert-butyl 3-ethynyl-1-adamantylcarbamate according to the procedure described in the synthesis of intermediate 11.

3. Preparation of Compounds of the Invention

Unless specified otherwise, all starting materials and reagents were obtained from commercial suppliers, such as Sigma-Aldrich Corp. (St. Louis, Mo., USA) and its subsidiaries, and used without further purification.

Example 1

Pyrazine-2-carboxylic acid [5-(6-methyl-pyridin-2-ylethynyl)-bicyclo[3.2.1]oct-1-yl]-amide

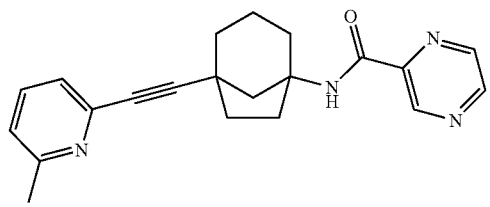 [SMILES: Cc1cccc(C#CC23CCCC(NC(=O)c4cnccn4)(CC2)C3)n1]

Example 1 was prepared from intermediate 1 via the process of Scheme 1, supra, as follows:

To a stirred mixture of intermediate 1, N-(5-ethynylbicyclo[3.2.1]octan-1-yl)pyrazine-2-carboxamide (40 mg, 0.16 mmol) and 2-bromo-6-methylpyridine (30 mg, 0.18 mmol) in TEA (0.5 mL) and acetonitrile (2 mL) was added Pd(PPh$_3$)$_4$ (2 mg, 0.02 mmol), followed by an addition of CuI (4 mg, 0.02 mmol). After heated at 70° C. for three hours, the reaction was cooled to room temperature, diluted with ethyl acetate (30 mL), washed with water and brine, dried over Na$_2$SO$_4$ and concentrated under reduced pressure. The resulting residue was purified by Prep HPLC to afford 20 mg (36%) of the title compound, pyrazine-2-carboxylic acid [5-(6-methyl-pyridin-2-ylethynyl)-bicyclo[3.2.1]oct-1-yl]-amide, as a white solid. $^1$HNMR (500 MHz, CDCl$_3$): δ 9.40 (s, 1H), 8.75 (s, 1H), 8.51 (s, 1H), 7.91 (s, 1H), 7.51 (t, J=7.5 Hz, 1H), 7.21 (d, J=8.0 Hz, 1H), 7.06 (d, J=7.5 Hz, 1H), 2.55-2.52 (m, 4H), 2.29-1.76 (m, 11H); ESI-MS m/z: 347 (M+H)$^+$.

Examples 2-13 of table 1 were prepared analogously to Example 1.

Example 2 pyrazine-2-carboxylic acid [5-(6-fluoro-pyridin-2-ylethynyl)-bicyclo[3.2.1]oct-1-yl]-amide $^1$H NMR (500 MHz, CDCl$_3$): δ 9.35 (s, 1H), 8.74 (s, 1H), 8.50 (s, 1H), 7.90 (s, 1H), 7.71 (t, J=8.0 Hz, 1H), 7.26-7.24 (m, 1H), 6.84 (dd, J=8.5, 2.0 Hz, 1H), 2.53-2.51 (m, 1H), 2.22-1.74 (m, 11H); ESI-MS m/z: 351 (M+H)$^+$.

Example 3 pyrazine-2-carboxylic acid [5-(3-fluoro-phenylethynyl)-bicyclo[3.2.1]oct-1-yl]-amide $^1$HNMR (500 MHz, CDCl$_3$): δ 9.40 (s, 1H), 8.75 (s, 1H), 8.51 (s, 1H), 7.92 (s, 1H), 7.25-7.23 (m, 1H), 7.17 (d, J=7.5 Hz, 1H), 7.09 (d, J=9.5 Hz, 1H), 6.98-6.95 (m, 1H), 2.53-2.51 (m, 1H), 2.22-1.74 (m, 11H); ESI-MS m/z: 350 (M+H)$^+$.

Example 4 pyrazine-2-carboxylic acid [5-(3-chloro-phenylethynyl)-bicyclo[3.2.1]oct-1-yl]-amide $^1$H NMR (500 MHz, CDCl$_3$): δ 9.41 (s, 1H), 8.76 (s, 1H), 8.51 (s, 1H), 7.90 (s, 1H), 7.37 (s, 1H), 7.24-7.18 (m, 3H), 2.51-2.49 (m, 1H), 2.20-1.72 (m, 11H); ESI-MS m/z: 366 (M+H)$^+$.

Example 5 pyrazine-2-carboxylic acid [5-(3-fluoro-pyridin-2-ylethynyl)-bicyclo[3.2.1]oct-1-yl]-amide $^1$H NMR (500 MHz, CDCl$_3$): δ 9.40 (s, 1H), 8.75 (s, 1H), 8.51 (s, 1H), 8.37 (s, 1H), 7.99 (s, 1H), 7.40 (t, J=8.5 Hz, 1H), 7.24-7.22 (m, 1H), 2.55-2.53 (m, 1H), 2.32-1.76 (m, 11H); ESI-MS m/z: 351 (M+H)$^+$.

Example 6

6-methyl-pyrazine-2-carboxylic acid [5-(3-fluoro-phenylethynyl)-bicyclo[3.2.1]oct-1-yl]-amide $^1$H NMR (500 MHz, CDCl$_3$): δ 9.22 (s, 1H), 8.64 (s, 1H), 7.94 (d, J=8.0 Hz, 1H), 7.27-7.21 (m, 1H), 7.17 (d, J=9.5 Hz, 1H), 7.10-7.00 (m, 1H), 6.98 (t, J=7.5 Hz, 1H), 2.61 (s, 3H), 2.54-2.51 (m, 1H), 2.22-1.72 (m, 11H); ESI-MS m/z: 364 (M+H)$^+$.

Example 7

6-methyl-pyrazine-2-carboxylic acid (5-pyridin-2-ylethynyl-bicyclo[3.2.1]oct-1-yl)-amide $^1$H NMR (500 MHz, CDCl$_3$): δ 9.24-9.15 (m, 1H), 8.66-8.54 (m, 2H), 7.94 (s, 1H), 7.70-7.14 (m, 3H), 2.61 (s, 3H), 2.55-2.53 (m, 1H), 2.28-1.71 (m, 11H); ESI-MS m/z: 347 (M+H)$^+$.

Example 8

6-methyl-pyrazine-2-carboxylic acid [5-(2-methyl-pyrimidin-4-ylethynyl)-bicyclo[3.2.1]oct-1-yl]-amide $^1$H NMR (500 MHz, CDCl$_3$): δ 9.19 (s, 1H), 8.61-8.57 (m, 2H), 7.93 (s, 1H), 7.13 (d, J=6.5 Hz, 1H), 2.72 (s, 3H), 2.60 (s, 3H), 2.58-2.55 (m, 1H), 2.27-1.75 (m, $^1$H); ESI-MS m/z: 362 (M+H)$^+$.

Example 9 pyridine-2-carboxylic acid [5-(6-methyl-pyridin-2-ylethynyl)-bicyclo[3.2.1]oct-1-yl]-amide δ 8.53 (d, J=4.5 Hz, 1H), 8.18 (d, J=8.0 Hz, 2H), 7.84 (t, J=8.0 Hz, 1H), 7.51-7.39 (m, 2H), 7.20 (d, J=7.5 Hz, 1H), 7.04 (d, J=7.5 Hz, 1H), 2.54-2.52 (m, 4H), 2.27-1.73 (m, 11H); ESI-MS m/z: 346 (M+H)$^+$.

Example 10 pyridine-2-carboxylic acid [5-(6-methyl-pyrazin-2-ylethynyl)-bicyclo[3.2.1]oct-1-yl]-amide $^1$H NMR (500 MHz, CDCl$_3$): δ 8.53-8.16 (m, 5H), 7.86-7.83 (m, 1H), 7.42 (s, 1H), 2.56 (brs, 4H), 2.27-1.76 (m, 11H); ESI-MS m/z: 347 (M+H)$^+$.

Example 11

6-Methyl-pyridine-2-carboxylic acid (5-pyridin-2-ylethynyl-bicyclo[3.2.1]oct-1-yl)-amide $^1$H NMR (500 MHz, CDCl$_3$): δ 8.54 (s, 1H), 8.25 (s, 1H), 7.97 (d, J=8.0 Hz, 1H), 7.70 (t, J=8.0 Hz, 1H), 7.62-7.59 (m, 1H), 7.37 (d, J=8.5 Hz, 1H), 7.26-7.24 (m, 1H), 7.18-7.16 (s, 1H), 2.56-2.53 (m, 4H), 2.26-1.74 (m, 11H); ESI-MS m/z: 346 (M+H)$^+$.

Example 12

6-methyl-pyridine-2-carboxylic acid [5-(6-methyl-pyridin-2-ylethynyl)-bicyclo[3.2.1]oct-1-yl]-amide $^1$H NMR (500 MHz, CDCl$_3$): δ 8.24 (s, 1H), 7.97 (d, J=7.5 Hz, 1H), 7.70 (t, J=7.5 Hz, 1H), 7.49 (t, J=7.5 Hz, 1H), 7.25 (d, J=7.5 Hz, 1H), 7.20 (d, J=7.5 Hz, 1H), 7.05 (d, J=7.5 Hz, 1H), 2.58-2.52 (m, 4H), 2.25-1.75 (m, 11H); ESI-MS m/z: 360 (M+H)$^+$.

Example 13

3-Chloro-N-(5-pyrazin-2-ylethynyl-bicyclo[3.2.1]oct-1-yl)-benzamide $^1$H NMR (500 MHz, CDCl$_3$): δ 8.62 (s, 1H), 8.51 (s, 1H), 8.45 (s, 1H), 7.71 (d, J=1.5 Hz, 1H), 7.61 (t, J=8.0 Hz, 1H), 7.47 (d, J=10.5 Hz, 1H), 7.39 (t, J=7.5 Hz, 1H), 6.14 (s, 1H), 2.52-2.49 (m, 1H), 2.27-1.74 (m, 11H); ESI-MS m/z: 366 (M+H)⁺.

Example 14

6-Methyl-N-((1R,5S)-5-(pyridin-2-ylethynyl)bicyclo[3.2.1]octan-1-yl)pyrazine-2-carboxamide

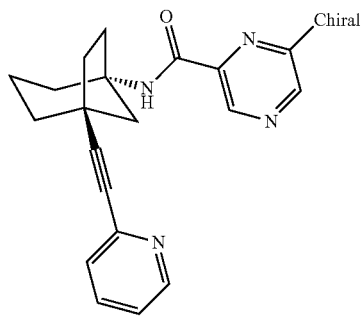

Example 14 was prepared from intermediate 2-A by amidation reaction with 6-methylpyrazine-2-carboxylic acid, as follows:

To a solution of 2-A (80 mg, 0.35 mmol) and 6-methylpyrazine-2-carboxylic acid (58 mg, 0.42 mmol) in DMF (5 mL) was added DIEA (92 mg, 0.70 mmol) and HATU (338 mg, 0.70 mmol) under $N_2$. After stirring at room temperature for an hour, the reaction was quenched with brine and extracted with ethyl acetate (3×20 mL). The combined organic phase was washed with brine, dried over $Na_2SO_4$ and concentrated under reduced pressure. The residue was purified by Prep HPLC to yield 78 mg (64° A) of the title compound, 6-methyl-N-((1R,5S)-5-(pyridin-2-ylethynyl)bicyclo[3.2.1]octan-1-yl)pyrazine-2-carboxamide, as an off-white solid. ¹H NMR (500 MHz, CDCl3): δ 9.18 (s, 1H), 8.60 (s, 1H), 8.55 (d, J=4.7 Hz, 1H), 7.94 (s, 1H), 7.62 (m, 1H), 7.38 (d, J=7.8 Hz, 1H), 7.19 (m, 1H), 2.60 (s, 3H), 2.53 (d, J=10.7 Hz, 1H), 2.25 (m, 1H), 2.18-1.70 (m, 10H); ESI-MS m/z: 347 (M+H)⁺.

Examples 15-23 of table 1 were prepared analogously to Example 14 from intermediate 2-A and commercially available carboxylic acids at ~0.05-1.0 mmol reaction scales.

Example 15

6-methyl-N-((1R,5S)-5-(pyridin-2-ylethynyl)bicyclo[3.2.1]octan-1-yl)picolinamide ¹H NMR (500 MHz, CDCl3) δ 8.55 (d, J=4.8 Hz, 1H), 8.25 (s, 1H), 7.97 (d, J=7.7 Hz, 1H), 7.71 (t, J=7.7 Hz, 1H), 7.62 (t, J=7.7 Hz, 1H), 7.38 (d, J=7.9 Hz, 1H), 7.26 (d, J=6.6 Hz, 1H), 7.19 (m, 1H), 2.58-2.55 (m, 4H), 2.28-2.16 (m, 3H), 2.09-2.05 (m, 2H), 1.97-1.73 (m, 6H); ESI-MS m/z: 346 (M+H)⁺.

Example 16

N-((1R,5S)-5-(pyridin-2-ylethynyl)bicyclo[3.2.1]octan-1-yl)picolinamide

¹H NMR (500 MHz, CDCl3) δ 8.57-8.54 (m, 2H), 8.17 (d, J=8.0 Hz, 2H), 7.84 (t, J=7.6 Hz, 1H), 7.64 (t, J=7.4 Hz, 1H), 7.44-7.36 (m, 2H), 7.23-7.17 (m, 1H), 2.55 (d, J=10.7 Hz, 1H), 2.30-2.15 (m, 3H), 2.05 (d, J=10.7 Hz, 2H), 1.97-1.90 (m, 1H), 1.88-1.74 (m, 5H); ESI-MS m/z: 332 (M+H)⁺.

Example 17

N-((1R,5S)-5-pyridin-2-ylethynyl)bicyclo[3.2.1]octan-1-yl)pyrazine-2-carboxamide ¹H NMR (500 MHz, CDCl3) δ 9.39 (s, 1H), 8.74 (d, J=2.4 Hz, 1H), 8.55 (d, J=4.5 Hz, 1H), 8.50 (s, 1H), 7.91 (s, 1H), 7.63 (t, J=7.7 Hz, 1H), 7.38 (d, J=7.8 Hz, 1H), 7.20 (dd, J=7.3, 5.2 Hz, 1H), 2.53 (d, J=10.7 Hz, 1H), 2.32-2.15 (m, 3H), 2.04 (d, J=10.7 Hz, 2H), 1.99-1.91 (m, 1H), 1.90-1.75 (m, 5H); ESI-MS m/z: 333 (M+H)⁺.

Example 18

2-methyl-N-((1R,5S)-5-(pyridin-2-ylethynyl)bicyclo[3.2.1]octan-1-yl)pyrimidine-4-carboxamide ¹H NMR (500 MHz, CDCl3) δ 8.85 (d, J=5.0 Hz, 1H), 8.55 (d, J=4.7 Hz, 1H), 8.13 (s, 1H), 7.88 (d, J=5.0 Hz, 1H), 7.64 (t, J=7.6 Hz, 1H), 7.39 (d, J=7.8 Hz, 1H), 7.24-7.17 (m, 1H), 2.78 (s, 3H), 2.54 (d, J=10.7 Hz, 1H), 2.31-2.22 (m, 1H), 2.18 (t, J=7.9 Hz, 2H), 2.04 (t, J=9.2 Hz, 2H), 1.98-1.90 (m, 1H), 1.81 (m, 5H); ESI-MS m/z: 347 (M+H)⁺.

Example 19

N-((1R,5S)-5-(pyridin-2-ylethynyl)bicyclo[3.2.1]octan-1-yl)pyrimidine-4-carboxamide ¹H NMR (500 MHz, CDCl₃) δ 9.22 (s, 1H), 8.96 (d, J=5.0 Hz, 1H), 8.55 (d, J=4.7 Hz, 1H), 8.10 (d, J=5.1 Hz, 2H), 7.63 (t, J=7.7 Hz, 1H), 7.38 (d, J=7.8 Hz, 1H), 7.19 (dd, J=7.3, 5.1 Hz, 1H), 2.53 (d, J=10.7 Hz, 1H), 2.26 (dd, J 11.9, 8.6 Hz, 1H), 2.21-2.14 (m, 2H), 2.03 (t, J=10.1 Hz, 2H), 1.95 (dd, J=12.7, 7.0 Hz, 1H), 1.82 (m, 5H); ESI-MS m/z: 333 (M+H)⁺.

Example 20

5-fluoro-N-((1R,5S)-5-(pyridin-2-ylethynyl)bicyclo[3.2.1]octan-1-yl)picolinamide ¹H NMR (500 MHz, CDCl₃): δ 8.55 (d, J=4.7 Hz, 1H), 8.36 (d, J=2.7 Hz, 1H), 8.20 (dd, J=8.7, 4.6 Hz, 1H), 8.00 (s, 1H), 7.62 (t, J=7.7 Hz, 1H), 7.52 (m, 1H), 7.38 (d, J=7.8 Hz, 1H), 7.22-7.14 (m, 1H), 2.52 (d, J=10.7 Hz, 1H), 2.30-2.15 (m, 3H), 2.03 (d, J=10.7 Hz, 2H), 1.94 (dd, J=12.3, 6.7 Hz, 1H), 1.88-1.74 (m, 5H); ESI-MS m/z: 350 (M+H)⁺.

Example 21

5-methyl-N-((1R,5S)-5-(pyridin-2-ylethynyl)bicyclo[3.2.1]octan-1-yl)picolinamide ¹H NMR (500 MHz, CDCl₃): δ 8.54 (d, J=4.3 Hz, 1H), 8.34 (d, J=1.7 Hz, 1H), 8.12 (s, 1H), 8.05 (d, J=8.0 Hz, 1H), 7.67-7.59 (m, 2H), 7.37 (d, J=7.8 Hz, 1H), 7.18 (m, 1H), 2.53 (m, 1H), 2.39 (s, 3H), 2.29-2.15 (m, 3H), 2.04 (d, J=10.4 Hz, 2H), 1.93 (d, J=6.5 Hz, 1H), 1.80 (m, 5H); ESI-MS m/z: 346 (M+H)⁺.

Example 22

1-methyl-N-((1R,5S)-5-(pyridin-2-ylethynyl)bicyclo[3.2.1]octan-1-yl)-1H-pyrazole-3-carboxamide ¹H NMR (500 MHz, CDCl₃): δ 8.54 (m, 1H), 7.61 (m, 1H), 7.43-7.31 (m, 2H), 7.17 (m, 1H), 6.94 (s, 1H), 6.75 (d, J=2.3

Hz, 1H), 3.91 (s, 3H), 2.47 (m, 1H), 2.31-2.11 (m, 3H), 2.08-1.95 (m, 2H), 1.94-1.68 (m, 6H). ESI-MS m/z: 335 (M+H)⁺.

Example 23

3-fluoro-N-((1R,5S)-5-(pyridin-2-ylethynyl)bicyclo[3.2.1]octan-1-yl)picolinamide $^1$H NMR (500 MHz, CDCl$_3$): δ 8.55 (m, 1H), 8.35 (m, 1H), 7.97 (s, 1H), 7.61 (m, 1H), 7.54 (m 1H), 7.46 (m, 1H), 7.37 (m, 1H), 7.18 (m, 1H), 2.53 (m, 1H), 2.29-2.17 (m, 3H), 2.08-2.01 (m, 2H), 1.98-1.69 (m, 6H). ESI-MS m/z: 350 (M+H)⁺.

Examples 24-33 of table 1 were prepared analogously to Example 14 from intermediate 2-B and corresponding commercially available carboxylic acids at ~0.05-1.0 mmol reaction scales. Their $^1$H NMR and ESI-MS m/z are the same as their corresponding enantiomers, examples 14-23, respectively.

Examples 34 and 35 of table 1 were prepared analogously to Example 14 from intermediate 3-A and corresponding commercially available carboxylic acids at ~0.3 to 1.0 mmol reaction scales.

Example 34

N-((1R,5S)-5-(((6-methylpyridin-2-yl)ethynyl)bicyclo[3.2.1]octan-1-yl)pyrazine-2-carboxamide $^1$H NMR (500 MHz, CDCl$_3$): δ 9.39 (d, J=1.4 Hz, 1H), 8.74 (d, J=2.5 Hz, 1H), 8.58-8.38 (m, 1H), 7.90 (s, 1H), 7.52 (m, 1H), 7.21 (d, J=7.8 Hz, 1H), 7.07 (d, J=7.7 Hz, 1H) 2.56-2.51 (m, 4H), 2.26-1.75 (m, 11H); ESI-MS m/z: 347 (M+H)⁺.

Example 35

N-((1R,5S)-4-((6-methylpyridin-2-yl)ethynyl)bicyclo[3.2.1]octan-1-yl)picolinamide $^1$H NMR (500 MHz, CDCl$_3$): δ 8.53 (dd, J=5.1, 1.6 Hz, 1H), 8.17 (d, J=7.4 Hz, 2H), 7.84 (m, 1H), 7.49-7.34 (m, 2H), 7.20 (d, J=7.7 Hz, 1H), 7.04 (d, J=7.8 Hz, 1H), 2.54-2.52 (m, 4H), 2.32-1.70 (m, 11H); ESI-MS m/z: 346 (M+H)⁺.

Examples 36 and 37 of table 1 were prepared analogously to Example 14 from intermediate 3-B and corresponding commercially available carboxylic acids at ~0.3 to 1.0 mmol reaction scales. Their $^1$H NMR and ESI-MS m/z are the same as their corresponding enantiomers, examples 34 and 35, respectively.

Examples 38 and 39 of table 1, N-((1R,5S)-5-((6-fluoropyridin-2-yl)ethynyl)bicyclo[3.2.1]octan-1-yl)pyrazine-2-carboxamide and N-((1S,5R)-5-((6-fluoropyridin-2-yl)ethynyl)bicyclo[3.2.1]octan-1-yl)pyrazine-2-carboxamide, were prepared analogously to Example 14 from commerically available pyrazine-2-carboxylic acid and intermediate 4-A or 4-B at ~0.5 mmol reaction scale, respectively $^1$H NMR (500 MHz, CDCl$_3$): δ 9.39 (d, J=1.5 Hz, 1H), 8.74 (d, J=2.5 Hz, 1H), 8.50 (dd, J=2.5, 1.5 Hz, 1H), 7.91 (s, 1H), 7.71 (m, 1H), 7.27-7.25 (m, 1H), 6.85 (dd, J=8.0, 2.0 Hz, 1H), 2.53 (m, 1H), 2.28-1.73 (m, 11H); ESI-MS m/z: 351 (M+H)⁺.

Examples 40 and 41 of table 1, N-((1R,5S)-5-((3-fluoropyridin-2-yl)ethynyl)bicyclo[3.2.1]octan-1-yl)pyrazine-2-carboxamide and N-((1S,5R)-5-((3-fluoropyridin-2-yl)ethynyl)bicyclo[3.2.1]octan-1-yl)pyrazine-2-carboxamide, were prepared analogously to Example 14 from commerically available pyrazine-2-carboxylic acid and intermediate 5-A or 5-B at ~0.5 mmol reaction scale, respectively. $^1$H NMR (500 MHz, CDCl$_3$): δ 9.39 (d, J=1.5 Hz, 1H), 8.74 (d, J=2.5 Hz, 1H), 8.50 (t, J=2.0 Hz, 1H), 8.36 (m, 1H), 7.99 (s, 1H), 7.39 (m, 1H), 7.22 (m, 1H), 2.54 (m, 1H), 2.30-1.76 (m, 11H); ESI-MS m/z: 351 (M+H)⁺.

Examples 42-46 of table 1 were prepared analogously to Example 14 from intermediate 6-A and corresponding commercially available carboxylic acids at ~0.05-1.0 mmol reaction scales.

Example 42

N-((1R,5S)-5-(pyrazin-2-ylethynyl)bicyclo[3.2.1]octan-1-yl)picolinamide $^1$H NMR (500 MHz, CDCl$_3$): δ 8.61 (d, J=1.5 Hz, 1H), 8.56-8.47 (m, 2H), 8.43 (d, J=2.6 Hz, 1H), 8.18 (m, 2H), 7.85 (m, 1H), 7.42 (m, 1H), 2.58 (m, 1H), 2.30-1.75 (m, 11H); ESI-MS m/z: 333 (M+H)⁺.

Example 43

6-methyl-N-((1R,5S)-5-(pyrazin-2-ylethynyl)bicyclo[3.2.1]octan-1-yl)picolinamide $^1$H NMR (500 MHz, CDCl$_3$): δ 8.61 (d, J=1.5 Hz, 1H), 8.50 (dd, J=2.6, 1.6 Hz, 1H), 8.43 (d, J=2.6 Hz, 1H), 8.25 (s, 1H), 7.97 (d, J=7.7 Hz, 1H), 7.71 (t, J=7.7 Hz, 1H), 7.27-7.25 (m, 1H), 2.57 (m, 4H), 2.33-2.13 (m, 3H), 2.11-1.73 (m, 8H); ESI-MS m/z: 347 (M+H)⁺.

Example 44

1-methyl-N-((1R,5S)-5-(pyrazin-2-ylethynyl)bicyclo[3.2.1]octan-1-yl)-1H-pyrazole-3-carboxamide $^1$H NMR (500 MHz, CDCl$_3$): δ 8.60 (d, J=1.5 Hz, 1H), 8.50 (m, 1H), 8.43 (d, J=2.5 Hz, 1H), 7.35 (d, J=2.2 Hz, 1H), 6.93 (s, 1H), 6.76 (d, J=2.3 Hz, 1H), 3.91 (s, 3H), 2.51 (m, 1H), 2.30-1.68 (m, 11H); ESI-MS m/z: 336 (M+H)⁺.

Example 45

4-methyl-N-((1R,5S)-5-(pyrazin-2-ylethynyl)bicyclo[3.2.1]octan-1-yl)thiazole-2-carboxamide $^1$H NMR (500 MHz, CDCl$_3$): δ 8.61 (d, J=1.5 Hz, 1H), 8.50 (m, 1H), 8.43 (d, J=2.5 Hz, 1H), 7.31 (s, 1H), 7.10 (d, J=1.2 Hz, 1H), 2.54 (m, 1H), 2.47 (s, 3H), 2.33-1.66 (m, $^1$H); ESI-MS m/z: 353 (M+H)⁺.

Example 46

2-methyl-N-((1R,5S)-5-(pyrazin-2-ylethynyl)bicyclo[3.2.1]octan-1-yl)thiazole-4-carboxamide $^1$H NMR (500 MHz, CDCl$_3$): δ 8.60 (d, J=1.5 Hz, 1H), 8.50 (m, 1H), 8.43 (d, J=2.6 Hz, 1H), 7.89 (s, 1H), 7.42 (s, 1H), 2.70 (s, 3H), 2.53 (m, 1H), 2.30-1.73 (m, 11H); ESI-MS m/z: 353 (M+H)$^+$.

Examples of 47-51 of table 1 were prepared analogously to Example 14 from intermediate 6-B and corresponding commercially available carboxylic acids at ~0.1 mmol reaction scale. Their $^1$H NMR and ESI-MS m/z are the same as their corresponding enantiomers, examples 42-46, respectively.

Examples 52 and 53 of table 1, N-((1R,5S)-5-((2-methylthiazol-4-yl)ethynyl)bicyclo[3.2.1]octan-1-yl)pyrazine-2-carboxamide and N-((1S,5R)-5-((2-methylthiazol-4-yl)ethynyl)bicyclo[3.2.1]octan-1-yl)pyrazine-2-carboxamide, were prepared analogously to Example 14 from commerically available pyrazine-2-carboxylic acid and intermediate 7-A or 7-B at ~0.1 mmol reaction scale, respectively. $^1$H NMR (500 MHz, CDCl$_3$): δ 9.38 (d, J=1.4 Hz, 1H), 8.74 (d, J=2.5 Hz, 1H), 8.50 (m, 1H), 7.90 (s, 1H), 7.18 (s, 1H), 2.69 (s, 3H), 2.49 (m, 1H), 2.29-2.13 (m, 3H), 2.02 (m, 2H), 1.91 (d, J=8.4 Hz, 1H), 1.86-1.71 (m, 5H); ESI-MS m/z: 353 (M+H)$^+$.

Example 54

3-Chloro-N-[3-(6-methyl-pyrazin-2-ylethynyl)-adamantan-1-yl]-benzamide

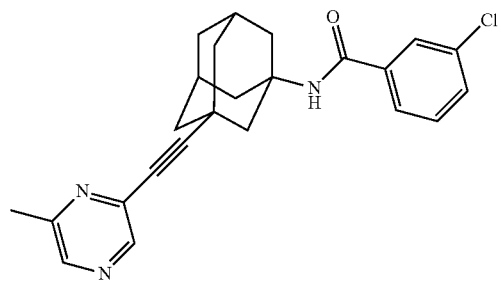 [SMILES: Cc1cncc(C#CC23CC4CC(C2)CC(NC(=O)c2cccc(Cl)c2)(C4)C3)n1]

Example 54 was prepared from intermediate 8 via the process of Scheme 3, supra, as follows:

To a stirred mixture of intermediate 8, 3-chloro-N-(3-ethynyl-adamantan-1-yl)-benzamide (60 mg, 0.19 mmol) and 2-chloro-6-methylpyrazine (60 mg, 0.47 mmol) in triethylamine (0.5 mL) and acetonitrile (2 mL) was added Pd(PPh$_3$)$_4$ (3 mg, 0.02 mmol), followed by an addition of CuI (3 mg, 0.016 mmol). After heated at 70° C. for three hours, the reaction mixture was cooled to room temperature, diluted with ethyl acetate (30 mL), washed with water (50 mL) and brine, dried over Na$_2$SO$_4$, and concentrated under reduced pressure. The resulting residue was purified by Prep HPLC to give 30 mg (38%) of the title compound, 3-chloro-N-[3-(6-methyl-pyrazin-2-ylethynyl)-adamantan-1-yl]-benzamide.
$^1$H NMR (500 MHz, CDCl$_3$): δ 8.57 (brs, 1H), 7.69 (t, J=2.0 Hz, 1H), 7.59 (d, J=8.0 Hz, 1H), 7.45 (d, J=8.0 Hz, 1H), 7.35 (t, J=8.0 Hz, 1H), 5.78 (s, 1H), 2.57 (s, 3H), 2.40 (s, 2H), 2.25 (s, 2H), 2.17-2.15 (m, 2H), 2.06-1.96 (m, 6H), 1.73-1.70 (m, 2H); ESI-MS m/z: 406 (M+H)$^+$.

Examples 55-60 of table 1 were prepared analogously to Example 54 from intermediates 8-10 and corresponding commercially available heteroaryl halides at ~0.2 mmol reaction scale, respectively.

Example 55

3-chloro-N-[3-(pyrazin-2-ylethynyl)-1-adamantyl]benzamide $^1$H NMR (500 MHz, CDCl$_3$): δ 8.77 (brs, 3H), 7.70 (t, J=2.0 Hz, 1H), 7.60-7.58 (m, 1H), 7.47-7.35 (m, 2H), 5.79 (s, 1H), 2.42 (s, 2H), 2.27 (s, 2H), 2.07-1.73 (m, 10H); ESI-MS m/z: 391 (M+H)$^+$.

Example 56

3-fluoro-N-[3-(6-methylpyrazin-2-ylethynyl)-1-adamantyl]benzamide $^1$H NMR (500 MHz, CDCl$_3$): δ 8.41 (s, 1H), 8.31 (s, 1H), 7.46-7.36 (m, 3H), 7.19-7.16 (m, 1H), 5.83 (s, 1H), 2.54 (s, 3H), 2.40 (s, 2H), 2.25 (s, 2H), 2.17-1.72 (m, 10H)); ESI-MS m/z: 390 (M+H)$^+$.

Example 57

3-fluoro-N-[3-(pyrazin-2-ylethynyl)-1-adamantyl]benzamide $^1$H NMR (500 MHz, CDCl$_3$): δ 8.59 (s, 1H), 8.49 (s, 1H), 8.43 (d, J=2.5 Hz, 1H), 7.47-7.17 (m, 4H), 5.86 (s, 1H), 2.41 (s, 2H), 2.26 (s, 2H), 2.19-1.79 (m, 10H); ESI-MS m/z: 376 (M+H)$^+$.

Example 58

6-methyl-N-[3-(pyridin-3-ylethynyl)-1-adamantyl]pyrazine-2-carboxamide $^1$H NMR (500 MHz, CDCl$_3$): δ 9.19 (s, 1H), 8.60 (brs, 3H), 7.71-7.66 (m, 2H), 7.27-7.24 (m, 1H), 2.61 (s, 3H), 2.40 (s, 2H), 2.27-1.62 (m, 12H); ESI-MS m/z: 373 (M+H)$^+$.

Example 59

6-methyl-N-[3-(pyridin-4-ylethynyl)-1-adamantyl]pyrazine-2-carboxamide $^1$H NMR (500 MHz, CDCl$_3$): δ 9.17 (s, 1H), 8.59 (brs, 3H), 7.70 (s, 1H), 7.72 (brs, 2H), 2.60 (s, 3H), 2.40 (s, 2H), 2.26-1.72 (m, 12H); ESI-MS m/z: 373 (M+H)$^+$.

Example 60

6-methyl-N-[3-(pyridin-2-ylethynyl)-1-adamantyl]pyrazine-2-carboxamide $^1$H NMR (500 MHz, CDCl$_3$): δ 9.18 (s, 1H), 8.60 (s, 1H), 8.55 (s, 1H), 7.70 (s, 1H), 7.62 (t, J=2.0 Hz, 1H), 7.38 (d, J=7.0 Hz, 1H), 7.19 (t, J=5.5 Hz, 1H), 2.60 (s, 3H), 2.41 (s, 2H), 2.26 (s, 2H), 2.20-1.72 (m, 10H); ESI-MS m/z: 373 (M+H)⁺.

Example 61

Pyridine-2-carboxylic acid (3-pyrazin-2-ylethynyl-adamantan-1-yl)-amide

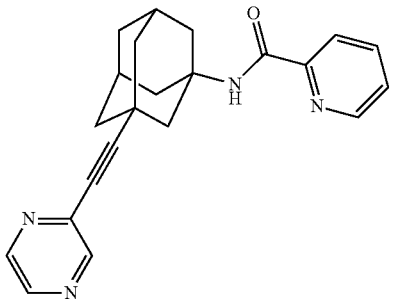 [SMILES: O=C(NC12CC3CC(CC(C#Cc4cnccn4)(C3)C1)C2)c1ccccn1]

Example 61 was prepared from intermediate 11 via the process of Scheme 4, supra, as follows:

To a solution of intermediate 11, 3-(pyrazin-2-ylethynyl)-1-adamantylamine (30 mg, 0.12 mmol) and picolinic acid (18 mg, 0.15 mmol) in DMF (2 mL) was added DIEA (50 mg, 0.38 mmol) and HATU (60 mg, 0.12 mmol) under $N_2$. After stirring at room temperature for an hour, the reaction was quenched with brine and extracted with ethyl acetate (2×20 mL). The combined organic phase was washed with brine, dried over $Na_2SO_4$, and concentrated under reduced pressure to give a residue, which was purified by Prep HPLC to give 50 mg (95%) of the title compound, pyridine-2-carboxylic acid (3-pyrazin-2-ylethynyl-adamantan-1-yl)-amide, as an off-white solid. ¹H NMR (500 MHz, CDCl₃): δ 8.60-8.43 (m, 4H), 8.17 (d, J=8.0 Hz, 1H), 7.96 (s, 1H), 7.85-7.82 (m, 1H), 7.42-7.39 (m, 1H), 2.45 (s, 2H), 2.26-2.20 (m, 4H), 2.11-1.97 (m, 6H), 1.76-1.69 (m, 2H); ESI-MS m/z: 359 (M+H)⁺.

Examples 62-81 of table 1 were prepared analogously to Example 61 from intermediates 11-17 and corresponding commercially available carboxylic acids at ~0.1-1.0 mmol reaction scales, respectively.

Example 62

5-fluoro-N-[3-(pyrazin-2-ylethynyl)-1-adamantyl] nicotinamide

¹H NMR (500 MHz, CDCl₃): δ 8.73-8.45 (m, 5H), 7.82 (d, J=8.0 Hz, 1H), 5.85 (s, 1H), 2.43 (s, 2H), 2.29 (s, 2H), 2.21-1.63 (m, 10H); ESI-MS m/z: 377 (M+H)⁺.

Example 63

2-methyl-N-[3-(pyrazin-2-ylethynyl)-1-adamantyl] pyrimidine-4-carboxamide

¹H NMR (500 MHz, CDCl₃): δ 8.86 (d, J=5.0 Hz, 1H), 8.60 (d, J=1.5 Hz, 1H), 8.50 (t, J=2.0 Hz, 1H), 8.44 (d, J=2.0 Hz, 1H), 7.91-7.88 (m, 2H), 2.78 (s, 3H), 2.43 (s, 2H), 2.28-1.63 (m, 12H); ESI-MS m/z: 374 (M+H)⁺.

Example 64

6-methyl-N-[3-(pyrazin-2-ylethynyl)-1-adamantyl] pyridine-2-carboxamide

¹H NMR (500 MHz, CDCl₃): δ 8.60 (d, J=1.6 Hz, 1H), 8.49 (t, J=2.1 Hz, 1H), 8.42 (d, J=2.5 Hz, 1H), 8.04 (s, 1H), 7.97 (d, J=7.7 Hz, 1H), 7.71 (t, J=7.7 Hz, 1H), 7.27 (s, 1H), 2.57 (s, 3H), 2.44 (s, 2H), 2.27 (m, 2H), 2.21-2.17 (m, 4H), 2.05-1.97 (m, 4H), 1.78-1.68 (m, 2H); ESI-MS m/z: 373 (M+H)⁺.

Example 65

5-fluoro-N-[3-(pyrazin-2-ylethynyl)-1-adamantyl] pyridine-2-carboxamide

¹H NMR (500 MHz, CDCl₃): δ 8.60 (s, 1H), 8.50 (s, 1H), 8.43 (d, J=2.7 Hz, 1H), 8.35 (d, J=2.9 Hz, 1H), 8.20 (m, 1H), 7.78 (s, 1H), 7.53 (m, 1H), 2.44 (s, 2H), 2.29-2.19 (m, 4H), 2.12-1.91 (m, 6H), 1.76-1.70 (m, 2H); ESI-MS m/z: 377 (M+H)⁺.

Example 66

1-methyl-N-[3-(pyrazin-2-ylethynyl)-1-adamantyl]-1H-pyrazole-3-carboxamide

¹H NMR (500 MHz, CDCl₃): δ 8.59 (d, J=1.7 Hz, 1H), 8.49 (t, J=2.1 Hz, 1H), 8.42 (d, J=2.5 Hz, 1H), 7.34 (d, J=2.2 Hz, 1H), 6.74 (d, J=2.2 Hz, 1H), 6.67 (s, 1H), 3.90 (s, 3H), 2.41 (s, 2H), 2.27-2.14 (m, 4H), 2.10-1.93 (m, 6H), 1.77-1.68 (m, 2H); ESI-MS m/z: 362 (M+H)⁺.

Example 67

3-cyano-N-[3-(pyrazin-2-ylethynyl)-1-adamantyl] benzamide

¹H NMR (500 MHz, CDCl₃): δ 8.60 (d, J=1.3 Hz, 1H), 8.50 (t, J=1.9 Hz, 1H), 8.43 (d, J=2.5 Hz, 1H), 8.03-7.93 (m, 2H), 7.76 (d, J=7.7 Hz, 1H), 7.56 (t, J=7.8 Hz, 1H), 5.90 (s, 1H), 2.42 (s, 2H), 2.28 (m, 2H), 2.20-2.18 (m, 2H), 2.08-1.96 (m, 6H), 1.73-1.70 (m, 2H); ESI-MS m/z: 383 (M+H)⁺.

Example 68

2-methyl-N-[3-(6-methylpyrazin-2-ylethynyl)-1-adamantyl]pyrimidine-4-carboxamide ¹H NMR (500 MHz, CDCl₃): δ 8.55 (d, J=5.0 Hz, 1H), 8.42 (s, 1H), 8.32 (s, 1H), 7.90-7.88 (m, 2H), 2.78 (s, 3H), 2.55 (s, 3H), 2.42 (s, 2H), 2.27 (s, 2H), 2.19-2.17 (m, 10H); ESI-MS m/z: 388 (M+H)⁺.

Example 69

N-[3-(6-methylpyrazin-2-ylethynyl)-1-adamantyl] pyridine-2-carboxamide

¹H NMR (500 MHz, CDCl₃): δ 8.52 (d, J=4.5 Hz, 1H), 8.41 (s, 1H), 8.31 (s, 1H), 8.17 (s, J=8.0 Hz, 1H), 7.96 (s, 1H), 7.86-7.82 (m, 1H), 7.42-7.40 (m, 1H), 2.55 (s, 3H), 2.44 (s, 2H), 2.26-1.72 (m, 12H); ESI-MS m/z: 373 (M+H)⁺.

Example 70

5-fluoro-N-[3-(6-methylpyrazin-2-ylethynyl)-1-adamantyl]nicotinamide

¹H NMR (500 MHz, CDCl₃): δ 8.71 (s, 1H), 8.59 (s, 1H), 8.42 (s, 1H), 8.33 (s, 1H), 7.82 (d, J=8.5 Hz, 1H), 5.88 (s, 1H), 2.55 (s, 3H), 2.42 (s, 2H), 2.28 (s, 2H), 2.19-1.65 (m, 10H); ESI-MS m/z: 391 (M+H)⁺.

Example 71

N-[3-(pyridin-2-ylethynyl)-1-adamantyl]pyrazine-2-carboxamide $^1$H NMR (500 MHz, CDCl$_3$): δ 9.38 (s, 1H), 8.73 (s, 1H), 8.54 (s, 1H), 8.50 (s, 1H), 7.68-7.58 (m, 2H), 7.36 (d, J=8.0 Hz, 1H), 7.18 (m, 1H), 2.41 (s, 2H), 2.29-2.09 (m, 6H), 2.07-1.95 (m, 4H), 1.77-1.67 (m, 2H); ESI-MS m/z: 359 (M+H)$^+$.

Example 72

N-[3-(pyridin-2-ylethynyl)-1-adamantyl]pyridine-2-carboxamide $^1$H NMR (500 MHz, CDCl$_3$): δ 8.48-8.42 (m, 2H), 8.09 (d, J=7.8 Hz, 1H), 7.89 (s, 1H), 7.76 (m, 1H), 7.53 (m, 1H), 7.36-7.27 (m, 2H), 7.09 (m, 1H), 2.35 (s, 2H), 2.21-2.01 (m, 6H), 1.99-1.87 (m, 4H), 1.67-1.60 (m, 2H); ESI-MS m/z: 358 (M+H)$^+$.

Example 73

6-methyl-N-[3-(pyridin-2-ylethynyl)-1-adamantyl]pyridine-2-carboxamide $^1$H NMR (500 MHz, CDCl$_3$): δ 8.53 (m, 1H), 8.03 (s, 1H), 7.97 (d, J=7.6 Hz, 1H), 7.70 (t, J=7.7 Hz, 1H), 7.60 (m, 1H), 7.36 (d, J=7.8 Hz, 1H), 7.26 (d, J=16.7 Hz, 1H), 7.17 (m, 1H), 2.56 (s, 3H), 2.41 (s, 2H), 2.30-2.12 (m, 6H), 2.06-1.94 (m, 4H), 1.78-1.66 (m, 2H). ESI-MS m/z: 372 (M+H)$^+$.

Example 74

2-methyl-N-[3-(pyridin-2-ylethynyl)-1-adamantyl]pyrimidine-4-carboxamide $^1$H NMR (500 MHz, CDCl$_3$): δ 8.84 (d, J=5.0 Hz, 1H), 8.54 (m, 1H), 7.92-7.86 (m, 2H), 7.61 (m, 1H), 7.36 (d, J=7.8 Hz, 1H), 7.18 (m, 1H), 2.77 (s, 3H), 2.39 (s, 2H), 2.27 (m, 2H), 2.27-2.25 (m, 2H), 2.15 (d, J=2.9 Hz, 4H), 2.06-1.95 (m, 4H). ESI-MS m/z: 373 (M+H)$^+$.

Example 75

N-[3-(pyridin-2-ylethynyl)-1-adamantyl]pyrimidine-4-carboxamide $^1$H NMR (500 MHz, CDCl$_3$): δ 9.21 (s, 1H), 8.96 (d, J=5.0 Hz, 1H), 8.56-8.51 (m, 1H), 8.09 (d, J=5.0 Hz, 1H), 7.86 (s, 1H), 7.61 (m, 1H), 7.36 (d, J=7.7 Hz, 1H), 7.18 (m, 1H), 2.40 (s, 2H), 2.26 (d, J=2.9 Hz, 2H), 2.20-2.07 (m, 4H), 2.06-1.95 (m, 4H), 1.75-1.69 (m, 2H); ESI-MS m/z: 359 (M+H)$^+$.

Example 76

1-methyl-N-[3-(pyridin-2-ylethynyl)-1-adamantyl]-1H-pyrazole-3-carboxamide $^1$H NMR (500 MHz, CDCl$_3$): δ 8.53 (d, J=5.1 Hz, 1H), 7.60 (t, J=7.8 Hz, 1H), 7.38-7.31 (m, 2H), 7.17 (m, 1H), 6.74 (d, J=2.7 Hz, 1H), 6.67 (s, 1H), 3.90 (s, 3H), 2.38 (s, 2H), 2.22-1.97 (m, 10H), 1.72-1.66 (m, 2H); ESI-MS m/z: 361 (M+H)$^+$.

Example 77

N-[3-(pyridin-2-ylethynyl)-1-adamantyl]isoxazole-5-carboxamide $^1$H NMR (500 MHz, CDCl$_3$): δ 8.54 (m, 1H), 8.31 (d, J=1.8 Hz, 1H), 7.61 (m, 1H), 7.36 (d, J=7.8 Hz, 1H), 7.18 (m, 1H), 6.87 (d, J=1.7 Hz, 1H), 6.30 (s, 1H), 2.38 (s, 2H), 2.25 (d, J=3.2 Hz, 2H), 2.16-2.14 (m, 2H), 2.07-1.94 (m, 6H), 1.71 (d, J=3.1 Hz, 2H); ESI-MS m/z: 348 (M+H)$^+$.

Example 78

N-[3-(6-methylpyridin-2-ylethynyl)-1-adamantyl]pyrazine-2-carboxamide $^1$H NMR (500 MHz, CDCl$_3$): δ 9.38 (d, J=1.5 Hz, 1H), 8.73 (d, J=2.5 Hz, 1H), 8.57-8.36 (m, 1H), 7.65 (s, 1H), 7.50 (t, J=7.8 Hz, 1H), 7.19 (d, J=7.8 Hz, 1H), 7.05 (d, J=7.7 Hz, 1H), 2.54 (s, 3H), 2.40 (s, 2H), 2.25 (d, J=3.1 Hz, 2H), 2.19-2.08 (m, 4H), 2.06-1.94 (m, 4H), 1.77-1.66 (m, 2H); ESI-MS m/z: 373 (M+H)$^+$.

Example 79

N-[3-(2-methylpyridin-4-ylethynyl)-1-adamantyl]pyrazine-2-carboxamide $^1$H NMR (500 MHz, CDCl$_3$): δ 9.39 (d, J=1.5 Hz, 1H), 8.74 (d, J=2.5 Hz, 1H), 8.49 (t, J=2.0 Hz, 1H), 8.40 (d, J=5.1 Hz, 1H), 7.66 (s, 1H), 7.13 (s, 1H), 7.04 (d, J=5.0 Hz, 1H), 2.52 (s, 3H), 2.39 (s, 2H), 2.30-2.06 (m, 6H), 2.02-1.91 (m, 4H), 1.77 (s, 2H); ESI-MS m/z: 373 (M+H)$^+$.

Example 80

N-[3-(6-methylpyridin-3-ylethynyl)-1-adamantyl]pyrazine-2-carboxamide $^1$H NMR (500 MHz, CDCl$_3$): δ9.39 (d, J=1.5 Hz, 1H), 8.73 (d, J=2.5 Hz, 1H), 8.49 (t, J=2.1 Hz, 2H), 7.66 (s, 1H), 7.55 (m, 1H), 7.07 (d, J=8.0 Hz, 1H), 2.54 (s, 3H), 2.39 (s, 2H), 2.26-2.08 (m, 6H), 2.03-1.91 (m, 4H), 1.72 (m, 2H); ESI-MS m/z: 373 (M+H)$^+$.

Example 81

1-methyl-N-[3-(4-methylthiazol-2-ylethynyl)-1-adamantyl]-1H-pyrazole-3-carboxamide $^1$H NMR (500 MHz, CDCl$_3$): δ7.40 (d, J=1.5 Hz, 1H), 7.33 (d, J=2.3 Hz, 1H), 6.74 (d, J=2.2 Hz, 1H), 6.65 (s, 1H), 3.90 (s, 3H), 2.46 (d, J=1.2 Hz, 3H), 2.37 (s, 2H), 2.27-1.83 (m, 12H); ESI-MS m/z: 381 (M+H)$^+$.

TABLE 1

Compounds of formula I

| Example No. | Structure | Chemical Name |
|---|---|---|
| 1 | 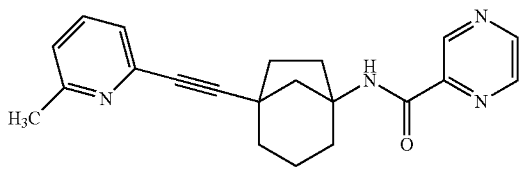 [SMILES: Cc1cccc(C#CC23CCCC(NC(=O)c4cnccn4)(CC2)C3)n1] | N-(5-(6-methylpyridin-2-yl)ethynyl)bicyclo[3.2.1]octan-1-yl)pyrazine-2-carboxamide |
| 2 | 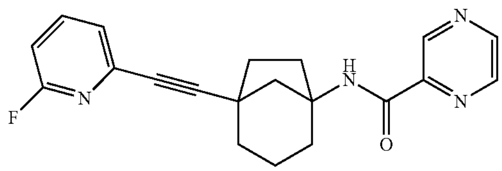 [SMILES: O=C(NC12CCCC(C#Cc3cccc(F)n3)(CC1)C2)c1cnccn1] | N-(5-((6-fluoropyridin-2-yl)ethynyl)bicyclo[3.2.1]octan-1-yl)pyrazine-2-carboxamide |
| 3 | 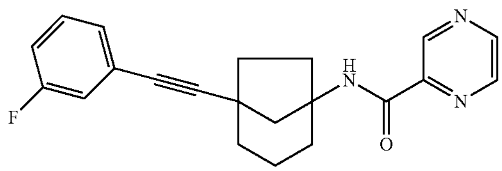 [SMILES: O=C(NC12CCCC(C#Cc3cccc(F)c3)(CC1)C2)c1cnccn1] | N-(5-((3-fluorophenyl)ethynyl)bicyclo[3.2.1]octan-1-yl)pyrazine-2-carboxamide |
| 4 | 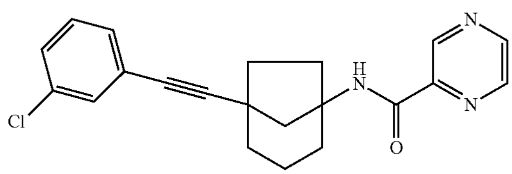 [SMILES: O=C(NC12CCCC(C#Cc3cccc(Cl)c3)(CC1)C2)c1cnccn1] | N-(5-((3-chlorophenyl)ethynyl)bicyclo[3.2.1]octan-1-yl)pyrazine-2-earboxamide |
| 5 | 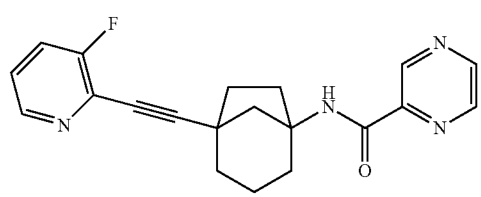 [SMILES: O=C(NC12CCCC(C#Cc3ncccc3F)(CC1)C2)c1cnccn1] | N-(5-((3-fluoropyridin-2-yl)ethynyl)bicyclo[3.2.1]octan-1-yl)pyrazine-2-carboxamide |
| 6 | 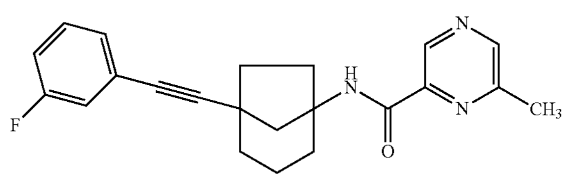 [SMILES: Cc1cncc(C(=O)NC23CCCC(C#Cc4cccc(F)c4)(CC2)C3)n1] | N-(5-((3-fluorophenyl)ethynyl)bicyclo[3.2.1]octan-1-yl)-6-methylpyrazine-2-carboxamide |
| 7 | 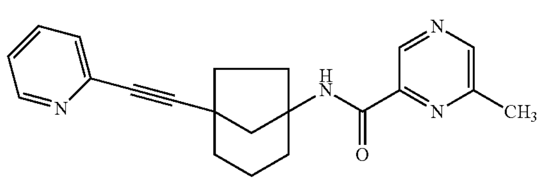 [SMILES: Cc1cncc(C(=O)NC23CCCC(C#Cc4ccccn4)(CC2)C3)n1] | 6-methyl-N-(5-(pyridin-2-ylethynyl)bicyclo[3.2.1]octan-1-yl)pyrazine-2-carboxamide |
| 8 | 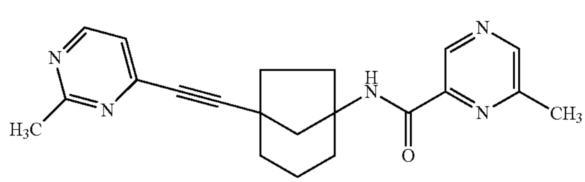 | 6-methyl-N-(5-((2-methylpyrimidin-4-yl)ethynyl)bicyclo[3.2.1]octan-1-yl)pyrazine-2-carboxamide |

TABLE 1-continued

Compounds of formula I

| Example No. | Structure | Chemical Name |
|---|---|---|
| 9 | 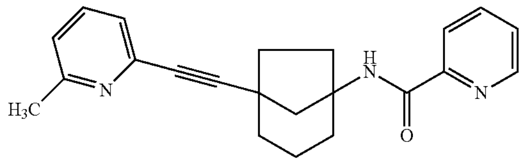 [SMILES: Cc1cccc(C#CC23CCCC(NC(=O)c4ccccn4)(CC2)C3)n1] | N-(5-((6-methylpyridin-2-yl)ethynyl)bicyclo[3.2.1]octan-1-yl)picolinamide |
| 10 | 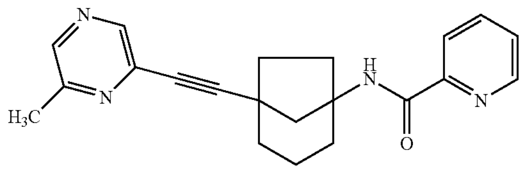 [SMILES: Cc1cncc(C#CC23CCCC(NC(=O)c4ccccn4)(CC2)C3)n1] | N-(5-((6-methylpyrazin-2-yl)ethynyl)bicyclo[3.2.1]octan-1 yl)picolinamide |
| 11 | 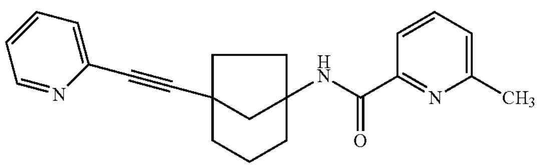 [SMILES: Cc1cccc(C(=O)NC23CCCC(C#Cc4ccccn4)(CC2)C3)n1] | 6-methyl-N-(5-(pyridin-2-ylethynyl)bicyclo[3.2.1]octan-1-yl)picolinamide |
| 12 | 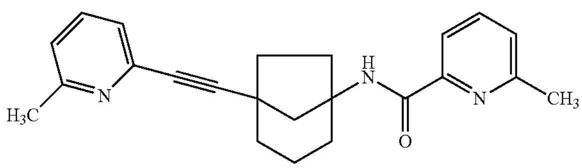 | 6-methyl-N-(5-((6-methylpyridin-2-yl)ethynyl)bicyclo[3.2.1]octan-1-yl)picolinamide |
| 13 | 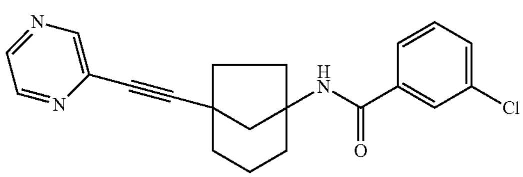 [SMILES: O=C(NC12CCCC(C#Cc3cnccn3)(CC1)C2)c1cccc(Cl)c1] | 3-chloro-N-[5-(pyrazin-2-ylethynyl)bicyclo[3.2.1]oct-1-yl]benzamide |
| 14 | 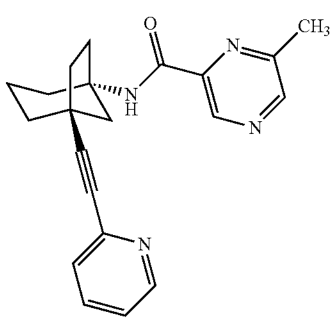 | 6-methyl-N-((1R,5S)-5-(pyridin-2-ylethynyl)bicyclo[3.2.1]octan-1-yl)pyrazine-2-carboxamide |
| 15 | 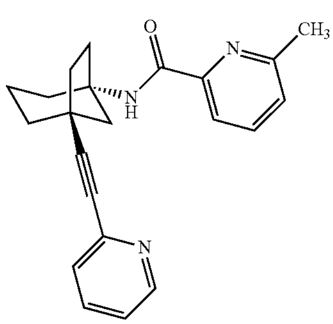 | 6-methyl-N-((1R,5S)-5-(pyridin-2-ylethynl)bicyclo[3.2.1]octan-1-yl)picolinamide |

TABLE 1-continued

Compounds of formula I

| Example No. | Structure | Chemical Name |
|---|---|---|
| 16 | 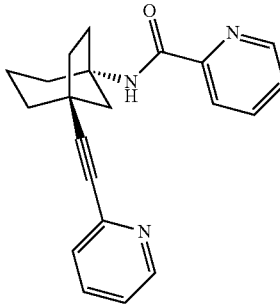 | N-((1R,5S)-5-(pyridin-2-ylethynyl)bicyclo[3.2.1]octan-1-yl)picolinamide |
| 17 | 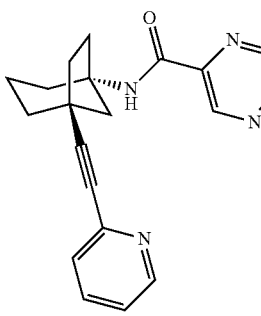 | N-((1R,5S)-5-pyridin-2-ylethynyl)bicyclo[3.2.1]octan-1-yl)pyrazine-2-carboxamide |
| 18 | 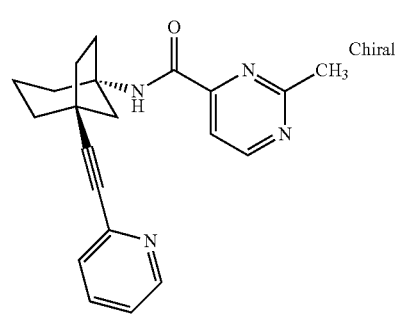 [SMILES: Cc1nccc(C(=O)N[C@]23CCC[C@](C#Cc4ccccn4)(CC2)C3)n1] | 2-methyl-N-((1R,5S)-5-(pyridin-2-ylethynyl)bicyclo[3.2.1]octan-1-yl)pyrimidine-4-carboxamide |
| 19 | 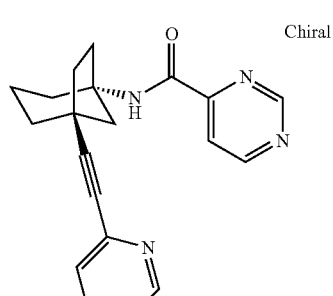 | N-((1R,5S)-5-(pyridin-2-ylethynyl)bicyclo[3.2.1]octan-1-yl)pyrimidine-4-carboxamide |
| 20 | 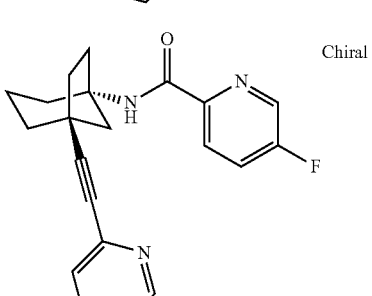 | 5-fluoro-N-((1R,5S)-5-(pyridin-2-ylethynyl)bicyclo[3.2.1]octan-1-yl)picolinamide |

TABLE 1-continued
Compounds of formula I
| Example No. | Structure | Chemical Name |
|---|---|---|
| 21 | 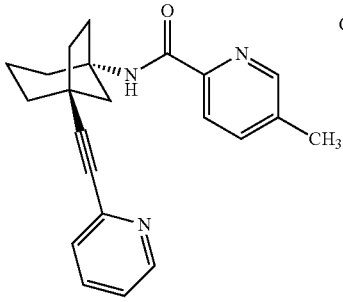 | 5-methyl-N-((1R,5S)-5-(pyridin-2-ylethynyl)bicyclo[3.2.1]octan-1-yl)picolinamide |
| 22 | 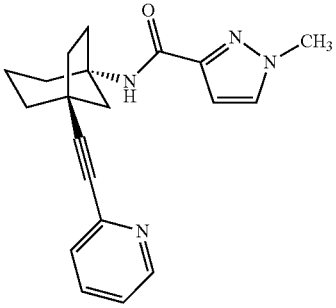 | 1-methyl-N-((1R,5S)-5-(pyridin-2-ylethynyl)bicyclo[3.2.1]octan-1-yl)-1H-pyrazole-3-carboxamide |
| 23 | 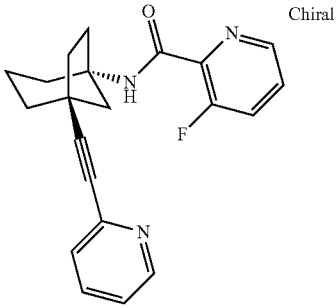 [SMILES: O=C(N[C@]12CCC[C@](C#Cc3ccccn3)(CC1)C2)c1ncccc1F] | 3-fluoro-N-((1R,5S)-5-(pyridin-2-ylethynyl)bicyclo[3.2.1]octan-1-yl)picolinamide |
| 24 | 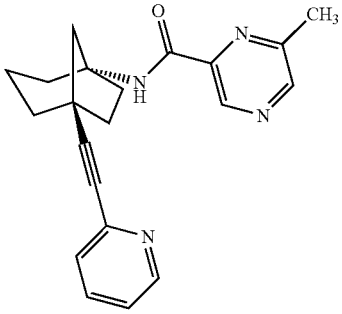 | 6-methyl-N-((1S,5R)-5-(pyridin-2-ylethynyl)bicyclo[3.2.1]octan-1-yl)pyrazine-2-carboxamide |

TABLE 1-continued
Compounds of formula I
| Example No. | Structure | Chemical Name |
|---|---|---|
| 25 | 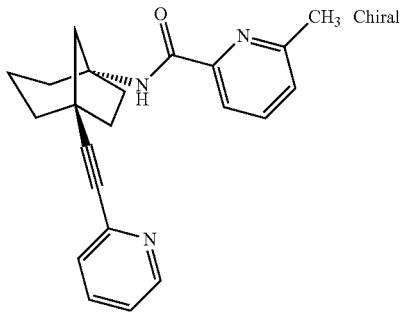 [SMILES: Cc1cccc(C(=O)N[C@@]23CCC[C@@](C#Cc4ccccn4)(CC2)C3)n1] | 6-methyl-N-((1S,5R)-5-(pyridin-2-ylethynyl)bicyclo[3.2.1]octan-1-yl)picolinamide |
| 26 | 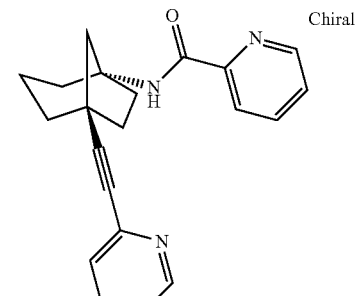 | N-((1S,5R)-5-(pyridin-2-ylethynyl)bicyclo[3.2.1]octan-1-yl)picolinamide |
| 27 | 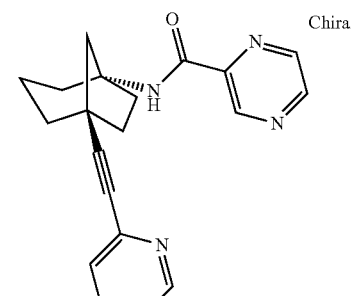 | N-((1S,5R)-5-(pyridin-2-ylethynyl)bicyclo[3.2.1]octan-1-yl)pyrazine-2-carboxamide |
| 28 | 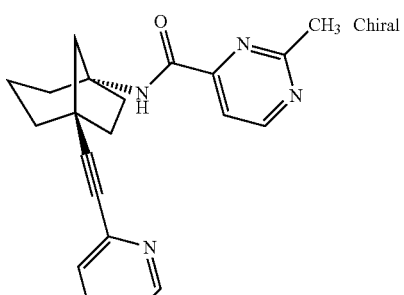 | 2-methyl-N-((1S,5R)-5-(pyridin-2-ylethynyl)bicyclo[3.2.1]octan-1-yl)pyrimidine-4-carboxamide |

TABLE 1-continued
Compounds of formula I
| Example No. | Structure | Chemical Name |
|---|---|---|
| 29 | 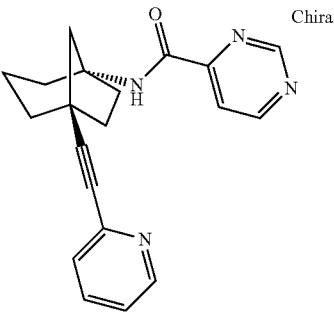 | N-((1S,5R)-5-(pyridin-2-ylethynyl)bicyclo[3.2.1]octan-1-yl)pyrimidine-4-carboxamide |
| 30 | 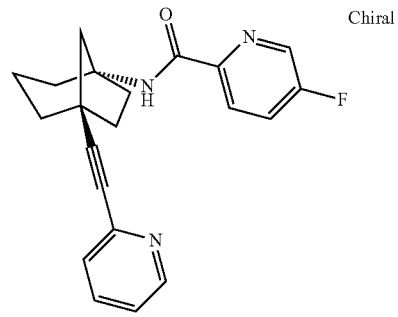 [SMILES: O=C(N[C@@]12CCC[C@@](C#Cc3ccccn3)(CC1)C2)c1ccc(F)cn1] | 5-fluoro-N-((1S,5R)-5-(pyridin-2-ylethynyl)bicyclo[3.2.1]octan-1-yl)picolinamide |
| 31 | 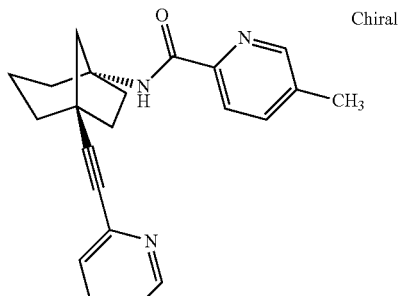 | 5-methyl-N-((1S,5R)-5-(pyridin-2-ylethynyl)bicyclo[3.2.1]octan-1-yl)picolinamide |
| 32 | 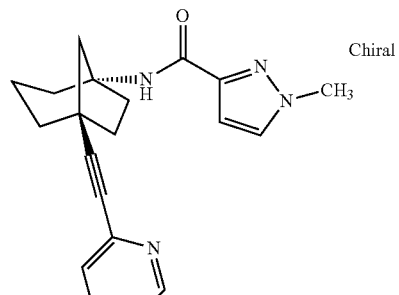 | 1-methyl-N-((1S,5R)-5-(pyridin-2-ylethynyl)bicyclo[3.2.1]octan-1-yl)-1H-pyrazole-3-carboxamide |

TABLE 1-continued
Compounds of formula I
| Example No. | Structure | Chemical Name |
|---|---|---|
| 33 | 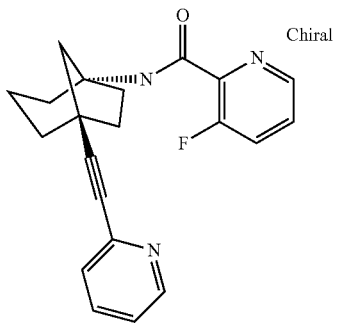 [SMILES: O=C(N[C@@]12CCC[C@@](C#Cc3ccccn3)(CC1)C2)c1ncccc1F] | 3-fluoro-N-((1S,5R)-5-(pyridin-2-ylethynyl)bicyclo[3.2.1]octan-1-yl)picolinamide |
| 34 | 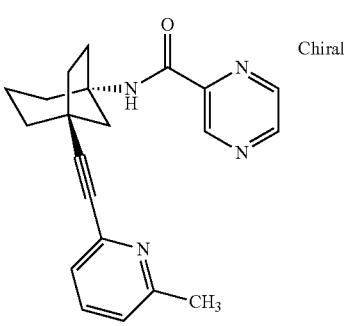 [SMILES: Cc1cccc(C#C[C@@]23CCC[C@@](NC(=O)c4cnccn4)(CC2)C3)n1] | N-((1R,5S)-5-((6-methylpyridin-2-yl)ethynyl)bicyclo[3.2.1]octan-1-yl)pyrazine-2-carboxamide |
| 35 | 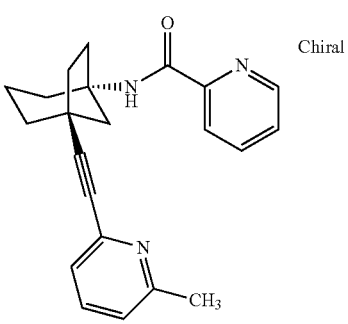 [SMILES: Cc1cccc(C#C[C@@]23CCC[C@@](NC(=O)c4ccccn4)(CC2)C3)n1] | N-((1R,5S)-5-((6-methylpyridin-2-yl)ethynyl)bicyclo[3.2.1]octan-1-yl)picolinamide |
| 36 | 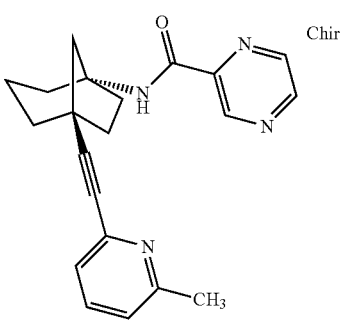 | N-((1S,5R)-5-((6-methylpyridin-2-yl)ethynyl)bicyclo[3.2.1]octan-1-yl)pyrazine-2-carboxamide |

TABLE 1-continued
Compounds of formula I
| Example No. | Structure | Chemical Name |
|---|---|---|
| 37 | 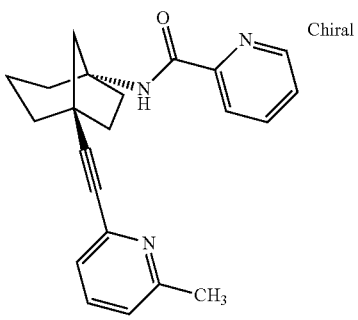 [SMILES: Cc1cccc(C#C[C@]23CCC[C@](NC(=O)c4ccccn4)(CC2)C3)n1] | N-((1S,5R)-5-((6-methylpyridin-2-yl)ethynyl)bicyclo[3.2.1]octan-1-yl)picolinamide |
| 38 | 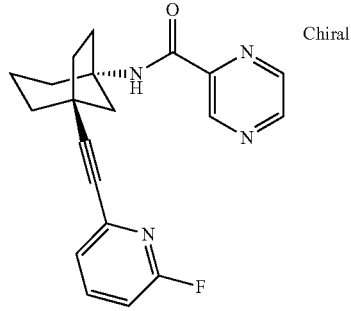 [SMILES: O=C(N[C@]12CCC[C@](C#Cc3cccc(F)n3)(CC1)C2)c1cnccn1] | N-((1R,5S)-5-((6-fluoropyridin-2-yl)ethynyl)bicyclo[3.2.1]octan-1-yl)pyrazine-2-carboxamide |
| 39 | 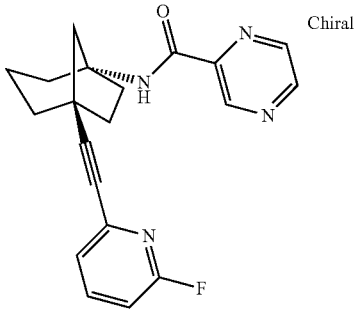 [SMILES: O=C(N[C@@]12CCC[C@@](C#Cc3cccc(F)n3)(CC1)C2)c1cnccn1] | N-((1S,5R)-5-((6-fluoropyridin-2-yl)ethynyl)bicyclo[3.2.1]octan-1-yl)pyrazine-2-carboxamide |
| 40 | 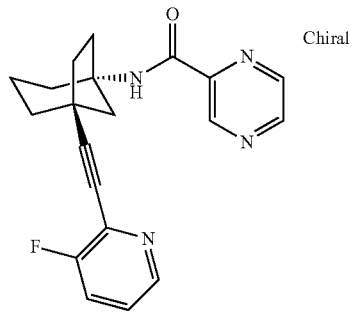 [SMILES: O=C(N[C@]12CCC[C@](C#Cc3ncccc3F)(CC1)C2)c1cnccn1] | N-((1R,5S)-5-((3-fluoropyridin-2-yl)ethynyl)bicyclo[3.2.1]octan-1-yl)pyrazine-2-carboxamide |

TABLE 1-continued
Compounds of formula I
| Example No. | Structure | Chemical Name |
|---|---|---|
| 41 | 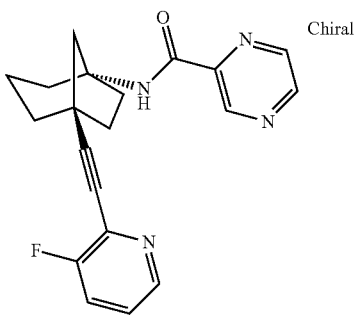 [SMILES: O=C(N[C@@]12CCC[C@@](C#Cc3ncccc3F)(CC1)C2)c1cnccn1] | N-((1S,5R)-5-((3-fluoropyridin-2-yl)ethynyl)bicyclo[3.2.1]octan-1-yl)pyrazine-2-carboxamide |
| 42 | 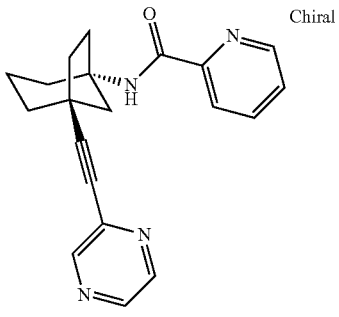 [SMILES: O=C(N[C@]12CCC[C@](C#Cc3cnccn3)(CC1)C2)c1ccccn1] | N-((1R,5S)-5-(pyrazin-2-ylethynyl)bicyclo[3.2.1]octan-1-yl)picolinamide |
| 43 | 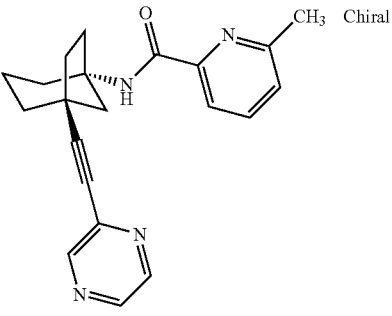 [SMILES: Cc1cccc(C(=O)N[C@]23CCC[C@](C#Cc4cnccn4)(CC2)C3)n1] | 6-methyl-N-((1R,1S)-5-(pyrazin-2-ylethynyl)bicyclo[3.2.1]octan-1-yl)picolinamide |
| 44 | 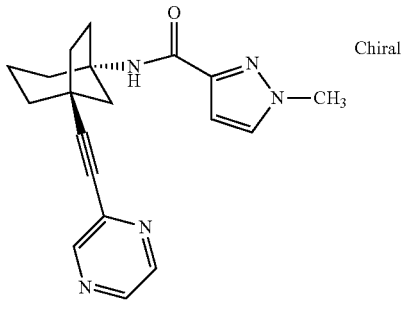 [SMILES: Cn1ccc(C(=O)N[C@]23CCC[C@](C#Cc4cnccn4)(CC2)C3)n1] | 1-methyl-N-((1R,5S)-5-(pyrazin-2-ylethynyl)bicyclo[3.2.1]octan-1-yl)-1H-pyrazole-3-carboxamide |

TABLE 1-continued
Compounds of formula I
| Example No. | Structure | Chemical Name |
|---|---|---|
| 45 | 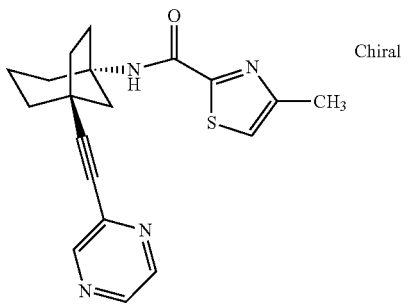 [SMILES: Cc1csc(C(=O)N[C@]23CCC[C@](C#Cc4cnccn4)(CC2)C3)n1] | 4-methyl-N-((1R,5S)-5-(pyrazin-2-ylethynyl)bicyclo[3.2.1]octan-1-yl)thiazole-2-carboxamide |
| 46 | 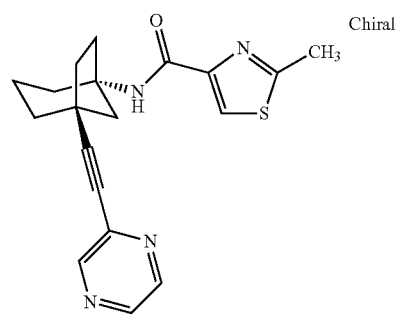 [SMILES: Cc1nc(C(=O)N[C@]23CCC[C@](C#Cc4cnccn4)(CC2)C3)cs1] | 2-methyl-N-((1R,5S)-5-(pyrazin-2-ylethynyl)bicyclo[3.2.1]octan-1-yl)thiazole-4-carboxamide |
| 47 | 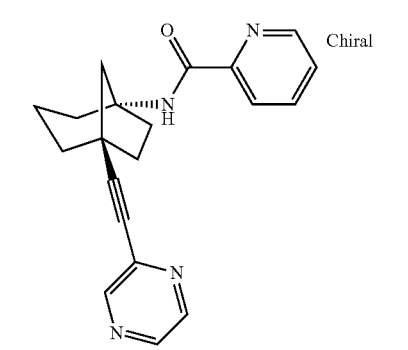 [SMILES: O=C(N[C@@]12CCC[C@@](C#Cc3cnccn3)(CC1)C2)c1ccccn1] | N-((1S,5R)-5-(pyrazin-2-ylethynyl)bicyclo[3.2.1]octan-1-yl)picolinamide |
| 48 | 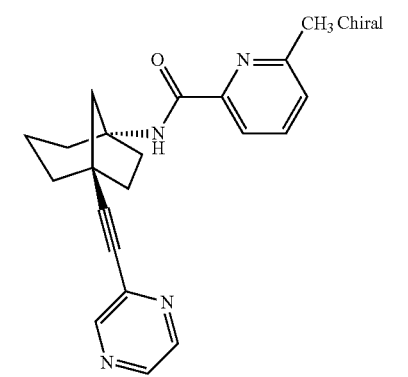 [SMILES: Cc1cccc(C(=O)N[C@@]23CCC[C@@](C#Cc4cnccn4)(CC2)C3)n1] | 6-methyl-N-((1S,5R)-5-(pyrazin-2-ylethynyl)bicyclo[3.2.1]octan-1-yl)picolinamide |

TABLE 1-continued
Compounds of formula I
| Example No. | Structure | Chemical Name |
|---|---|---|
| 49 | 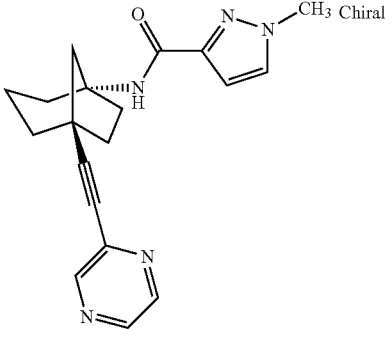 [SMILES: Cn1ccc(C(=O)N[C@@]23CCC[C@@](C#Cc4cnccn4)(CC2)C3)n1] | 1-methyl-N-((1S,5R)-5-(pyrazin-2-ylethynyl)bicyclo[3.2.1]octan-1-yl)-1H-pyrazole-3-carboxamide |
| 50 | 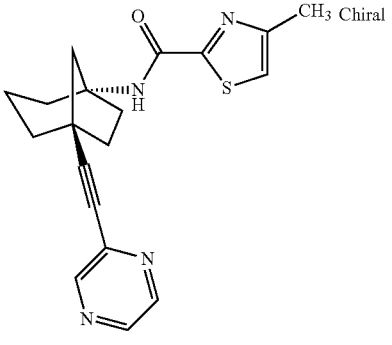 [SMILES: Cc1csc(C(=O)N[C@@]23CCC[C@@](C#Cc4cnccn4)(CC2)C3)n1] | 4-methyl-N-((1S,5R)-5-(pyrazin-2-ylethynyl)bicyclo[3.2.1]octan-1-yl)thiazole-2-carboxamide |
| 51 | 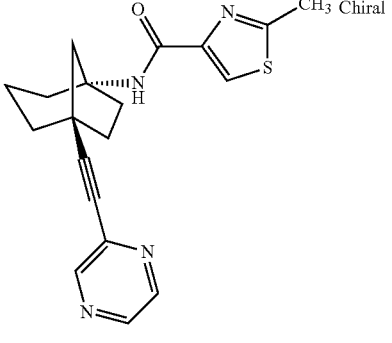 | 2-methyl-N-((1S,5R)-5-(pyrazin-2-ylethynyl)bicyclo[3.2.1]octan-1-yl)thiazole-4-carboxamide |
| 52 | 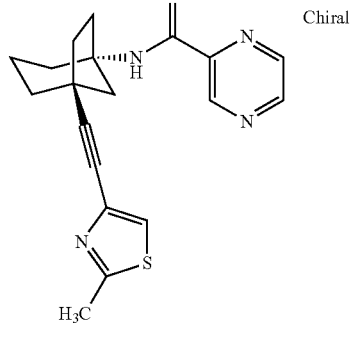 | N-((1R,5S)-5-((2-methylthiazol-4-yl)ethynyl)bicyclo[3.2.1]octan-1-yl)pyrazine-2-carboxamide |

TABLE 1-continued

Compounds of formula I

| Example No. | Structure | Chemical Name |
|---|---|---|
| 53 | 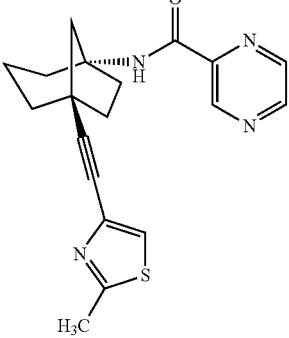 Chiral | N-((1S,5R)-5-((2-methylthiazol-4-yl)ethynyl)bicyclo[3.2.1]octan-1-yl)pyrazine-2-carboxamide |
| 54 | 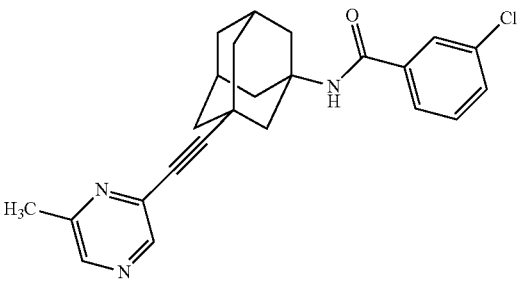 [SMILES: Cc1cncc(C#CC23CC4CC(C2)CC(NC(=O)c2cccc(Cl)c2)(C4)C3)n1] | 3-chloro-N-[3-(6-methylpyrazin-2-ylethynyl)-1-adamantyl]benzamide |
| 55 | 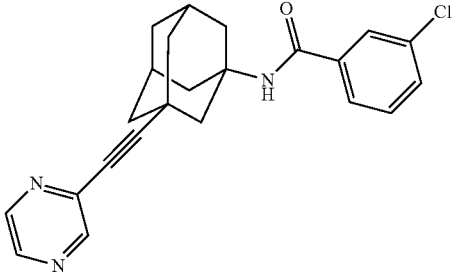 [SMILES: O=C(NC12CC3CC(CC(C#Cc4cnccn4)(C3)C1)C2)c1cccc(Cl)c1] | 3-chloro-N-[3-(pyrazin-2-ylethynyl)-1-adamantyl]benzamide |
| 56 | 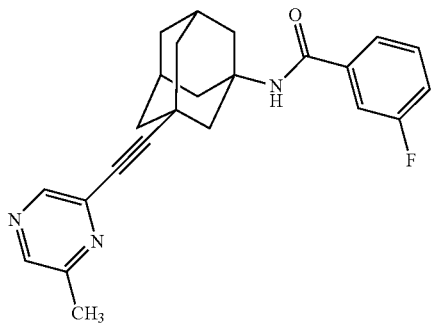 [SMILES: Cc1cncc(C#CC23CC4CC(C2)CC(NC(=O)c2cccc(F)c2)(C4)C3)n1] | 3-fluoro-N-[3-(6-methylpyrazin-2-ylethynyl)-1-adamantyl]benzamide |
| 57 | 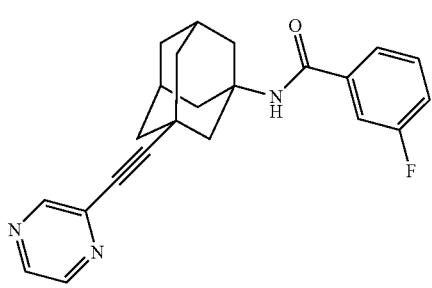 [SMILES: O=C(NC12CC3CC(CC(C#Cc4cnccn4)(C3)C1)C2)c1cccc(F)c1] | 3-fluoro-N-[3-(pyrazin-2-ylethynyl)-1-adamantyl]benzamide |

TABLE 1-continued

Compounds of formula I

| Example No. | Structure | Chemical Name |
|---|---|---|
| 58 | 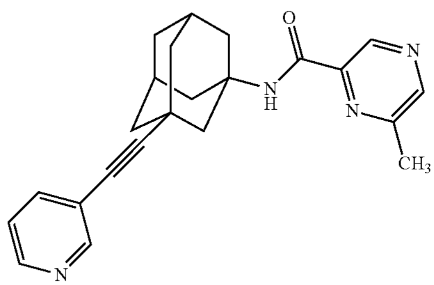 [SMILES: Cc1cncc(C(=O)NC23CC4CC(CC(C#Cc5cccnc5)(C4)C2)C3)n1] | 6-methyl-N-[3-(pyridin-3-ylethynyl)-1-adamantyl]pyrazine-2-carboxamide |
| 59 | 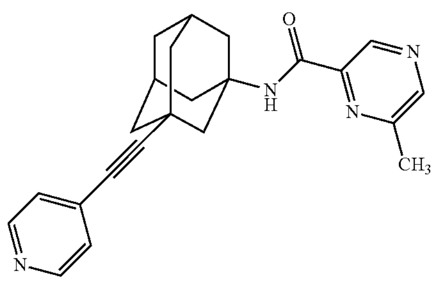 [SMILES: Cc1cncc(C(=O)NC23CC4CC(CC(C#Cc5ccncc5)(C4)C2)C3)n1] | 6-methyl-N-[3-(pyridin-4-ylethynyl)-1-adamantyl]pyrazine-2-carboxamide |
| 60 | 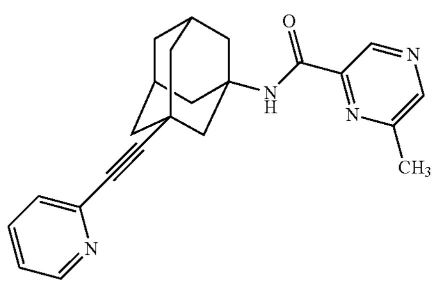 [SMILES: Cc1cncc(C(=O)NC23CC4CC(CC(C#Cc5ccccn5)(C4)C2)C3)n1] | 6-methyl-N-[3-(pyridin-2-ylethynyl)-1-adamantyl]pyrazine-2-carboxamide |
| 61 | 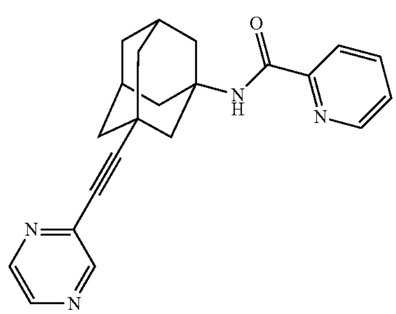 [SMILES: O=C(NC12CC3CC(CC(C#Cc4cnccn4)(C3)C1)C2)c1ccccn1] | N-[3-(pyrazin-2-ylethynyl)-1-adamantyl]pyridine-2-carboxamide |
| 62 | 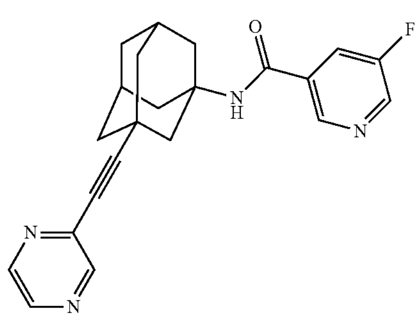 [SMILES: O=C(NC12CC3CC(CC(C#Cc4cnccn4)(C3)C1)C2)c1cncc(F)c1] | 5-fluoro-N-[3-(pyrazin-2-ylethynyl)-1-adamantyl]nicotinamide |

TABLE 1-continued

Compounds of formula I

| Example No. | Structure | Chemical Name |
|---|---|---|
| 63 | 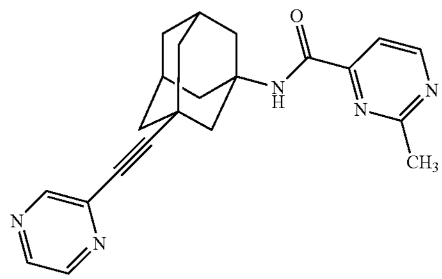 [SMILES: Cc1nccc(C(=O)NC23CC4CC(CC(C#Cc5cnccn5)(C4)C2)C3)n1] | 2-methyl-N-[3-(pyrazin-2-ylethynyl)-1-adamantyl]pyrimidine-4-carboxamide |
| 64 | 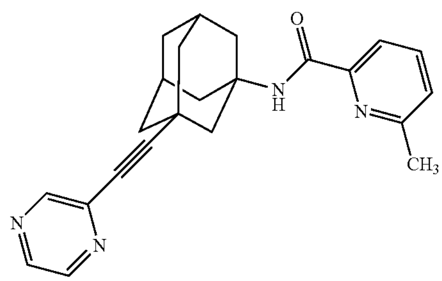 [SMILES: Cc1cccc(C(=O)NC23CC4CC(CC(C#Cc5cnccn5)(C4)C2)C3)n1] | 6-methyl-N-[3-(pyrazin-2-ylethynyl)-1-adamantyl]pyridine-2-carboxamide |
| 65 | 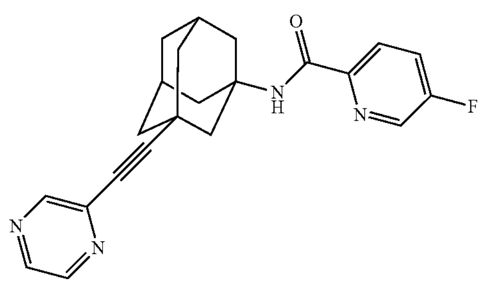 [SMILES: O=C(NC12CC3CC(CC(C#Cc4cnccn4)(C3)C1)C2)c1ccc(F)cn1] | 5-fluoro-N-[3-(pyrazin-2-ylethynyl)-1-adamantyl]pyridine-2-carboxamide |
| 66 | 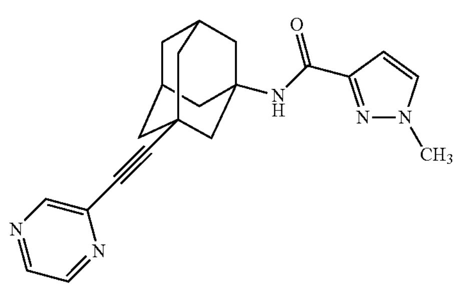 [SMILES: Cn1ccc(C(=O)NC23CC4CC(CC(C#Cc5cnccn5)(C4)C2)C3)n1] | 1-methyl-N-[3-(pyrazin-2-ylethynyl)-1-adamantyl]-1H-pyrazole-3-carboxamide |
| 67 | 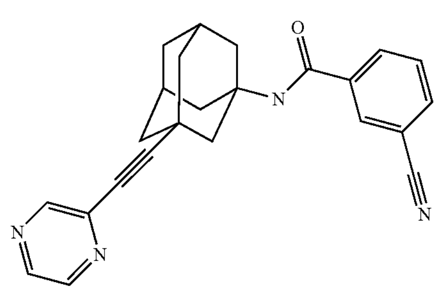 [SMILES: N#Cc1cccc(C(=O)NC23CC4CC(CC(C#Cc5cnccn5)(C4)C2)C3)c1] | 3-cyano-N-[3-(pyrazin-2-ylethynyl)-1-adamantyl]benzamide |

TABLE 1-continued

Compounds of formula I

| Example No. | Structure | Chemical Name |
|---|---|---|
| 68 | 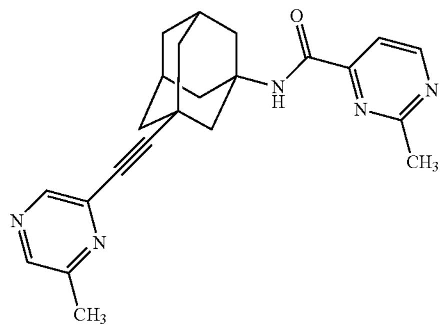 [SMILES: Cc1cncc(C#CC23CC4CC(C2)CC(NC(=O)c2ccnc(C)n2)(C4)C3)n1] | 2-methyl-N-[3-(6-methylpyrazin-2-ylethynyl)-1-adamantyl]pyrimidine-4-carboxamide |
| 69 | 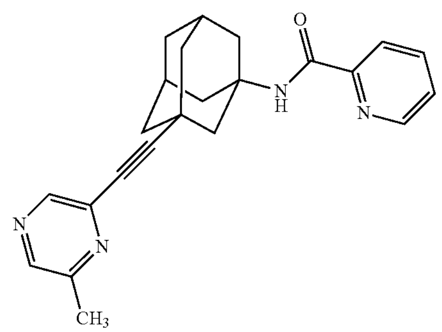 [SMILES: Cc1cncc(C#CC23CC4CC(C2)CC(NC(=O)c2ccccn2)(C4)C3)n1] | N-[3-(6-methylpyrazin-2-ylethynyl)-1-adamantyl]pyridine-2-carboxamide |
| 70 | 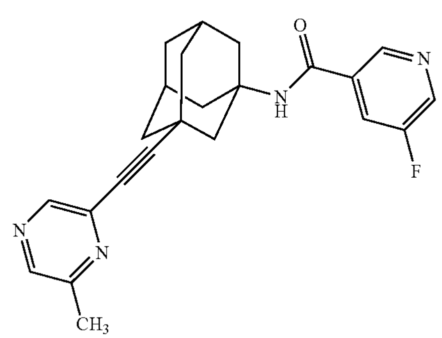 [SMILES: Cc1cncc(C#CC23CC4CC(C2)CC(NC(=O)c2cncc(F)c2)(C4)C3)n1] | 5-fluoro-N-[3-(6-methylpyrazin-2-ylethynyl)-1-adamantyl]nicotinamide |
| 71 | 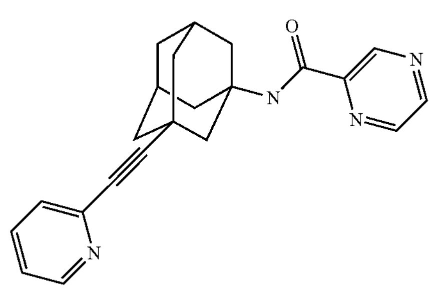 [SMILES: O=C(NC12CC3CC(CC(C#Cc4ccccn4)(C3)C1)C2)c1cnccn1] | N-[3-(pyridin-2-ylethynyl)-1-adamantyl]pyrazine-2-carboxamide |

TABLE 1-continued

Compounds of formula I

| Example No. | Structure | Chemical Name |
|---|---|---|
| 72 | 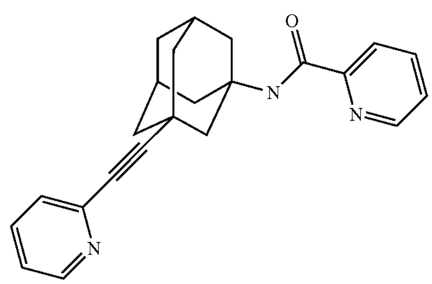 [SMILES: O=C(NC12CC3CC(CC(C#Cc4ccccn4)(C3)C1)C2)c1ccccn1] | N-[3-(pyridin-2-ylethynyl)-1-adamantyl]pyridine-2-carboxamide |
| 73 | 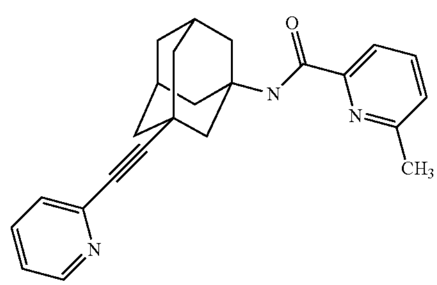 | 6-methyl-N-[3-(pyridin-2-ylethynyl)-1-adamantyl]pyridine-2-carboxamide |
| 74 | 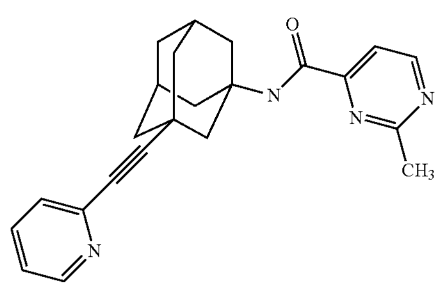 [SMILES: Cc1nccc(C(=O)NC23CC4CC(CC(C#Cc5ccccn5)(C4)C2)C3)n1] | 2-methyl-N-[3-(pyridin-2-ylethynyl)-1-adamantyl]pyrimidine-4-carboxamide |
| 75 | 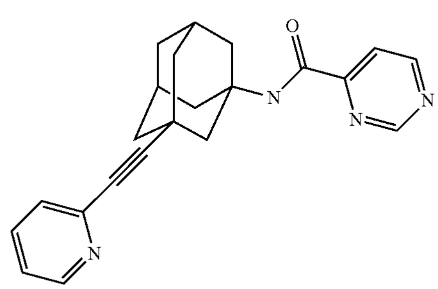 [SMILES: O=C(NC12CC3CC(CC(C#Cc4ccccn4)(C3)C1)C2)c1ccncn1] | N-[3-(pyridin-2-ylethynyl)-1-adamantyl]pyrimidine-4-carboxamide |
| 76 | 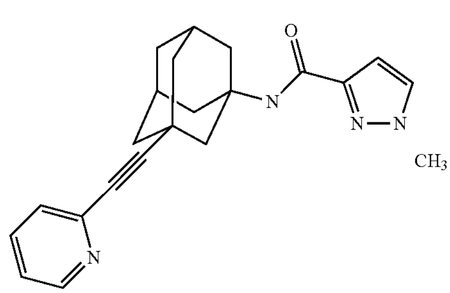 | 1-methyl-N-[3-(pyridin-2-ylethynyl)-1-adamantyl]-1H-pyrazole-3-carboxamide |

TABLE 1-continued
Compounds of formula I
| Example No. | Structure | Chemical Name |
|---|---|---|
| 77 | 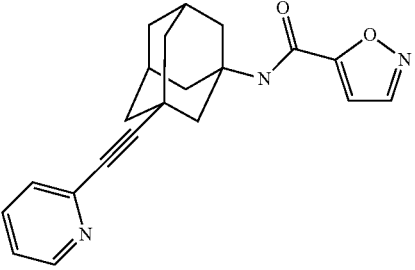 [SMILES: O=C(NC12CC3CC(CC(C#Cc4ccccn4)(C3)C1)C2)c1ccno1] | N-[3-(pyridin-2-ylethynyl)-1-adamantyl]isoxazole-5-carboxamide |
| 78 | 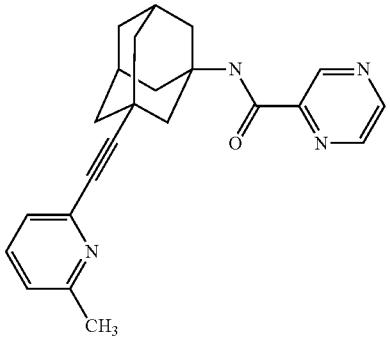 [SMILES: Cc1cccc(C#CC23CC4CC(C2)CC(NC(=O)c2cnccn2)(C4)C3)n1] | N-[3-(6-methylpyridin-2-ylethynyl)-1-adamantyl]pyrazine-2-carboxamide |
| 79 | 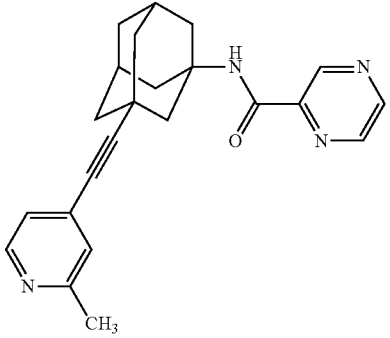 [SMILES: Cc1cc(C#CC23CC4CC(C2)CC(NC(=O)c2cnccn2)(C4)C3)ccn1] | N-[3-(2-methylpyridin-4-ylethynyl)-1-adamantyl]pyrazine-2-carboxamide |
| 80 | 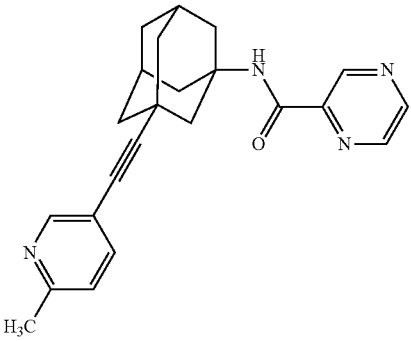 [SMILES: Cc1ccc(C#CC23CC4CC(C2)CC(NC(=O)c2cnccn2)(C4)C3)cn1] | N-[3-(6-methylpyridin-3-ylethynyl)-1-adamantyl]pyrazine-2-carboxamide |

TABLE 1-continued

Compounds of formula I

| Example No. | Structure | Chemical Name |
|---|---|---|
| 81 | 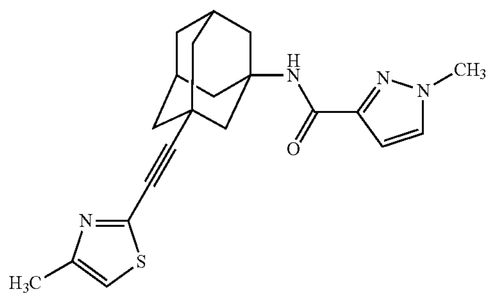 | 1-methyl-N-[3-(4-methylthiazol-2-ylethynyl)-1-adamantyl]-1H-pyrazole-3-carboxamide |

4) Compounds of the Invention

Examples 82-86 of table 2 can be prepared via the processes of Schemes 3-4.

TABLE 2 compounds

| Example No. | Structure | Chemical Name |
|---|---|---|
| 82 | 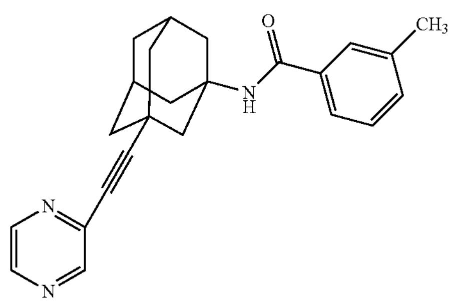 [SMILES: Cc1cccc(C(=O)NC23CC4CC(CC(C#Cc5cnccn5)(C4)C2)C3)c1] | 3-Methyl-N-(3-pyrazin-2-ylethynyl-adamantan-1-yl)-benzamide |
| 83 | 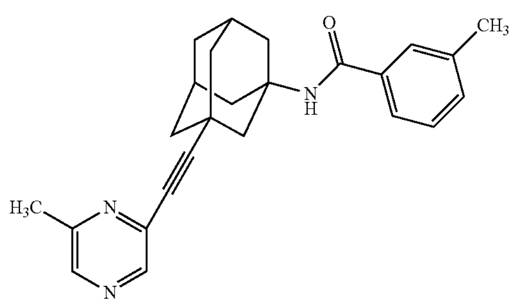 | 3-Methyl-N-[3-(6-methyl-pyrazin-2-ylethynyl)-adamantan-1-yl]-benzamide |
| 84 | 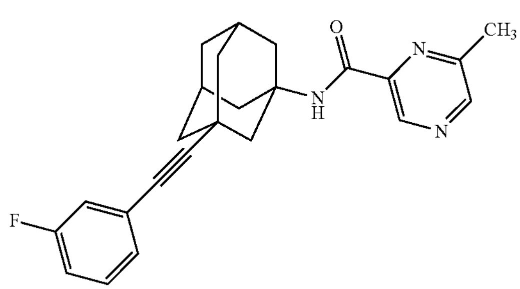 [SMILES: Cc1cncc(C(=O)NC23CC4CC(CC(C#Cc5cccc(F)c5)(C4)C2)C3)n1] | 6-Methyl-pyrazine-2-carboxylic acid[3-(3-fluoro-phenylethynyl)-adamantan-1-yl]-amide |

TABLE 2-continued compounds

| Example No. | Structure | Chemical Name |
|---|---|---|
| 85 | (structure) | 4-Methyl-thiazole-2-carboxylic acid[5-(3-fluoro-phenylethynyl)-bicyclo[3.2.1]oct-1-yl]-amide |
| 86 | (structure) | Pyrazine-2-carboxylic acid[5-(4-methyl-thiazol-2-ylethynyl)-bicyclo[3.2.1]oct-1-yl]-amide |

5) Pharmacological Evaluation of Compounds of the Invention

Compounds of the present invention have been tested in vitro, and can be tested in vitro and in vivo, in the assays as described below.

a) In Vitro Assays i) Radioligand Binding Assays

Binding assays were performed as described in [J. A. O'Brien et al. *Mol Pharmacol.*, 2003, 64, 731-740] with slight modifications, including that a radioligand that binds to the methyl-5-(2-pyridinylethynyl)pyridine (MPEP) binding site was used in place of [$^3$H] MPEP. Briefly, after thawing, the membrane homogenates were resuspended in 50 mM Tris-HCl and 0.9% NaCl binding buffer at pH 7.4 to a final assay concentration of 20 μg protein/well for radioligand filtration binding. Incubations included 5 nM radioligand, membranes and either buffer or varying concentrations of compound. Samples were incubated for 60 min at room temperature with shaking. Non-specific binding was defined with 10 μM cold MPEP when using the radioligand. After incubation, samples were filtered over a GF/C filter (presoaked in 0.25% polyethyleneimine (PEI)) and then washed 4 times using a Tomtec® Harvester 96® Mach III cell harvester (Tomtec, Hamden, Conn.) with 0.5 mL ice-cold 50 mM Tris-HCl (pH 7.4).

$IC_{50}$ values were derived from the inhibition curve and $K_i$ values were calculated according to the Cheng and Prusoff equation of $K_i=IC_{50}/(1+[L]/K_d)$ described in [Y. Cheng and W. H. Prusoff *Biochem. Pharmacal.* 1973, 22, 3099-3108] where [L] is the concentration of radioligand and $K_d$ is its dissociation constant at the receptor, derived from the saturation isotherm. The $K_i$ value for the compounds of invention was about <10 uM. The Ki values for examples 1-81 were within 1.8-1500 nM. The Ki values of some examples are listed in Table 3.

TABLE 3

Affinity of examples

| Example No. | Ki (nM) |
|---|---|
| 3 | 3 |
| 13 | 91 |
| 16 | 4.5 |
| 18 | 10 |
| 20 | 11 |
| 26 | 22 |
| 28 | 17 |
| 30 | 35 |
| 44 | 34 |
| 45 | 6.2 |
| 49 | 590 |
| 50 | 38 |
| 56 | 1300 |
| 71 | 4.7 |
| 81 | 120 | ii) Calcium Mobilization Assay to Test for Negative or Positive Allosteric Activity The cDNA for rat and human metabotropic glutamate receptor 5 (rmGluR5 and hmGluR5, respectively) were generous gifts from S. Nakanishi (Kyoto University, Kyoto, Japan). The rmGluR5 or hmGluR5 was stably expressed in a HEK 293 cell line and gown in Dulbecco's Modified Eagle Medium (DMEM) (Invitrogen, Carlsbad, Calif.) with supplements (10% bovine calf serum, 4 mM glutamine, 100 units/mL penicillin, 100 μg/mL streptomycin and 0.75 mM G1418) at 37° C., 5% $CO_2$. Twenty-four hours prior to assay, cells were seeded into 384-well black wall microtiter plates coated with poly-D-lysine. Just prior to assay, media was aspirated and cells dye-loaded (25 μL/well) with 3 μM Fluo-4/0.01% pluronic acid in assay buffer (Hank's Balanced Saline Solution (HBSS)): 150 mM NaCl, 5 mM KCl, 1 mM $CaCl_2$, 1 mM $MgCl_2$, plus 20 mM N-2-Hydroxyethylpiperazine-N'-2-ethanesulfonic acid (HEPES), pH 7.4, 0.1% bovine serum albumin (BSA) and 2.5 mM probenecid) for 1 hour in 5% $CO_2$ at 37° C. After excess dye was discarded, cells were washed in assay buffer and layered with a final volume equal to 30 μL/well. Basal fluorescence is monitored in a fluorometric imaging plate reader (FLIPR) (Molecular Devices, Sunnyvale, Calif.) with an excitation wavelength of 488 nm and an emission range of 500 to 560 nm. Laser excitation energy was adjusted so that basal fluorescence readings were approximately 10,000 relative fluorescent units. Cells were stimulated with an $EC_{20}$ or an $EC_{80}$ concentration of glutamate in the presence of a compound to be tested, both diluted in assay buffer, and relative fluorescent units were measured at defined intervals (exposure=0.6 sec) over a 3 min period at room temperature. Basal readings derived from negative controls were subtracted from all samples. Maximum change in fluorescence was calculated for each well. Concentration-response curves derived from the maximum change in fluorescence were analyzed by nonlinear regression (Hill equation).

A negative allosteric modulator (NAM) can be identified from these concentration-response curves if a compound produces a concentration dependent inhibition of the $EC_{80}$ glutamate response. The compounds of invention have $IC_{50}$ values less than about 10 uM. The $IC_{50}$ values of some examples are listed in Table 4.

TABLE 4

FLIPR functional $IC_{50}$ of examples

| Example No. | $IC_{50}$ (nM) |
|---|---|
| 3 | 1.2 |
| 16 | 1.6 |
| 17 | 6.6 |
| 23 | 11 |
| 26 | 5.9 |
| 32 | 17 |
| 37 | 5.3 |
| 41 | 9.3 |
| 46 | 12 |
| 51 | 83 |
| 58 | 3.8 |
| 62 | 30 |
| 80 | 700 |

A positive allosteric modulator (PAM) can be identified from these concentration-response curves if a compound produces a concentration dependent increase in the $EC_{20}$ glutamate response.

A silent allosteric modulator (SAM) can be identified by using a combination of both the calcium mobilization assay data and the radioligand binding data. As used herein, the term "silent allosteric modulator" refers to a ligand that binds to an allosteric site of the receptor but has no measurable intrinsic efficacy. A SAM may indirectly demonstrate efficacy by preventing an allosteric binding compound from displaying its own positive (PAM) or negative (NAM) efficacy. From the above definition, if a test compound demonstrates no measurable efficacy in either the NAM-mode or the PAM-mode calcium mobilization assays, and it demonstrates measurable potency in the radioligand assay, it is a silent allosteric modulator (SAM).

b) In Vivo Assays

An in vivo effect of a compound of the present invention may also be evaluated by using the following, non-limiting, examples of in vivo behavioral animal models. The following behavioral models are not intended as the only models useful for determining the efficacy of a compound of formula (I) to treat the corresponding disorder or disease.

A compound of formula (I) can be tested for its in vivo anxiolytic effect in a mouse marble burying (mMB) assay similar to that described in [K. Njung'e, K. and S. L. Handley, *Pharmacology, Biochemistry and Behavior,* 1991, 38, 6367].

For each test, sixty minutes after the injection of vehicle or test compound, or 30 min after injection of the positive control, buspirone, mice are individually placed into test cages containing 1.5 in of Aspen bedding (PWI brand) and two rows of 10 marbles (20 marbles per test cage total). Filter tops are used to cover each test cage. Thirty minutes later, mice are removed from test cages and returned to their home cages. The number of fully visible marbles (less than 2R covered with bedding) are counted and subtracted from 20 to arrive at the number of marbles buried. Twelve mice were tested per group.

Testing includes multiple tests with each test performed to evaluate a positive control, such as buspirone hydrochloride (BUS; Sigma Aldrich) and/or a compound of formula (I). Each compound is dissolved immediately prior to testing in 20% beta-cyclodextrin (compound of formula (I)) or distilled water (BUS) and administered at one or more doses (such as 3, 10, and/or 30 mg/kg) via subcutaneous (SC) or intraperitoneal (IP) injection at the indicated pretreatment times (i.e., 30, 60, or 120 min pretreatment). Doses are measured in mg drug (salt form) per kg body weight. Data can be analyzed using one-way ANOVA with post-hoc Dunnett's test.

Anxiolytic effect in vivo can also be tested via a modified Geller-Seifter conflict test described in [N. A. Moore et al. *Behavioural Pharmacology.* 1994, 5, 196-202]. For example, more specifically, rodent operant chambers (e.g., ENV-007CT, Med Associates Inc. (Georgia, Vt.)) and sound-attenuating chambers (e.g., ENV-018MD, Med Associates Inc.) are used and each chamber is equipped with a house light, cue lights, grid floor to deliver foot shocks via a programmable shocker, (e.g., ENV-414, Med Associates, Inc.) and food hopper. Two levers are located on either side of the food hopper. Rats are trained to only respond on the left lever. Food reinforcement is used (e.g., Dustless Precision Pellets, 45 mg, BioServ, (Frenchtown, N.J.)). MED-PCIV software (Med Associates) can be used to run experimental sessions and collect data.

Prior to beginning the Conflict procedure, animals are initially trained to lever press on fixed ratio schedules (FR 1, 2, 5, and 10). Once animals obtain 25 rewards on a FR 10 schedule for 2 consecutive days, animals begin training on a three component Conflict schedule. The three components are as follows: (1) an unpunished, variable interval 30 s (VI30) schedule of food reinforcement to reinforce lever pressing on a variable time schedule that averages 30 s; this period had a duration of 9 minutes and is signaled by illumination of the rear house light only; (2) immediately following is a 3 minute time out period (TO) that is signaled by total darkness; responding is recorded but is neither rewarded nor punished; (3) a punished, fixed ratio 10 (FR10) schedule of reinforcement that simultaneously presents food and foot shock (0.3 mA, 500 ins) on every tenth lever press during a 3 minute period; this component is signaled by illumination of the rear house light and cue lights above each lever. These three components are repeated twice in the same order during the daily 30 minute session.

Testing begins when stable rates of responding are observed for 5 days (no significant trends up or down). Animals are tested using a Latin-squares design, on, e.g., Wednesdays and Fridays. Animals serve as their own controls and receive all treatments. To maintain baseline performance, animals also are trained the remaining three weekdays.

Testing can be performed using adult, male Sprague-Dawley rats (Charles River Laboratories (Kingston, N.Y.)). Animals can be pair-housed, in colony rooms maintained at controlled temperature (68-72° F.) and a 12-h light/dark cycle (lights on 06:00). Animals are given free access to water, while food is limited to 15 g of Bacon Lover's Treats (BioServ, Frenchtown, N.J.) after training/testing Monday through Thursday. Friday through Sunday, animals have free access to Lab Diet 5012 Rat Diet (PMI Nutrition International, LLC, Brentwood, Mo.) until cages are changed and food removed on Sunday.

Testing includes multiple tests where each test is performed to evaluate either a reference compound or a compound of formula (I). Reference anxiolytics can include chlordiazepoxide, diazepam and buspirone, which are dissolved in saline or water and administered via sc, ip, and/or p.o. Test compounds are dissolved in 20% beta-cyclodextrin, and the pH is adjusted to 7 with NaHCO$_3$. For each test, the compound to be evaluated is tested at one or more doses (such as 10, 20, 30 and/or 50 mg/kg) via p.o. administration, 60 minutes before the test using an injection volume of 2 mL/kg in comparison with a vehicle control group. Doses are measured in mg drug (salt form) per kg body weight. Data can be analyzed using Repeated Measures ANOVA with post-hoc Dunnett's test.

The "Vogel Conflict Test" as described by Vogel et al. [*Psychopharmacologia*, 1971, 21, 1-7] can be used to detect anxiolytic activity of a compound of formula (I) because anxiolytics increase punished drinking. In the test, rats are deprived of water for approximately 48 hours and then are placed individually into a transparent Plexiglas® enclosure (15×32×34 cm$^3$) with a floor consisting of stainless steel bars (0.4 cm) spaced 1 cm apart. The back wall of the enclosure is made of opaque Plexiglas®, thereby concealing the observer from the experimental animal. In the center of the opposite wall, 5 cm above the floor, a metal water spout protrudes into the cage and is connected to one pole of a shock generator (Apelex: Type 011346). The other pole of the shock generator is connected to the metal grid floor.

The rat is left to explore until it finds the water spout. Then, every time it drinks, it receives a slight electric shock (1.7 mA, 1 s) 2 seconds after it starts lapping. The number of punished drinks is counted during a 3 minute test. The test is performed blind. Testing includes multiple tests using reference compounds and a compound of formula (I) that is prepared and administered as described below in the LES test. Male Rj: Wistar (Hans) rats as described therein can be used after acclimatization conditions are achieved. Data can be analyzed by comparing treated groups with appropriate controls using unpaired Student's t tests.

One exemplified example demonstrated anxiolitic-like activity in the Vogel test at 0.3 mg/kg, PO.

Those skilled in the art will recognize that various changes and/or modifications may be made to aspects or embodiments of this invention and that such changes and/or modifications may be made without departing from the spirit of this invention. Therefore, it is intended that the appended claims cover all such equivalent variations as will fall within the spirit and scope of this invention.

The invention claimed is:
1. A compound of formula (I):

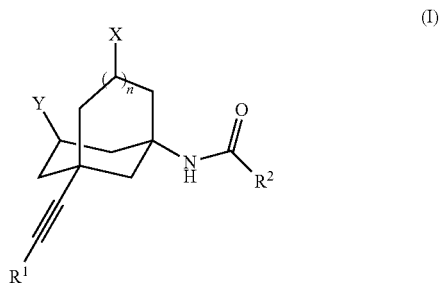

wherein:
R$^1$ and R$^2$ are independently aryl, heteroaryl, heterocyclyl which is optionally mono-, di-, or tri-substituted independently with alkyl, halogen, hydroxy, cyano, amino, alkylamino, dialkylamino, acyl, aryl, heteroaryl, heterocyclyl, cycloalkyl, ketocycloalkyl, alkoxy, hydroxylalkyl, trifluoromethyl; and
When n=0 and 1, X and Y are H; and
When n=1, both X and Y are bonds that are linked to —CH$_2$— to form a tricyclic adamantyl core.

2. The compound of claim 1, wherein R$^1$ and R$^2$ are both heteroaryl.

3. The compound of claim 1, wherein either R$^1$ or R$^2$ is heteroaryl.

4. The compound of claim 1, wherein either R$^1$ or R$^2$ is substituted aryl or heteroaryl.

5. The compound of claim 1, wherein R$^1$ and R$^2$ is alkyl substituted heteroaryl.

6. The compound of claim 1, wherein R$^1$ is halogen substituted aryl.

7. The compound of claim 6, wherein the halogen, is fluorine or chlorine.

8. The compound of claim 1, wherein R$^2$ is alkyl substituted heteroaryl.

9. The compound of claim 8 wherein the alkyl, is methyl.

10. The compound of claim 1, wherein R$^1$ is aryl and R$^2$ is heteroaryl.

11. The compound of claim 1, wherein at least one aryl is phenyl.

12. The compound of claim 1, wherein the mono-, di-, or tri-substituents are independently selected from the group consisting of alkyl, halogen, hydroxy, cyano, amino, alkylamino, dialkylamino, acyl, aryl, heteroaryl, heterocyclyl, cycloalkyl, ketocycloalkyl, alkoxy, hydroxylalkyl, trifluoromethyl.

13. The compound of claim 1, wherein the compound is:
Pyrazine-2-carboxylic acid [5-(6-methyl-pyridin-2-ylethynyl)-bicyclo[3.2.1]oct-1-yl]-amide;
Pyrazine-2-carboxylic acid [5-(6-fluoro-pyridin-2-ylethynyl)-bicyclo[3.2.1]oct-1-yl]-amide;
Pyrazine-2-carboxylic acid [5-(3-fluoro-phenylethynyl)-bicyclo[3.2.1]oct-1-yl]-amide;
Pyrazine-2-carboxylic acid [5-(3-chloro-phenylethynyl)-bicyclo[3.2.1]oct-1-yl]-amide;
Pyrazine-2-carboxylic acid [5-(3-fluoro-pyridin-2-ylethynyl)-bicyclo[3.2.1]oct-1-yl]-amide;
6-Methyl-pyrazine-2-carboxylic acid [5-(3-fluoro-phenylethynyl)-bicyclo[3.2.1]oct-1-yl]-amide;
6-Methyl-pyrazine-2-carboxylic acid (5-pyridin-2-ylethynyl-bicyclo[3.2.1]oct-1-yl)-amide;

6-Methyl-pyrazine-2-carboxylic acid [5-(2-methyl-pyrimidin-4-ylethynyl)-bicyclo[3.2.1]oct-1-yl]-amide;
Pyridine-2-carboxylic acid [5-(6-methyl-pyridin-2-ylethynyl)-bicyclo[3.2.1]oct-1-yl]-amide;
Pyridine-2-carboxylic acid [5-(6-methyl-pyrazin-2-ylethynyl)-bicyclo[3.2.1]oct-1-yl]-amide;
6-Methyl-pyridine-2-carboxylic acid (5-pyridin-2-ylethynyl-bicyclo[3.2.1]oct-1-yl)-amide;
6-Methyl-pyridine-2-carboxylic acid [5-(6-methyl-pyridin-2-ylethynyl)-bicyclo[3.2.1]oct-1-yl]-amide;
3-Chloro-N-(5-pyrazin-2-ylethynyl-bicyclo[3.2.1]oct-1-yl)-benzamide;
6-Methyl-N-((1R,5S)-5-(pyridin-2-ylethynyl)bicyclo[3.2.1]octan-1-yl)pyrazine-2-carboxamide;
6-Methyl-N-((1R,5S)-5-(pyridin-2-ylethynyl)bicyclo[3.2.1]octan-1-yl)picolinamide;
N-((1R,5S)-5-(pyridin-2-ylethynyl)bicyclo[3.2.1]octan-1-yl)picolinamide;
N-((1R,5S)-5-pyridin-2-ylethynyl)bicyclo[3.2.1]octan-1-yl)pyrazine-2-carboxamide;
2-Methyl-N-((1R,5S)-5-(pyridin-2-ylethynyl)bicyclo[3.2.1]octan-1-yl)pyrimidine-4-carboxamide;
N-((1R,5S)-5-(pyridin-2-ylethynyl)bicyclo[3.2.1]octan-1-yl)pyrimidine-4-carboxamide;
5-Fluoro-N-((1R,5S)-5-(pyridin-2-ylethynyl)bicyclo[3.2.1]octan-1-yl)picolinamide;
5-Methyl-N-((1R,5S)-5-(pyridin-2-ylethynyl)bicyclo[3.2.1]octan-1-yl)picolinamide;
1-Methyl-N-((1R,5S)-5-(pyridin-2-ylethynyl)bicyclo[3.2.1]octan-1-yl)-1H-pyrazole-3-carboxamide;
3-Fluoro-N-((1R,5S)-5-(pyridin-2-ylethynyl)bicyclo[3.2.1]octan-1-yl)picolinamide;
6-Methyl-N-((1S,5R)-5-(pyridin-2-ylethynyl)bicyclo[3.2.1]octan-1-yl)pyrazine-2-carboxamide;
6-Methyl-N-((1S,5R)-5-(pyridin-2-ylethynyl)bicyclo[3.2.1]octan-1-yl)picolinamide;
N-((1S,5R)-5-(pyridin-2-ylethynyl)bicyclo[3.2.1]octan-1-yl)picolinamide;
N-((1S,5R)-5-(pyridin-2-ylethynyl)bicyclo[3.2.1]octan-1-yl)pyrazine-2-carboxamide;
2-Methyl-N-((1S,5R)-5-(pyridin-2-ylethynyl)bicyclo[3.2.1]octan-1-yl)pyrimidine-4-carboxamide;
N-((1S,5R)-5-(pyridin-2-ylethynyl)bicyclo[3.2.1]octan-1-yl)pyrimidine-4-carboxamide;
5-Fluoro-N-((1S,5R)-5-(pyridin-2-ylethynyl)bicyclo[3.2.1]octan-1-yl)picolinamide;
5-Methyl-N-((1S,5R)-5-(pyridin-2-ylethynyl)bicyclo[3.2.1]octan-1-yl)picolinamide;
1-Methyl-N-((1S,5R)-5-(pyridin-2-ylethynyl)bicyclo[3.2.1]octan-1-yl)-1H-pyrazole-3-carboxamide;
3-Fluoro-N-((1S,5R)-5-(pyridin-2-ylethynyl)bicyclo[3.2.1]octan-1-yl)picolinamide;
N-((1R,5S)-5-((6-methylpyridin-2-yl)ethynyl)bicyclo[3.2.1]octan-1-yl)pyrazine-2-carboxamide;
N-((1R,5S)-5-((6-methylpyridin-2-yl)ethynyl)bicyclo[3.2.1]octan-1-yl)picolinamide;
N-((1S,5R)-5-((6-methylpyridin-2-yl)ethynyl)bicyclo[3.2.1]octan-1-yl)pyrazine-2-carboxamide;
N-((1S,5R)-5-((6-methylpyridin-2-yl)ethynyl)bicyclo[3.2.1]octan-1-yl)picolinamide;
N-((1R,5S)-5-((6-fluoropyridin-2-yl)ethynyl)bicyclo[3.2.1]octan-1-yl)pyrazine-2-carboxamide;
N-((1S,5R)-5-((6-fluoropyridin-2-yl)ethynyl)bicyclo[3.2.1]octan-1-yl)pyrazine-2-carboxamide;
N-((1R,5S)-5-((3-fluoropyridin-2-yl)ethynyl)bicyclo[3.2.1]octan-1-yl)pyrazine-2-carboxamide;
N-((1S,5R)-5-((3-fluoropyridin-2-yl)ethynyl)bicyclo[3.2.1]octan-1-yl)pyrazine-2-carboxamide;
N-((1R,5S)-5-(pyrazin-2-ylethynyl)bicyclo[3.2.1]octan-1-yl)picolinamide;
6-Methyl-N-((1R,5S)-5-(pyrazin-2-ylethynyl)bicyclo[3.2.1]octan-1-yl)picolinamide;
1-Methyl-N-((1R,5S)-5-(pyrazin-2-ylethynyl)bicyclo[3.2.1]octan-1-yl)-1H-pyrazole-3-carboxamide;
4-Methyl-N-((1R,5S)-5-(pyrazin-2-ylethynyl)bicyclo[3.2.1]octan-1-yl)thiazole-2-carboxamide;
2-Methyl-N-((1R,5S)-5-(pyrazin-2-ylethynyl)bicyclo[3.2.1]octan-1-yl)thiazole-4-carboxamide;
N-((1S,5R)-5-(pyrazin-2-ylethynyl)bicyclo[3.2.1]octan-1-yl)picolinamide;
6-Methyl-N-((1S,5R)-5-(pyrazin-2-ylethynyl)bicyclo[3.2.1]octan-1-yl)picolinamide;
1-Methyl-N-((1S,5R)-5-(pyrazin-2-ylethynyl)bicyclo[3.2.1]octan-1-yl)-1H-pyrazole-3-carboxamide;
4-Methyl-N-((1S,5R)-5-(pyrazin-2-ylethynyl)bicyclo[3.2.1]octan-1-yl)thiazole-2-carboxamide;
2-Methyl-N-((1S,5R)-5-(pyrazin-2-ylethynyl)bicyclo[3.2.1]octan-1-yl)thiazole-4-carboxamide;
N-((1R,5S)-5-((2-methylthiazol-4-yl)ethynyl)bicyclo[3.2.1]octan-1-yl)pyrazine-2-carboxamide;
N-((1S,5R)-5-((2-methylthiazol-4-yl)ethynyl)bicyclo[3.2.1]octan-1-yl)pyrazine-2-carboxamide;
3-Chloro-N-[3-(6-methylpyrazin-2-ylethynyl)-1-adamantyl]benzamide;
3-Chloro-N-[3-(pyrazin-2-ylethynyl)-1-adamantyl]benzamide;
3-Fluoro-N-[3-(6-methylpyrazin-2-ylethynyl)-1-adamantyl]benzamide;
3-Fluoro-N-[3-(pyrazin-2-ylethynyl)-1-adamantyl]benzamide;
6-Methyl-N-[3-(pyridin-3-ylethynyl)-1-adamantyl]pyrazine-2-carboxamide;
6-Methyl-N-[3-(pyridin-4-ylethynyl)-1-adamantyl]pyrazine-2-carboxamide;
6-Methyl-N-[3-(pyridin-2-ylethynyl)-1-adamantyl]pyrazine-2-carboxamide;
N-[3-(pyrazin-2-ylethynyl)-1-adamantyl]pyridine-2-carboxamide;
5-Fluoro-N-[3-(pyrazin-2-ylethynyl)-1-adamantyl]nicotinamide;
2-Methyl-N-[3-(pyrazin-2-ylethynyl)-1-adamantyl]pyrimidine-4-carboxamide;
6-Methyl-N-[3-(pyrazin-2-ylethynyl)-1-adamantyl]pyridine-2-carboxamide;
5-Fluoro-N-[3-(pyrazin-2-ylethynyl)-1-adamantyl]pyridine-2-carboxamide;
1-Methyl-N-[3-(pyrazin-2-ylethynyl)-1-adamantyl]-1H-pyrazole-3-carboxamide;
3-Cyano-N-[3-(pyrazin-2-ylethynyl)-1-adamantyl]benzamide;
2-Methyl-N-[3-(6-methylpyrazin-2-ylethynyl)-1-adamantyl]pyrimidine-4-carboxamide;
N-[3-(6-methylpyrazin-2-ylethynyl)-1-adamantyl]pyridine-2-carboxamide;
5-Fluoro-N-[3-(6-methylpyrazin-2-ylethynyl)-1-adamantyl]nicotinamide;
N-[3-(pyridin-2-ylethynyl)-1-adamantyl]pyrazine-2-carboxamide;
N-[3-(pyridin-2-ylethynyl)-1-adamantyl]pyridine-2-carboxamide;
6-Methyl-N-[3-(pyridin-2-ylethynyl)-1-adamantyl]pyridine-2-carboxamide;

2-Methyl-N-[3-(pyridin-2-ylethynyl)-1-adamantyl]pyrimidine-4-carboxamide;

N-[3-(pyridin-2-ylethynyl)-1-adamantyl]pyrimidine-4-carboxamide;

1-Methyl-N-[3-(pyridin-2-ylethynyl)-1-adamantyl]-1H-pyrazole-3-carboxamide;

N-[3-(pyridin-2-ylethynyl)-1-adamantyl]isoxazole-5-carboxamide;

N-[3-(6-methylpyridin-2-ylethynyl)-1-adamantyl]pyrazine-2-carboxamide;

N-[3-(2-methylpyridin-4-ylethynyl)-1-adamantyl]pyrazine-2-carboxamide;

N-[3-(6-methylpyridin-3-ylethynyl)-1-adamantyl]pyrazine-2-carboxamide; and

1-Methyl-N-[3-(4-methylthiazol-2-ylethynyl)-1-adamantyl]-1H-pyrazole-3-carboxamide;

or a pharmaceutically acceptable salt thereof.

14. A pharmaceutical composition comprising the compound of claim 1 and at least one pharmaceutical excipient.

* * * * *